United States Patent
Adams et al.

(10) Patent No.: US 11,701,428 B2
(45) Date of Patent: Jul. 18, 2023

(54) THERAPEUTIC COMBINATIONS COMPRISING ANTI-CD123 IMMUNOCONJUGATES

(71) Applicant: ImmunoGen, Inc., Waltham, MA (US)

(72) Inventors: Sharlene Adams, Waltham, MA (US); Callum M. Sloss, Wakefield, MA (US); Patrick Zweidler-McKay, Lincoln, MA (US)

(73) Assignee: ImmunoGen, Inc., Waltham, MA (US)

(*) Notice: Subject to any disclaimer, the term of this patent is extended or adjusted under 35 U.S.C. 154(b) by 60 days.

(21) Appl. No.: 16/862,358

(22) Filed: Apr. 29, 2020

(65) Prior Publication Data
US 2021/0023237 A1    Jan. 28, 2021

Related U.S. Application Data

(60) Provisional application No. 62/860,598, filed on Jun. 12, 2019, provisional application No. 62/839,974, filed on Apr. 29, 2019.

(51) Int. Cl.
*A61K 47/68* (2017.01)
*A61P 35/00* (2006.01)
*C07K 16/28* (2006.01)

(52) U.S. Cl.
CPC .......... *A61K 47/6849* (2017.08); *A61P 35/00* (2018.01); *C07K 16/2866* (2013.01)

(58) Field of Classification Search
CPC .... A61K 47/6849; A61K 45/06; A61K 38/00; A61K 31/635; A61K 31/706; A61K 47/6803; A61K 39/395; A61P 35/00; A61P 35/02; C07K 16/2866; C07K 2317/77
See application file for complete search history.

(56) References Cited

U.S. PATENT DOCUMENTS

| | | | |
|---|---|---|---|
| 2017/0029514 A1* | 2/2017 | Kovtun | A61P 35/02 |
| 2017/0152321 A1 | 6/2017 | Bergstein | |
| 2018/0169261 A1 | 6/2018 | Sutherland et al. | |
| 2019/0111147 A1 | 4/2019 | Fleming et al. | |
| 2019/0112359 A1 | 4/2019 | Liu et al. | |
| 2020/0157228 A1* | 5/2020 | Zweidler-McKay | C07K 16/2866 |

FOREIGN PATENT DOCUMENTS

| | | | |
|---|---|---|---|
| WO | WO-2017004026 A1 * | 1/2017 | A61K 47/6801 |
| WO | WO-2017004025 A1 | 5/2017 | |
| WO | WO-2017004026 A1 | 5/2017 | |
| WO | WO-2017091745 A1 | 6/2017 | |
| WO | WO-2018098258 A2 | 5/2018 | |
| WO | WO-2019012328 A1 | 1/2019 | |
| WO | WO-2019060707 A1 | 3/2019 | |
| WO | WO-2019060718 A1 | 3/2019 | |
| WO | WO-2020092533 A2 | 5/2020 | |
| WO | WO-2020223351 A1 | 11/2020 | |

OTHER PUBLICATIONS

Walter, et al., Blood 2004, vol. 103, No. 11 (Year: 2004).*
Bogenberger, et al., Leukemia 2014 vol. 28, p. 1657-1665 (Year: 2014).*
Prescriber's Digital Reference (PDR) 2013; URL: https://www.pdr.net/drug-summary/Vidaza-azacitidine-1664; accessed Dec. 11, 2021 (Year: 2013).*
FDA (prescribing information for ventoclax), Apr. 2016, Reference ID: 3915259 (Year: 2016).*
Buckley, et al., Am J Hematol. 2014; 89(4): p. 423-428 (Year: 2014).*
Xie, et al., Blood Cancer Journal 2017 7 e567 (Year: 2017).*
Diesch, et al., Clinical Epigenetics 2016 8:71 (Year: 2016).*
Mie, et al., Updates in Clinical Trials for Hematological Diseases 2018 (Year: 2018).*
Adams, S., et al., "The Combination of IMGN632, a CD123-Targeting ADC, with Venetoclax Enhances Anti-Leukemic Activity In Vitro and Prolongs Survival In Vivo in Pre-Clinical Models of Human AML," *EHA Library:* Abstract #201, 2 pages, European Hematology Association, United States (Jun. 2019).
Adams, S., et al., "The Combination of IMGN632, a CD123-Targeting ADC, with Venetoclax Enhances Anti-Leukemic Activity In vitro and Prolongs Survival In vivo in Pre-Clinical Models of Human AML," presented at the 24$^{th}$ Congress of the European Hematology Association, Jun. 13-16, 2019, Poster #201, 1 page, United States (Jun. 2019).
Bissery, M-C., et al., "Experimental antitumor activity of taxotere (RP 56976, NSC 628503), a Taxol Analogue," *Cancer Research* 51(18):4845-4852, American Association for Cancer Research Inc., United States (1991).
Daver, N.G., et al., "A Phase I, First-in-Human Study Evaluating the Safety and Preliminary Antileukemia Activity of IMGN632, a Novel CD123-Targeting Antibody-Drug Conjugate, in Patients with Relapsed/Refractory Acute Myeloid Leukemia and Other CD123-Positive Hematologic Malignancies," *Blood 132*(Supplement_1):27, Abstract #613, 5 pages, American Society of Hematology, United States (Nov. 2018).
Daver, N.G., et al., "A Phase I, First-in-Human Study Evaluating the Safety and Preliminary Antileukemia Activity of IMGN632, a Novel CD123-Targeting Antibody-Drug Conjugate, in Patients with Relapsed/Refractory Acute Myeloid Leukemia and Other CD123-Positive Hematologic Malignancies," presented at the 60$^{th}$ American Society of Hematology Meeting, Dec. 1-4, 2018, 16 pages.

(Continued)

*Primary Examiner* — Julie Wu
*Assistant Examiner* — John L Van Druff
(74) *Attorney, Agent, or Firm* — Sterne, Kessler, Goldstein & Fox P.L.L.C.

(57) ABSTRACT

Therapeutic combinations of immunoconjugates that bind to CD123 (e.g., IMGN632) with BCL-2 inhibitors (e.g., venetoclax), and/or a hypomethylating agent (e.g., azacitidine or decitabine) are provided. Methods of administering the combinations to treat hematological malignancies with clinical efficacy and/or decreased toxicity are also provided. Methods of treating hematological malignances present as minimal residual disease using immunoconjugates that bind to CD123 (e.g., IMGN632) are also provided.

40 Claims, 27 Drawing Sheets

Specification includes a Sequence Listing.

(56) References Cited

OTHER PUBLICATIONS

Daver, N.G., et al., "A Phase I Study of IMGN632, a Novel CD123-Targeting Antibody-Drug Conjugate, in Patients with Relapsed/Refractory Acute Myeloid Leukemia, Blastic Plasmacytoid Dendritic Cell Neoplasm, and Other CD123-Positive Hematologic Malignancies," *Blood (ASH Annual Meeting Abstracts) 134*(Supplement_1): Abstract #1334, 2 pages, American Society of Hematology, United States (Nov. 2019).

Daver, N.G., et al., "A Phase I Study of IMGN632, a Novel CD123-Targeting Antibody-Drug Conjugate, in Patients with Relapsed/Refractory Acute Myeloid Leukemia, Blastic Plasmacytoid Dendritic Cell Neoplasm, and Other CD123-Positive Hematologic Malignancies," presented at the 61st American Society of Hematology Annual Meeting, Dec. 7-10, 2019, Poster #1334, 1 page, United States (Dec. 2019).

Daver, N.G., et al., "A phase 1/2 study of IMGN632, a novel CD123-targeting antibody-drug conjugate, in patients with relapsed/refractory acute myeloid leukemia, blastic plasmacytoid dendritic cell neoplasm, and other CD123-positive hematologic malignancies," *Journal of Clinical Oncology 38*(15_Supplement): Abstract #TPS7563, 1 page, American Society of Clinical Oncology, United States (May 2020).

Daver, N.G., et al., "A Phase 1b/2 Study of the CD123-Targeting Antibody-Drug Conjugate IMGN632 as Monotherapy or in Combination with Venetoclax and/or Azacitidine for Patients with CD123-Positive Acute Myeloid Leukemia," *Blood (ASH Annual Meeting Abstracts) 134*(Supplement_1): Abstract #2601, 2 pages, American Society of Hematology, United States (Nov. 2019).

Daver, N.G., et al., "A Phase 1b/2 Study of IMGN632 as Monotherapy or Combination with Venetoclax and/or Azacitidine for Patients with CD 123-Positive Acute Myeloid Leukemia," presented at the 61st American Society of Hematology Annual Meeting, Dec. 7-10, 2019, Poster #2601, 1 page, United States (Dec. 2019).

Daver, N.G., et al., "Clinical Profile of IMGN632, a Novel CD123-Targeting Antibody-Drug Conjugate (ADC), in Patients with Relapsed/Refractory (R/R) Acute Myeloid Leukemia (AML) or Blastic Plasmacytoid Dendritic Cell Neoplasm (BPDCN)," *Blood (ASH Annual Meeting Abstracts) 134*(Supplement_1): Abstract #734, 3 pages, American Society of Hematology, United States (Nov. 2019).

Daver, N.G., et al., "Encouraging Clinical Profile of IMGN632, a Novel CD123-Targeting Antibody-Drug Conjugate (ADC), in Patients with Relapsed/Refractory (R/R) Acute Myeloid Leukemia (AML) or Blastic Plasmacytoid Dendritic Cell Neoplasm (BPDCN)," presented at the 61st American Society of Hematology Annual Meeting, Dec. 7-10, 2019, Abstract #734, 15 pages, United States (Dec. 2019).

Evans, K., et al., "Pediatric Preclinical Testing consortium evaluation of the CD123 antibody drug conjugate, IMGN632, against xenograft models of pediatric acute lymphoblastic leukemia," *Cancer Research 79*(13 Supplement): Abstract #4820, 2 pages, American Association for Cancer Research, United States (Mar. 29-Apr. 3, 2019).

Fritz, C., et al., "Synergistic Anti-Leukemic Activity of PARP inhibition combined with IMGN632, an Anti-CD123 Antibody-drug conjugate in acute myeloid leukemia models," *Blood (ASH Annual Meeting Abstracts) 132*(Supplement_1): Abstract #2647, 7 pages, American Society of Hematology, United States (Nov. 2018).

Fritz, C., et al., "Synergistic Anti-Leukemic Activity of PARP inhibition combined with IMGN632, an Anti-CD123 Antibody-drug conjugate in acute myeloid leukemia models," presented at the 60th American Society of Hematology Annual Meeting, Dec. 1-4, 2018, Poster #2647, 1 page, United States (Dec. 2018).

Goldstone, A.H., et al., "In adults with standard-risk acute lymphoblastic leukemia, the greatest benefit is achieved from a matched sibling allogeneic transplantation in first complete remission, and an autologous transplantation is less effective than conventional consolidation/maintenance chemotherapy in all patients: final results of the International ALL Trial (MRC UKALL XII/ECOG E2993)," *Blood 111*(4):1827-1833, American Society of Hematology, United States (2008).

International Search Report and Written Opinion for International Application No. PCT/US19/58824, International Search Authority, United States, dated Jan. 27, 2020, 12 pages.

International Search Report and Written Opinion for International Application No. PCT/US2020/030478, International Search Authority, United States, dated Sep. 18, 2020, 10 pages.

Jordan, C.T., et al., "The interleukin-3 receptor alpha chain is a unique marker for human acute myelogenous leukemia stem cells," *Leukemia 14*(10):1777-84, Nature Publishing Group, United Kingdom (2000).

Knight, T., et al., "Evaluating venetoclax and its potential in treatment-naïve acute myeloid leukemia," *Cancer Manag Res 11*:3197-3213, Dove Medical Press Ltd., New Zealand (2019).

Kovtun, Y., et al., "A CD123-targeting antibody-drug conjugate, IMGN632, designed to eradicate AML while sparing normal bone marrow cells," *Blood Advances 2*(8):848-858, American Society of Hematology, United States (Apr. 2018).

Kuruvilla, V.M., et al., "IMGN632, a CD123-Targeting ADC Bearing a DNA-Alkylating IGN Payload, Combines Effectively with Azacitidine and Venetoclax In Vivo, Prolonging Survival in Preclinical Models of Human Acute Myeloid Leukemia (AML)," *Blood (ASH Annual Meeting Abstracts) 134*(Supplement_1): Abstract #1375, 4 pages, American Society of Hematology, United States (Nov. 2019).

Kuruvilla et al. "IMGN632, a CD123-Targeting [sic]ADC Bearing a DNA-Alkylating IGN Payload, Combines Effectively with Azacitidine and Venetoclax In Vivo, Prolonging Survival in Preclinical Models of Human Acute Myeloid Leukemia (AML)," presented at the 61st American Society of Hematology Annual Meeting, Dec. 7-10, 2019, Poster #1375, 1 page, United States (Dec. 2019).

U.S. Appl. No. 62/860,598, inventors Adams; S., et al., filed Jun. 12, 2019.

Siegel, R.L., et al., "Cancer Statistics, 2017," *CA: A Cancer Journal for Clinicians 67*(1):7-30, John Wiley & Sons, United States (2017).

Testa, U., et al., "CD 123 is a membrane biomarker and a therapeutic target in hematologic malignancies," *Biomark Res. 2*(1):4, 11 pages, BioMed Central Ltd., United Kingdom (2014).

Daver, N.G., et al., "Encouraging Clinical Profile of IMGN632, a Novel CD123-Targeting Antibody-Drug Conjugate, in Patients with Relapsed/Refractory Acute Myeloid Leukemia or Blastic Plasmacytoid Dendritic Cell Neoplasm," Presentation at the 61st American Society of Hematology Annual Meeting, Dec. 7-10, 2019, 15 pages, United States.

Pemmaraju, N., et al., "Clinical Profile of IMGN632, a Novel CD123-Targeting Antibody-Drug Conjugate (ADC), in Patients with Relapsed/Refractory (R/R) Blastic Plasmacytoid Dendritic Cell Neoplasm (BPDCN)," Abstract #167, 11 pages, presented at the 62nd American Society of Hematology Annual Meeting Dec. 5, 2020, United States.

Pemmaraju, N., et al., "Experience with IMGN632, a Novel CD123-Targeting Antibody-Drug Conjugated (ADC), in Frontline Patients with Blastic Plasmacytoid Dendritic Cell Neoplasm (BPDCN)," Abstract #1284, 1 page, Presented at the American Society of Hematology 63rd Annual Meeting, Dec. 2021, United States.

Prokop, A., et al., "Induction of apoptosis by enediyne antibiotic calicheamicin θII proceeds through a caspase-mediated mitochondrial amplification loop in an entirely Bax-dependent manner," *Oncogene 22*:9107-9120, Springer Nature, Germany (2003).

Daver, N., et al., "Safety and Efficacy from a Phase 1b/2 Study of IMGN632 in Combination with Azacitidine and Venetoclax for Patients with CD123-Positive Acute Myeloid Leukemia," Abstract #372, 12 pages, Presented at the American Society of Hematology 63rd Annual Meeting, Dec. 2021, United States.

Kuruvilla, V.M., et al., "Combining IMGN632, a Novel CD123-Targeting Antibody Drug Conjugate with Azacitidine and Venetoclax facilitates Apoptosis in vitro and Prolongs Survival in vivo in AML Models," 10 pages, Presentation at the 62nd American Society of Hematology Annual Meeting, Dec. 2020, United States.

Kuruvilla, V.M., et al., "IMGN632, a CD123-Targeting ADC Bearing a DNA-Alkylating IGN Payload, Combines Effectively as a

(56) References Cited

OTHER PUBLICATIONS

Triplet Regimen with Azacitidine and Venetoclax In Vivo, Prolonging Survival in Preclinical Models of Human Acute Myeloid Leukemia (AML)," Abstract# AML-367, 1 Page, Society of Hematologic Oncology 2020 Annual Meeting, Sep. 2020, United States.
Pemmaraju, N., et al., "A Study of IMGN632, a Novel CD123-Targeting Antibody-Drug Conjugate, for Patients with Frontline and Relapsed/Refractory Blastic Plasmacytoid Dendritic Cell Neoplasm (BPDCN)," Abstract from the American Society of Hematology 63rd Annual Meeting, Dec. 11-14, 2021, United States.
Daver, N., et al., "Pivekimab sunirine (PVEK) triplet with azacitidine and venetoclax shows broad activity in adverse genetic subsets of relapsed/refractory AML and reduced infusion related reactions," presented at the Tenth Annual Meeting of the Society of Hematologic Oncology, Sep. 8-Oct. 2, 2022, Abstract 0000, 1 page, United States (2022).
Daver, N., et al., "Broad activity for the pivekimab sunirine (PVEK, IMGN632), azacitidine, and venetoclax triplet in high-risk patients with relapsed/refractory and frontline acute myeloid leukemia (AML)," presented at 64$^{th}$ ASH Annual Meeting and Exposition, Dec. 10-13, 2022, Presentation #62, Louisiana, United States, 16 pages.
Daver, N., et al., "Pivekimab sunirine (PVEK) triplet with azacitidine and venetoclax shows broad activity in adverse genetics subsets of relapsed/refractory AML and reduced infusion related reactions," presented at 2022 Annual Conference of the Society of Hematologic Oncology, Oct. 23-26, 2022, Rome, Italy, 13 pages.
Kondo, N., et al., "DNA Damage Induced by Alkylating Agents and Repair Pathways," J. Nucleic Acids, Article ID 543531, 7 pages, SAGE—Hindawi, United Arab Emirates (2010).
Laing, A.A., et al., "Unlocking the potential of anti-CD33 therapy in adult and childhood acute myeloid leukemia," Experimental Hematology 54:40-50, Elsevier, Netherlands (2017).
Zong, W., et al., "Alkylating DNA damage stimulates a regulated form of necrotic cell death," Genes & Development, 18:1272-1282, Cold Spring Harbor Laboratory Press, United States (2004).
Tolcher, A.W., "Antibody drug conjugates: lessons from 20 years of clinical experience," Annals of Oncology 27:2168-2172 (2016).
Pemmaraju, N., et al., "Cadenza: A Pivotal Study of Pivekimab Sunirine (IMGN632) in Patients with Untreated/Frontline BPDCN," CADENZA, https://BPDCNtrial.com, NCT03386513, European Hematology Association, The Netherlands, 1 page (2022).
Daver, N. G., et al., "A Phase 1b/2 Study of the CD123-Targeting Antibody-Drug Conjugate Pivekimab Sunirine (IMGN632) in Combination with Venetoclax (VEN) and Azacitidine (AZA) for Patients with CD123-Positive Acute Myeloid Leukemia," NCT04086264, European Hematology Association, The Netherlands, 1 page (2022).
Angelova, E., et al., "CD123 expression patterns and selective targeting with a CD123-targeted antibody-drug conjugate (IMGN632) in acute lymphoblastic leukemia," Haematologica 104(4):749-755, the Ferrata Storti Foundation, Italy (Oct. 2018).
ClinicalTrials.gov, "IMGN632 as Monotherapy or With Venetoclax and/or Azacitidine for Patients With CD123-Positive Acute Myeloid Leukemia," Identifier NCT 04086264, accessed at https://clinicaltrials.gov/ct2/show/NCT04086264?term=04086264&draw=2&rank=1, first posted Sep. 11, 2019, accessed on Jan. 17, 2023, 10 pages.
Kuruvilla, V.M., et al., "Combining IMGN632, a Novel CD123-Targeting Antibody Drug Conjugate with Azacitidine and Venetoclax Facilitates Apoptosis in Vitro and Prolongs Survival In Vivo in AML Models," Blood 136(S1):32, 4 pages, American Society of Hematology, United States (Nov. 2020).
Adams, S., et al., "PF201 The Combination of IMGN632, a CD123-Targeting ADC, With Venetoclax Enhances Anti-Leukemic Activity In Vitro and Prolongs Survival In Vivo in Pre-Clinical Models of Human AML," Hemasphere 3(S1):53, Wolters Kluwer Health, Netherlands (Jun. 2019).
Li, F., et al., "Characterization of SGN-CD123A, A Potent CD 123-Directed Antibody-Drug Conjugate for Acute Myeloid Leukemia," Molecular Cancer Therapeutics 17(2):554-564, American Association for Cancer Research, United States (Nov. 2017).
Co-pending U.S. Appl. No. 18/054,076, filed Nov. 9, 2022, inventor Zweidler-McKay; P., et al., (Unpublished).

* cited by examiner

THERAPEUTIC COMBINATIONS COMPRISING ANTI-CD123 IMMUNOCONJUGATES

REFERENCE TO RELATED APPLICATIONS

This application claims the priority benefit of U.S. Provisional Application Nos. 62/860,598, filed on Jun. 12, 2019, and 62/839,974, filed on Apr. 29, 2019, each of which is incorporated by reference herein in its entirety

REFERENCE TO SEQUENCE LISTING SUBMITTED ELECTRONICALLY VIA EFS-WEB

The content of the electronically submitted sequence listing (Name: 2921_1060002_SL_ST25; Size: 15,691 bytes and Date of Creation: Apr. 28, 2020) is incorporated herein by reference in its entirety.

FIELD OF THE INVENTION

The field of the invention generally relates to combinations of an anti-CD123 immunoconjugate with a hypomethylating agent (HMA) and/or a B-cell leukemia/lymphoma-2 (BCL-2) antagonist as the use of the combinations in the treatment of hematologic malignancies.

BACKGROUND

Cancer is one of the leading causes of death in the developed world, with over one million people diagnosed with cancer and 500,000 deaths per year in the United States alone. Overall it is estimated that more than 1 in 3 people will develop some form of cancer during their lifetime.

CD123 is the alpha-subunit of the interleukin-3 receptor (IL-3Rα). CD123 expression is low on normal hematopoietic stem cells (Testa et al., *Biomark Res.,* 10; 2(1):4. (2014), Jordan et al., *Leukemia,* 14(10):1777-84 (2000)). However, CD123 is overexpressed in multiple hematological malignancies of both myeloid and lymphoid origins, including acute myeloid leukemia (AML), myelodysplastic syndrome (MDS), B-cell acute lymphoblastic leukemia (B-ALL), chronic myeloid leukemia in blast crisis/phase (BP-CML), and blastic plasmacytoid dendritic cell neoplasm (BPDCN) (Testa 2014). Interleukin-3 is produced by activated T-lymphocytes. IL-3 together with other growth factors stimulates the development and mediates the survival of a wide range of hematopoietic cells in bone marrow (Testa 2014). CD levels on normal hematopoietic stem cells are very low, but early common myeloid progenitors express higher CD123 levels (Testa 2014, Jordan 2000). Medium to high expression of CD123 on normal tissues is limited to rare populations of white blood cells, such as plasmacytoid dendritic cells and basophils (Jordan 2000, Testa 2014).

Acute myeloid leukemia is the most common form of acute leukemia among adults and accounts for the largest number of deaths from leukemias in the United States. In 2017, an estimated 21,380 people will be diagnosed with AML per year and 10,590 patients will die of the disease (Siegel et al., *CA Cancer J Clin.* 2017; 67(1):7-30 (2017)). The median age of diagnosis is 66 years. Frontline chemotherapy in AML is reported to induce complete response (CR) in 70%-80% of patients who are 60 years of age or younger and in approximately 50% of older patients. "Fit" patients are judged to be able to tolerate intensive treatment, are often younger (<60 years), and typically receive one to two cycles of induction with "7+3," a combination of cytarabine and anthracycline, typically daunorubicin. Following this, these fit patients may receive high-dose cytarabine for one or more cycles and may receive a stem cell transplant. Standard induction and post-induction therapies result in a median duration of remission of approximately one year and potential cures in 25%-35% of the patients. "Unfit" patients, often older, typically receive venetoclax, azacitidine, a hypomethylating agent. The majority of AML patients will eventually relapse, and AML salvage regimens offer poor outcomes with significant toxicity. Thus, novel therapies with limited toxicity in this relapsed population are needed.

Blastic plasmacytoid dendritic cell neoplasm is a rare, aggressive hematologic malignancy derived from myeloid dendritic cell precursors, which often manifests with skin lesions in addition to lymph node, blood, and bone marrow involvement. Characterized by CD4, CD56, and CD123 expression among other markers, BPDCN blasts express high levels of CD123. Unfortunately, there is no standard of care for BPDCN, with both acute lymphoblastic leukemia (ALL) and AML regimens used in frontline treatment. Despite CR rates of 47%-86% in frontline disease, median overall survival is approximately 12-16 months. The majority of BPDCN patients will eventually relapse with no standard treatment options.

Acute lymphoblastic leukemia is a rare, aggressive hematologic malignancy derived from lymphoid precursors, which often manifests with lymph node, blood, and bone marrow involvement. B-cell acute lymphoblastic leukemia and some T-cell acute lymphoblastic leukemia blasts express CD123 at levels similar to AML blasts. Although initial remission rates are high, long-term survival rates are 35%-40% in patients less than 60 years of age, and less than 10% for older patients (Goldstone 2008). Patients with relapsed ALL have several chemotherapeutic options, as well as immunotherapy with United States Food and Drug Administration-approved anti-CD19 bispecific blinatumomab. However, long-term survival remains poor for these patients.

Given the inability of currently available therapeutics to treat many hematological malignancies, there is a need for more effective interventions.

BRIEF SUMMARY OF THE INVENTION

Combinations of an anti-CD123 immunoconjugate (e.g. IMGN632) with a BCL-2 inhibitor and/or hypomethylating agent are provided herein. Also provided herein are methods of treating a patient with cancer using such a combination In certain instances, a method for treating a hematologic malignancy in a subject comprises administering to the subject in need thereof an immunoconjugate that binds to CD123, wherein the immunoconjugate comprises an antibody or antigen-binding fragment thereof comprising a heavy chain variable region CDR1 comprising the amino acid sequence of SEQ ID NO: 5; a heavy chain variable region CDR2 comprising the amino acid sequence of SEQ ID NO: 6; and a heavy chain variable region CDR3 comprising the amino acid sequence of SEQ ID NO: 7; and a light chain variable region CDR1 comprising the amino acid sequence of SEQ ID NO: 8; a light chain variable region CDR2 comprising the amino acid sequence of SEQ ID NO: 9; and a light chain variable region CDR3 comprising the amino acid sequence of: SEQ ID NO: 10, and a BCL-2 inhibitor, a hypomethylating agent, or a combination thereof. In certain instances, the immunoconjugate is administered in combination with the BCL-2 inhibitor. In certain instances, the immunoconjugate is administered in combination with the hypomethylating agent. In certain instances, the immunoconjugate is administered in combination with the BCL-2 inhibitor and the hypomethylating agent.

In certain instances, the antibody or antigen-binding fragment thereof comprises a VH comprising the amino acid sequence set forth in SEQ ID NO:1 and/or a VL comprising the amino acid sequence set forth in SEQ ID NO: 2. In certain instances, the antibody or antigen-binding fragment comprises a heavy chain constant region and/or a light chain constant region. In certain instances, the antibody or antigen-binding fragment comprises a heavy chain comprising the amino acid sequence set forth in SEQ ID NO:3 and/or a light chain comprising the amino acid sequence set forth in SEQ ID NO:4.

In certain instances, the immunoconjugate comprises a cytotoxin. In certain instances, the cytotoxin is a DNA-alkylating agent. In certain instances, the DNA-alkylating agent is indolino-benzodiazepine (IGN) DNA-alkylator. In certain instances, the immunoconjugate comprises a peptide linker. In certain instances, the immunoconjugate is IMGN632. In certain instances, the immunoconjugate is administered in a pharmaceutical composition comprising immunoconjugates with the following structure immunoconjugate is administered at a dose of about 0.015 mg/kg to about 0.09 mg/kg once in the 21-day cycle. In certain instances, the immunoconjugate is administered at a dose of about 0.015 mg/kg to about 0.135 mg/kg once in the 21-day cycle. In certain instances, the dose is about 0.015 mg/kg, about 0.045 mg/kg, or about 0.09 mg/kg. In certain instances, the dose is about 0.015 mg/kg, about 0.045 mg/kg, or about 0.135 mg/kg. In certain instances, the dose is about 0.045 mg/kg. In certain instances, the dose is about 0.03 mg/kg.

In certain instances, the immunoconjugate is administered three times in a 21-day cycle. In certain instances, the total amount of immunoconjugate administered in the 21-day cycle is about 0.045 mg/kg, about 0.09 mg/kg, or about 0.18 mg/kg. In certain instances, the total amount of immunoconjugate administered in the 21-day cycle is about 0.135 mg/kg. In certain instances, about 0.015 mg/kg to about 0.06 mg/kg of the immunoconjugate is administered at each of the three times in the 21-day cycle. In certain instances, about 0.015 mg/kg, about 0.03 mg/kg, or about 0.06 mg/kg is administered at each of the three times in the 21-day cycle. In certain instances, about 0.045 mg/kg is administered at each of the three times in the 21-day cycle. In certain instances, the first administration of the immunoconjugate is on day 7 of the 21-day cycle. In certain instances, the second

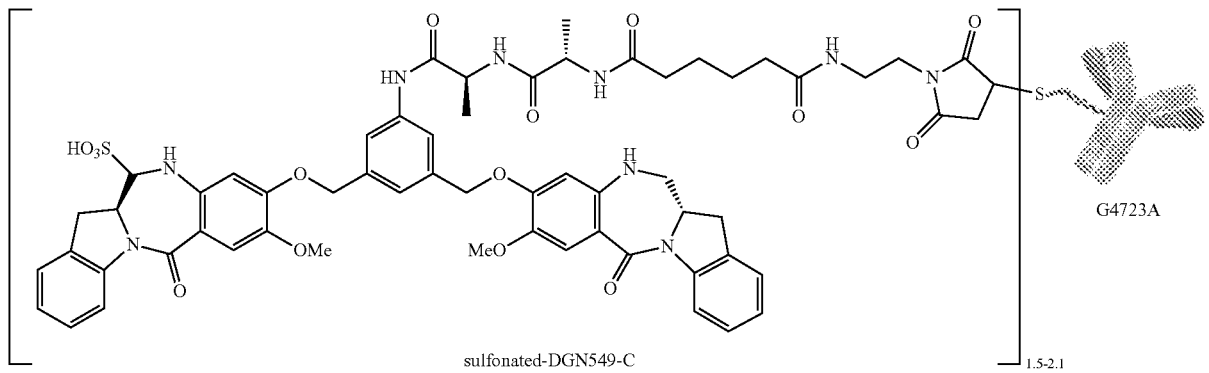

wherein G4723A comprises a heavy chain comprising the amino acid sequence set forth in SEQ ID NO:3 and a light chain comprising the amino acid sequence set forth in SEQ ID NO:4.

In certain instances, the administration is a front-line therapy. In certain instances, the immunoconjugate is administered intravenously.

In certain instances, administration of the immunoconjugate with the BCL-2 inhibitor, the hypomethylating agent, or a combination thereof produces a synergistic effect. In certain instances, administration of the immunoconjugate and the BCL-2 inhibitor does not produce more toxicity than administration of the immunoconjugate alone or the BCL-2 inhibitor alone. In certain instances, administration of the immunoconjugate and the hypomethylating agent does not produce more toxicity than administration of the immunoconjugate alone or the hypomethylating agent alone. In certain instances, administration of the immunoconjugate, the BCL-2 inhibitor, and the hypomethylating agent does not produce more toxicity than the administration of the immunoconjugate, the BCL-2 inhibitor, and/or the hypomethylating agent.

In certain instances, the the immunoconjugate is administered once in a 21-day cycle. In certain instances, the administration of the immunoconjugate is on day 10 of the 21-day cycle. In certain instances, the third administration is on day 14 of the 21-day cycle. In certain instances, the first, second, and third administrations are on day 7, day 10, and day 14, respectively of the 21-day cycle.

In certain instances, the BCL-2 inhibitor is venetoclax. In certain instances, the BCL-2 inhibitor is administered at a dose of 400 mg. In certain instances, the BCL-2 inhibitor is venetoclax. In certain instances, the BCL-2 inhibitor is administered at a dose of 200 mg.

In certain instances, the BCL-2 inhibitor is administered daily in a 21-day cycle. In certain instances, the BCL-2 inhibitor is administered at a dose of 100 mg on day 1 of a 21-day cycle, at a dose of 200 mg on day 2 of the 21-day cycle, and at a dose of 400 mg on days 3-21 of the 21-day cycle. In certain instances, the BCL-2 inhibitor is administered at a dose of 100 mg on day 1 of a 21-day cycle, at a dose of 200 mg on day 2 of the 21-day cycle, and a dose of 400 mg on days 3-7 or days 3-14 of the 21-day cycle. In certain instances, the BCL-2 inhibitor is administered at a dose of 100 mg on day 1 of the 21-day cycle, and at a dose of 200 mg on days 2-21, 2-14, or 2-7 of the 21-day cycle. In certain instances, the BCL-2 inhibitor is administered on days 1-7 of the 21-day cycle. In certain instances, the BCL-2 inhibitor is administered on days 1-8 of the 21-day cycle. In certain instances, the BCL-2 inhibitor is administered on days 1-14 of the 21-day cycle. In certain instances, the BCL-2 inhibitor is administered on days 1-18 of the 21-day cycle. In certain instances, the BCL-2 inhibitor is administered on days 1-21 of the 21-day cycle. In certain instances, the BCL-2 inhibitor is administered orally.

In certain instances, administration of the immunoconjugate is initiated six days after initiation of the administration of the BCL-2 inhibitor.

In certain instances, the immunoconjugate is administered once in a 28-day cycle. In certain instances, the immunoconjugate is administered at a dose of about 0.015 mg/kg to about 0.09 mg/kg once in the 28-day cycle. In certain instances, the immunoconjugate is administered at a dose of about 0.015 mg/kg to about 0.135 mg/kg once in the 28-day cycle. In certain instances the dose is about 0.015 mg/kg, about 0.045 mg/kg, or about 0.09 mg/kg. In certain instances the dose is about 0.015 mg/kg, about 0.045 mg/kg, or about 0.135 mg/kg. In certain instances, the dose is about 0.045 mg/kg. In certain instances, the dose is about 0.03 mg/kg.

In certain instances, the immunoconjugate is administered three times in a 28-day cycle. In certain instances, the total amount of immunoconjugate administered in the 28-day cycle is about 0.045 mg/kg, about 0.09 mg/kg, or about 0.18 mg/kg. In certain instances, the total amount of immunoconjugate administered in the 28-day cycle is about 0.135 mg/kg. In certain instances, about 0.015 mg/kg to about 0.06 mg/kg of the immunoconjugate is administered at each of the three times in the 28-day cycle. In certain instances, about 0.015 mg/kg, about 0.03 mg/kg, or about 0.06 mg/kg of the immunoconjugate is administered at each of the three times in the 28-day cycle. In certain instances, about 0.135 mg/kg of the immunoconjugate is administered at each of the three times in the 28-day cycle. In certain instances, the first administration of the immunoconjugate is on day 7 of the 28-day cycle. In certain instances, the second administration of the immunoconjugate is on day 10 of the 28-day cycle. In certain instances, the third administration of the immunoconjugate is on day 14 of the 28-day cycle. In certain instances, the first, second, and third administrations of the immunoconjugate are on day 7, day 10, and day 14, respectively of the 28-day cycle.

In certain instances, the BCL-2 inhibitor is venetoclax. In certain instances, the BCL-2 inhibitor is administered at a dose of 400 mg. In certain instances, the BCL-2 inhibitor is administered at a dose of 200 mg.

In certain instances, the BCL-2 inhibitor is administered daily in a 28-day cycle. In certain instances, the BCL-2 inhibitor is administered at a dose of 100 mg on day 1 of a 28-day cycle, at a dose of 200 mg on day 2 of the 28-day cycle, and at a dose of 400 mg on days 3-28 of the 28-day cycle. In certain instances, the BCL-2 inhibitor is administered at a dose of 100 mg on day 1 of a 28-day cycle, at a dose of 200 mg on day 2 of the 28-day cycle, and a dose of 400 mg on days 3-7 or days 3-14 of the 28-day cycle. In certain instances, the BCL-2 inhibitor is administered at a dose of 100 mg on day 1 of the 28-day cycle, and at a dose of 200 mg on days 2-28, 2-14, or 2-7 of the 28-day cycle. In certain instances, the BCL-2 inhibitor is administered on days 1-7 of the 28-day cycle. In certain instances, the BCL-2 inhibitor is administered on days 1-8 of the 28-day cycle. In certain instances, the BCL-2 inhibitor is administered on days 1-14 of the 28-day cycle. In certain instances, the BCL-2 inhibitor is administered on days 1-18 of the 28-day cycle. In certain instances, the BCL-2 inhibitor is administered on days 1-21 of the 28-day cycle. In certain instances, the BCL-2 inhibitor is administered on days 1-28 of the 21-day cycle.

In certain instances, the BCL-2 inhibitor is administered orally. In certain instances, administration of the immunoconjugate is initiated six days after initiation of the administration of the BCL-2 inhibitor.

In certain instances, the hypomethylating agent is azacitidine. In certain instances, the azacitidine is administered in a 28-day cycle. In certain instances, the azacitidine is administered once daily on days 1-7 of a 28-day cycle. In certain instances, the azacitidine is administered once daily on days 3-7 of a 28-day cycle. In certain instances, the azacitidine is administered once daily on days 1-5 of a 28-day cycle. In certain instances, the azacitidine is administered at a dose of about 75 mg/m$^2$. In certain instances, the azacitidine is administered subcutaneously. In certain instances, the azacitidine is administered intravenously.

In certain instances, the hypomethylating agent is decitabine. In certain instances, the decitabine is administered intravenously.

In certain instances, the hematological malignancy is present in the subject as minimal residual disease (MRD).

In certain instances, a method for treating a hematologic malignancy present as a minimal residual disease in a human subject comprises administering to the subject an anti-CD123 immunoconjugate comprising an anti-CD123 antibody or antigen-binding fragment thereof linked to a cytotoxic agent. In certain instances, the immunoconjugate is administered at a dose of about 0.045 mg/kg to about 0.18 mg/kg. In certain instances, about 0.045 mg/kg, about 0.09 mg/kg, about 0.135 mg/kg, or about 0.18 mg/kg is administered to the subject. In certain instances, about 0.045 mg/kg is administered to the subject. In certain instances, about 0.03 mg/kg is administered to the subject. In certain instances, the immunoconjugate is administered intravenously. In certain instances, the hematologic malignancy is a leukemia. In certain instances, the immunoconjugate is administered to the subject once in a 21-day cycle.

In certain instances, the administration is for one cycle. In certain instances, the administration is for more than one cycle. In certain instance, the administration is for at least 2 cycles, at least 3 cycles, at least 4 cycles, at least 5 cycles, at least 6 cycles, at least 7 cycles, at least 8 cycles, at least 9 cycles, or at least 10 cycles. In certain instances, the administration is for about 2-4 cycles, about 2-6 cycles, about 2-8 cycles, about 2-10 cycles, or about 2-12 cycles.

In certain instances, the method further comprises administering a reduced dose of the immunoconjugate after a dose-limiting toxicity has occurred in the subject and has been reduced to baseline or ≤Grade 2.

In certain instances, the immunoconjugate is further administered as a maintenance therapy.

In certain instances, the maintenance therapy comprises administering the immunoconjugate once in a 21-day cycle. In certain instances, the maintenance therapy comprises administering the immunoconjugate at a dose of about 0.015 mg/kg to about 0.09 mg/kg once in the 21-day cycle. In certain instances, the maintenance therapy comprises administering the immunoconjugate at a dose of about 0.015 mg/kg to about 0.135 mg/kg once in the 21-day cycle. In certain instances, the maintenance therapy comprises administering the immunoconjugate at a dose of 0.015 mg/kg once in the 21-day cycle. In certain instances, the maintenance therapy comprises administering the immunoconjugate at a dose of about 0.045 mg/kg once in the 21-day cycle. In certain instances, the maintenance therapy comprises administering the immunoconjugate at a dose of about 0.03 mg/kg once in the 21-day cycle. In certain instances, the maintenance therapy comprises administering the immunoconjugate at a dose of about 0.09 mg/kg once in the 21-day cycle. In certain instances, the maintenance therapy comprises administering the immunoconjugate at a dose of about 0.135 mg/kg once in the 21-day cycle In certain instances, the maintenance therapy comprises administering the immunoconjugate three times in a 21-day cycle. In certain instances, during the maintenance therapy, the total amount of immunoconjugate administered in the 21-day cycle is about 0.045 mg/kg, about 0.09 mg/kg, or about 0.18 mg/kg. In certain instances, during the maintenance therapy, the total amount of immunoconjugate administered in the 21-day cycle is about 0.135 mg/kg. In certain instances, during the maintenance therapy about 0.015 mg/kg to about 0.06 mg/kg of the immunoconjugate is administered at each of the three times in the 21-day cycle. In certain instances, during the maintenance therapy about 0.015 mg/kg of the immunoconjugate is administered at each of the three times in the 21-day cycle. In certain instances, during the maintenance therapy about 0.03 mg/kg of the immunoconjugate is administered at each of the three times in the 21-day cycle. In certain instances, during the maintenance therapy about 0.045 mg/kg of the immunoconjugate is administered at each of the three times in the 21-day cycle. In certain instances, during the maintenance therapy about 0.06 mg/kg of the immunoconjugate is administered at each of the three times in the 21-day cycle.

In certain instances, the hematological malignancy is a relapsed hematological malignancy. In certain instances, the hematological malignancy is a refactory hematological malignancy. In certain instances, the hematological malignancy is acute myeloid leukemia (AML), myelodysplastic syndrome (MDS), B-cell acute lymphoblastic leukemia (B-ALL), chronic myeloid leukemia in blast crisis/phase (BP-CML), and blastic plasmacytoid dendritic cell neoplasm (BPDCN). In certain instances, the hematological malignancy is AML. In certain instances, the AML is relapsed AML. In certain instances, the AML is refractory AML. In certain instances, the hematological malignancy is BPDCN. In certain instances, the BPDCN is relapsed BPDCN. In certain instances, the BPDCN is relapsed BPDCN. In certain instances, the hematological malignancy is ALL. In certain instances, the ALL is relapsed ALL. In certain instances, the ALL is refractory ALL. In certain instances, the hematological malignancy is chronic myelomonocytic leukemia (CMML). In certain instances, the CMML is relapsed CMML. In certain instances, the CMML is refractory CMML. In certain instances, the hematological malignancy is myelofibrosis (MF). In certain instances, the MF is relapsed MF. In certain instances, the MF is refractory MF. In certain instances, the hematological malignancy is myelodysplastic syndrome (MDS). In certain instances, the MDS is relapsed MDS. In certain instances, the MDS is refractory MDS.

In certain instances, the hematological malignancy is a CD123-expressing hematological malignancy. In certain instances, CD123 has been detected in a sample obtained from the hematological malignancy prior to the administration. In certain instances, the CD123 was detected using flow cytometry. In certain instances, the method further comprises detecting CD123 in a sample obtained from the hematological malignancy prior to the administration. In certain instances, at least 80% of cells in the hematological malignancy express CD123. In certain instances, CD123 has been detected in at least 80% of cells in a sample obtained from the hematological malignancy prior to the administration. In certain instances, the method further comprises detecting CD123 in at least 80% of cells in a sample obtained from the hematological malignancy prior to the administration.

In certain instances, the hematological malignancy is resistant to IMGN632.

In certain instances, the hematological malignancy expresses multidrug resistance 1 (MDR1). In certain instances, the hematological malignancy expresses P-glycoprotein (P-gp). In certain instances, the subject has an absolute neutrophil count of greater than 500 neutrophils/µL.

In certain instances, the subject received at least one prior line of therapy. In certain instances, the subject received at least two prior lines of therapy. In certain instances, the subject received at least three prior lines of therapy. In certain instances, the cancer has previously been treated with venetoclax. In certain instances, the cancer has not previously been treated with venetoclax. In certain instances, has previously been treated with a hyomethylating agent. In certain instances, the cancer has not previously been treated with a hypomethylating agent.

In certain instances, the subject has been pretreated with a corticosteroid prior to administration of the immunoconjugate. In some instances, the method further comprises pre-treating the subject with a corticosteroid prior to administration of the immunoconjugate. In certain instances, the corticosteroid is diphenhydramine, acetaminophen, paracetamol, dexamethasone, or a combination thereof.

In certain instances, the immunoconjugate and the BCL-2 inhibitor, the hypomethylating agent, or combination thereof are administered in separate pharmaceutical compositions.

In certain instances, the immunoconjugate and the BCL-2 inhibitor, the hypomethylating agent, or combination thereof are administered in separate pharmaceutical compositions.

In certain instances, the subject is human.

In certain instances, a method for treating a hematologic malignancy in a human subject comprises administering to the subject in need thereof IMGN632 and venetoclax in a 21-day cycle, wherein the IMGN632 is administered intravenously on day 7 of the cycle at a dose of about 0.015 mg/kg to about 0.09 mg/kg, (optionally wherein the dose is about 0.015 mg/kg, about 0.045 mg/kg, or about 0.09 mg/kg), and wherein the venetoclax is administered orally at a dose of 100 mg on day 1 of the cycle, at a dose of 200 mg on day 2 of the cycle, and at a dose of 400 mg on days 3-21 of the cycle.

In certain instances, a method for treating a hematologic malignancy in a human subject comprises administering to the subject in need thereof IMGN632 and venetoclax in a 21-day cycle, wherein the IMGN632 is administered intravenously on day 7 of the cycle at a dose of about 0.015 mg/kg to about 0.135 mg/kg, (optionally wherein the dose is about 0.135 mg/kg), and wherein the venetoclax is administered orally at a dose of 100 mg on day 1 of the cycle, at a dose of 200 mg on day 2 of the cycle, and at a dose of 400 mg on days 3-21 of the cycle.

In certain instances, a method for treating a hematologic malignancy in a human subject comprises administering to the subject in need thereof IMGN632 and venetoclax in a 21-day cycle, wherein the IMGN632 is administered intravenously on day 7 of the cycle at a dose of about 0.015 mg/kg to about 0.09 mg/kg (optionally wherein the dose is about 0.015 mg/kg, about 0.045 mg/kg, or about 0.09 mg/kg), and wherein the venetoclax is administered at an oral daily dose of 400 mg.

In certain instances, a method for treating a hematologic malignancy in a human subject comprises administering to the subject in need thereof IMGN632 and venetoclax in a 21-day cycle, wherein the IMGN632 is administered intravenously on day 7 of the cycle at a dose of about 0.015 mg/kg to about 0.09 mg/kg, and wherein the venetoclax is administered at an oral daily dose of 400 mg. In certain instances, the veneoclax is administered on days 1-7 of the 21-day cycle. In certain instances, the veneoclax is administered on days 1-8 of the 21-day cycle. In certain instances, the veneoclax is administered on days 1-14 of the 21-day cycle. In certain instances, the veneoclax is administered on days 1-18 of the 21-day cycle. In certain instances, the veneoclax is administered on days 1-21 of the 21-day cycle. In certain instance, IMGN632 is administered at a dose of about 0.045 mg/kg. In certain instance, IMGN632 is administered at a dose of about 0.03 mg/kg. In certain instance, IMGN632 is administered at a dose of about 0.015 mg/kg.

In certain instances, a method for treating a hematologic malignancy in a human subject comprises administering to the subject in need thereof IMGN632 and venetoclax in a 21-day cycle, wherein the IMGN632 is administered intravenously on day 7 of the cycle at a dose of about 0.015 mg/kg to about 0.135 mg/kg (optionally wherein the dose is about 0.135 mg/kg), and wherein the venetoclax is administered at an oral daily dose of 400 mg.

In certain instances, a method for treating a hematologic malignancy in a human subject comprises administering to the subject in need thereof IMGN632 and venetoclax in a 21-day cycle, wherein the IMGN632 is administered intravenously on days 7, 10, and 14 of the cycle at a dose of about 0.015 mg/kg to about 0.06 mg/kg (optionally wherein the dose is about 0.015 mg/kg, about 0.03 mg/kg, or about 0.06 mg/kg), and wherein the venetoclax is administered orally at a dose of 100 mg on day 1 of the cycle, at a dose of 200 mg on day 2 of the cycle, and at a dose of 400 mg on days 3-21 of the cycle.

In certain instances, a method for treating a hematologic malignancy in a human subject comprises administering to the subject in need thereof IMGN632 and venetoclax in a 21-day cycle, wherein the IMGN632 is administered intravenously on days 7, 10, and 14 of the cycle at a dose of about 0.015 mg/kg to about 0.06 mg/kg (optionally wherein the dose is about 0.015 mg/kg, about 0.03 mg/kg, or about 0.06 mg/kg), and wherein the venetoclax is administered at an oral daily dose of 400 mg.

In certain instances, a method for treating a hematologic malignancy in a human subject comprises administering to the subject in need thereof IMGN632 and azacitidine in a 28-day cycle wherein the IMGN632 is administered intravenously on day 7 of the cycle at a dose of about 0.015 mg/kg to about 0.09 mg/kg, optionally wherein the dose is about 0.015 mg/kg, about 0.045 mg/kg, or about 0.09 mg/kg, and wherein the azacitdine is administered subcutaneously or intravenously at a dose of 75 mg/m$^2$ on days 1-7 of the cycle.

In certain instances, a method for treating a hematologic malignancy in a human subject comprises administering to the subject in need thereof IMGN632 and azacitidine in a 28-day cycle wherein the IMGN632 is administered intravenously on day 7 of the cycle at a dose of about 0.015 mg/kg to about 0.09 mg/kg, optionally wherein the dose is about 0.015 mg/kg, about 0.03 mg/kg, about 0.045 mg/kg, or about 0.09 mg/kg, and wherein the azacitdine is administered subcutaneously or intravenously at a dose of 75 mg/m$^2$. In certain instance, azacitdine is administered on days 1-7 of the cycle. In certain instance, azacitdine is administered on days 1-5 of the cycle. In certain instance, IMGN632 is administered at a dose of about 0.045 mg/kg. In certain instance, IMGN632 is administered at a dose of about 0.03 mg/kg In certain instances, a method for treating a hematologic malignancy in a human subject comprises administering to the subject in need thereof IMGN632 and azacitidine in a 28-day cycle wherein the IMGN632 is administered intravenously on day 7 of the cycle at a dose of about 0.015 mg/kg to about 0.135 mg/kg, optionally wherein the dose is about 0.135 mg/kg, and wherein the azacitdine is administered subcutaneously or intravenously at a dose of 75 mg/m$^2$ on days 1-7 of the cycle.

In certain instances, a method for treating a hematologic malignancy in a human subject comprises administering to the subject in need thereof IMGN632 and azacitidine in a 28-day cycle wherein the IMGN632 is administered intravenously on days 7, 10, and 14 of the cycle at a dose of about 0.015 mg/kg to about 0.06 mg/kg, optionally wherein the dose is about 0.015 mg/kg, about 0.03 mg/kg, or about 0.06 mg/kg, and wherein the azacitdine is administered subcutaneously or intravenously at a dose of 75 mg/m$^2$ on days 1-7 of the cycle.

In certain instances, a method for treating a hematologic malignancy in a human subject comprises administering to the subject in need thereof IMGN632 and azacitidine in a 28-day cycle wherein the IMGN632 is administered intravenously on days 7, 10, and 14 of the cycle at a dose of about 0.015 mg/kg to about 0.06 mg/kg, and wherein the azacitdine is administered subcutaneously or intravenously at a dose of 75 mg/m$^2$. In certain instance, azacitdine is administered on days 1-7 of the cycle. In certain instance, azacitdine is administered on days 1-5 of the cycle. In certain instance, IMGN632 is administered at a dose of about 0.045 mg/kg. In certain instance, IMGN632 is administered at a dose of about 0.03 mg/kg.

In certain instances, the method further comprises administering venetoclax. In certain instances, the veneoclax is administered on days 1-7 of the 28-day cycle. In certain instances, the veneoclax is administered on days 1-8 of the 28-day cycle. In certain instances, the veneoclax is administered on days 1-14 of the 28-day cycle. In certain instances, the veneoclax is administered on days 1-18 of the 28-day cycle. In certain instances, the veneoclax is administered on days 1-21 of the 28-day cycle. In certain instances, the veneoclax is administered on days 1-28 of the 28-day cycle.

In certain instances, the method further comprises administering venetoclax orally at a dose of 100 mg on day 1 of the cycle, at a dose of 200 mg on day 2 of the cycle, and at a dose of 400 mg on days 3-28 of the cycle. In certain instances, the method further comprises administering venetoclax at an oral daily dose of 400 mg.

In certain instances, the hematologic malignancy is AML. In certain instances, the hematologic malignancy is BPDCN. In certain instances, the hematologic malignancy is ALL. In certain instances, the hematologic malignancy is chronic myelomonocytic leukemia (CMML). In certain instances, the hematologic malignancy is myelofibrosis (MF). In certain instances, the hematologic malignancy is myelodysplastic syndrome (MDS).

DETAILED DESCRIPTION OF THE INVENTION

Figure 1A:
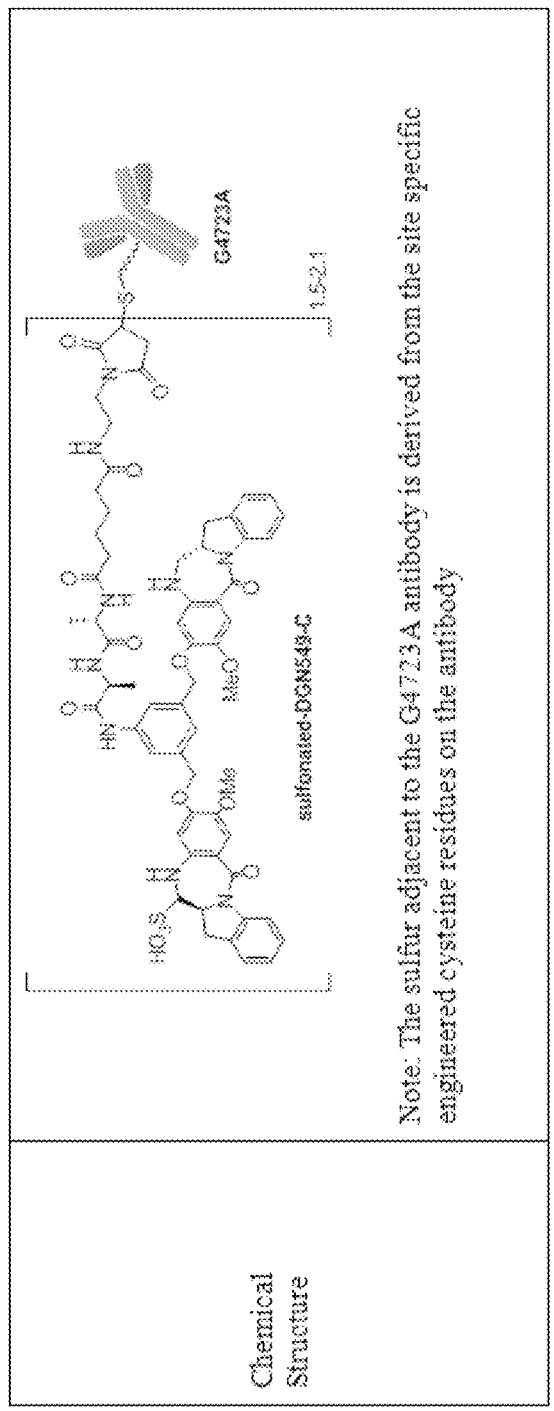
FIG. 1A shows the chemical structure for IMGN632. IMGN632 is composition comprising immunoconjugates containing the anti-CD123 G4723A antibody linked to the cytotoxic payload DGN549-C in sodium bisulfate. The majority of the immunoconjugate in the composition is in the sulfonated version shown in FIG. 1A.

The present invention provides combinations of an anti-CD123 immunoconjugate with a hypomethylating agent (HMA) and/or a B-cell leukemia/lymphoma-2 (BCL-2) antagonist and the use of the combinations in the treatment of hematologic malignancies. The present invention also provides anti-CD123 immunoconjugates (optionally in combination with a HMA and/or a BCL-2 antagonist) for the treatment of hematologic malignancies present as minimal residual disease.

I. Definitions

To facilitate an understanding of the present invention, a number of terms and phrases are defined below.

The terms "IL-3Rα," "Interleukine-3 Receptor alpha," and "CD123," as used interchangeably herein, refer to mammalian CD123 polypeptides, including, but not limited to, native CD123 polypeptides and isoforms of CD123 polypeptides, unless otherwise indicated. The terms encompass "full-length," unprocessed CD123 polypeptides as well as any form of CD123 polypeptide that results from processing within the cell. The term also encompasses naturally occurring variants of CD123, e.g., those encoded by splice variants and allelic variants. The CD123 polypeptides described herein can be isolated from a variety of sources, such as from human tissue types or from another source, or prepared by recombinant or synthetic methods. Where specifically indicated, "CD123" can be used to refer to a nucleic acid that encodes a CD123 polypeptide. Human CD123 sequences are known and include, for example, those sequences associated with NCBI reference numbers NP_002174 & NM_002183 (protein and nucleic acid sequences for human CD123 variant 1), and NP_001254642 & NM_001267713 (protein and nucleic acid sequences for human CD123 variant 2). As used herein, the term "human CD123" refers to CD123 comprising the sequence of SEQ ID NO:11 or SEQ ID NO:12.

```
                                              (SEQ ID NO: 11)
MVLLWLTLLL  IALPCLLQTK  EDPNPPITNL  RMKAKAQQLT

WDLNRNVTDI  ECVKDADYSM  PAVNNSYCQF  GAISLCEVTN

YTVRVANPPF  STWILFPENS  GKPWAGAENL  TCWIHDVDFL

SCSWAVGPGA  PADVQYDLYL  NVANRRQQYE  CLHYKTDAQG

TRIGCRFDDI  SRLSSGSQSS  HILVRGRSAA  FGIPCTDKFV

VFSQIEILTP  PNMTAKCNKT  HSFMHWKMRS  HFNRKFRYEL

QIQKRMQPVI  TEQVRDRTSF  QLLNPGTYTV  QIRARERVYE

FLSAWSTPQR  FECDQEEGAN  TRAWRTSLLI  ALGTLLALVC

VFVICRRYLV  MQRLFPRIPH  MKDPIGDSFQ  NDKLVVWEAG

KAGLEECLVT  EVQVVQKT (SEQ ID NO: 12)
MVLLWLTLLL  IALPCLLQTK  EGGKPWAGAE  NLTCWIHDVD

FLSCSWAVGP  GAPADVQYDL  YLNVANRRQQ  YECLHYKTDA

QGTRIGCRFD  DISRLSSGSQ  SSHILVRGRS  AAFGIPCTDK

FVVFSQIEIL  TPPNMTAKCN  KTHSFMHWKM  RSHFNRKFRY

ELQIQKRMQP  VITEQVRDRT  SFQLLNPGTY  TVQIRARERV

YEFLSAWSTP  QRFECDQEEG  ANTRAWRTSL  LIALGTLLAL

VCVFVICRRY  LVMQRLFPRI  PHMKDPIGDS  FQNDKLVVWE

AGKAGLEECL  VTEVQVVQKT
```

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, chimeric antibodies, humanized antibodies, human antibodies, fusion proteins comprising an antibody, and any other modified immunoglobulin molecule so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

The term "anti-CD123 antibody" or "an antibody that binds to CD123" refers to an antibody that is capable of binding CD123 with sufficient affinity such that the antibody is useful as a diagnostic and/or therapeutic agent in targeting CD123 (e.g., the antibody in IMGN632). The extent of binding of an anti-CD123 antibody to an unrelated, non-CD123 protein can be less than about 10% of the binding of the antibody to CD123 measured, e.g., by a radioimmunoassay (RIA).

The term "antibody fragment" refers to a portion of an intact antibody with a sufficient positive charge to bind to a cation exchange resin. An "antigen-binding fragment" refers to a portion of an intact antibody that binds to an antigen and has a sufficient positive charge to bind to a cation exchange resin. An antigen-binding fragment can contain the antigenic determining variable regions of an intact antibody. Examples of antibody fragments include, but are not limited to Fab, Fab', F(ab')2, and Fv fragments, linear antibodies, and single chain antibodies.

The term "cysteine engineered" antibody or antigen-binding fragment thereof includes an antibody or antigen-binding fragment thereof with at least one cysteine ("Cys") that is not normally present at a given residue of the antibody or antigen-binding fragment thereof light chain or heavy chain. Such Cys, which may also be referred to as "engineered Cys," can be engineered using any conventional molecular biology or recombinant technology (e.g., by replacing the coding sequence for a non-Cys residue at the target residue with a coding sequence for Cys). For example, if the original residue is Ser with a coding sequence of 5'-UCU-3', the coding sequence can be mutated (e.g., by site-directed mutagenesis) to 5'-UGU-3', which encodes Cys. In certain embodiments, the Cys engineered antibody or antigen-binding fragment thereof has an engineered Cys in the heavy chain. In certain embodiments, the engineered Cys is in or near the CH3 domain of the heavy chain. In certain embodiments, the engineered Cys is at residue 442 of the heavy chain (EU/OU numbering; EU index, Kabat et al, Sequences of Proteins of Immunological Interest, 5th Ed., NIH publication No. 91-3242, 1991, the entire contents of which are incorporated herein by reference). In certain embodiments, the Fc region comprises a cysteine at one or more of positions 239, 282, 289, 297, 312, 324, 330, 335, 337, 339, 356, 359, 361, 383, 384, 398, 400, 440, 422, and 442, as numbered by the EU index. In certain embodiments, any one or more of the following residues may be substituted with cysteine: V205 (Kabat numbering) of the light chain; A118 (EU numbering) of the heavy chain; and S400 (EU numbering) of the heavy chain Fc region. In certain embodiments, the variable light chain domain, e.g., of an scFv, has a cysteine at Kabat position 100. In certain embodiments, the variable heavy chain domain, e.g. of an scFv, has a cysteine at Kabat position 44. Cysteine engineered antibodies may be generated as described, e.g., in U.S. Pat. Nos. 7,521,541, 7,855,275, U.S. Published Application No. 20110033378 and WO 2011/005481.

A "monoclonal" antibody or antigen-binding fragment thereof refers to a homogeneous antibody or antigen-binding fragment population involved in the highly specific recognition and binding of a single antigenic determinant, or epitope. This is in contrast to polyclonal antibodies that typically include different antibodies directed against different antigenic determinants. The term "monoclonal" antibody or antigen-binding fragment thereof encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal" antibody or antigen-binding fragment thereof refers to such antibodies and antigen-binding fragments thereof made in any number of manners including but not limited to by hybridoma, phage selection, recombinant expression, and transgenic animals.

The term "humanized" antibody or antigen-binding fragment thereof refers to forms of non-human (e.g. murine) antibodies or antigen-binding fragments that are specific immunoglobulin chains, chimeric immunoglobulins, or fragments thereof that contain minimal non-human (e.g., murine) sequences. Typically, humanized antibodies or antigen-binding fragments thereof are human immunoglobulins in which residues from the complementary determining region (CDR) are replaced by residues from the CDR of a non-human species (e.g. mouse, rat, rabbit, hamster) that have the desired specificity, affinity, and capability ("CDR grafted") (Jones et al., Nature 321:522-525 (1986); Riechmann et al., Nature 332:323-327 (1988); Verhoeyen et al., Science 239:1534-1536 (1988)). In some instances, the Fv framework region (FR) residues of a human immunoglobulin are replaced with the corresponding residues in an antibody or fragment from a non-human species that has the desired specificity, affinity, and capability. The humanized antibody or antigen-binding fragment thereof can be further modified by the substitution of additional residues either in the Fv framework region and/or within the replaced non-human residues to refine and optimize antibody or antigen-binding fragment thereof specificity, affinity, and/or capability. In general, the humanized antibody or antigen-binding fragment thereof will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody or antigen-binding fragment thereof can also comprise at least a portion of an immunoglobulin constant region or domain (Fc), typically that of a human immunoglobulin. Examples of methods used to generate humanized antibodies are described in U.S. Pat. No. 5,225,539; Roguska et al., Proc. Natl. Acad. Sci., USA, 91(3):969-973 (1994), and Roguska et al., Protein Eng. 9(10):895-904 (1996). In some embodiments, a "humanized antibody" is a resurfaced antibody.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al., Sequences of Proteins of Immunological Interest, (5th ed., 1991, National Institutes of Health, Bethesda Md.), "Kabat"); and (2) an approach based on crystallographic studies of antigen-antibody complexes (Al-lazikani et al, J. Molec. Biol. 273:927-948 (1997)). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g., Kabat et al., Sequences of Immunological Interest. (5th Ed., 1991, National Institutes of Health, Bethesda, Md.) ("Kabat").

The amino acid position numbering as in Kabat, refers to the numbering system used for heavy chain variable domains or light chain variable domains of the compilation of antibodies in Kabat et al. (Sequences of Immunological Interest. (5th Ed., 1991, National Institutes of Health, Bethesda, Md.), "Kabat"). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues can be determined for a given antibody by alignment at regions of homology of the sequence of the antibody with a "standard" Kabat numbered sequence. Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B (Kabat Numbering) | H26-H32..34 |
| H1 | H31-H35 | H26-H35 (Chothia Numbering) | H26-H32 |
| H2 | H50-H65 | H50-H58 | H52-H56 |
| H3 | H95-H102 | H95-H102 | H95-H102 |

The term "human" antibody or antigen-binding fragment thereof means an antibody or antigen-binding fragment thereof produced by a human or an antibody or antigen-binding fragment thereof having an amino acid sequence corresponding to an antibody or antigen-binding fragment thereof produced by a human made using any technique known in the art. This definition of a human antibody or antigen-binding fragment thereof includes intact or full-length antibodies and fragments thereof.

The term "chimeric" antibodies or antigen-binding fragments thereof refers to antibodies or antigen-binding fragments thereof wherein the amino acid sequence is derived from two or more species. Typically, the variable region of both light and heavy chains corresponds to the variable region of antibodies or antigen-binding fragments thereof derived from one species of mammals (e.g. mouse, rat, rabbit, etc.) with the desired specificity, affinity, and capability while the constant regions are homologous to the sequences in antibodies or antigen-binding fragments thereof derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd) Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. Specific illustrative embodiments are described in the following.

"Or better" when used herein to refer to binding affinity refers to a stronger binding between a molecule and its binding partner. "Or better" when used herein refers to a stronger binding, represented by a smaller numerical Kd value. For example, an antibody which has an affinity for an antigen of "0.6 nM or better", the antibody's affinity for the antigen is <0.6 nM, i.e. 0.59 nM, 0.58 nM, 0.57 nM etc. or any value less than 0.6 nM.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this disclosure are based upon antibodies, in certain embodiments, the polypeptides can occur as single chains or associated chains.

The term "immunoconjugate" or "conjugate" as used herein refers to a compound or a derivative thereof that is linked to a cell binding agent (i.e., an anti-CD123 antibody or fragment thereof) and is defined by a generic formula: C-A, wherein C=cytotoxin (e.g., such as an indolino-benzodiazepine (IGN) DNA-alkylator (e.g., DGN549-C)) and A=antibody or antigen-binding fragment thereof, e.g., an anti-CD123 antibody or antibody fragment. An immunoconjugate can optionally contain a linker and be defined by the generic formula C-L-A, wherein C=cytotoxin, L=linker, and A=antibody or antigen-binding fragment thereof, e.g., an anti-CD123 antibody or antibody fragment. Immunoconjugates can also be defined by the generic formula in reverse order: C-A or A-L-C. Immunoconjugates can also contain multiple cytotoxins (C) per antibody or antigen-binding fragment thereof (A) or multiple cytotoxins (C) and linkers (L) per antibody or antigen-binding fragment thereof (A).

A "linker" is any chemical moiety that is capable of linking a compound, usually a drug (such as IGN DNA-alkylators), to a cell-binding agent (such as an anti-CD123 antibody or a fragment thereof) in a stable, covalent manner. Linkers can be susceptible to or be substantially resistant to acid-induced cleavage, light-induced cleavage, peptidase-induced cleavage, esterase-induced cleavage, and disulfide bond cleavage, at conditions under which the compound or the antibody remains active. Suitable linkers are well known in the art and include, for example, disulfide groups, thioether groups, acid labile groups, photolabile groups, peptidase labile groups and esterase labile groups. Linkers also include charged linkers, and hydrophilic forms thereof as described herein and know in the art. In some embodiments disclosed herein, the linker is a peptide linker.

Figure 1B:
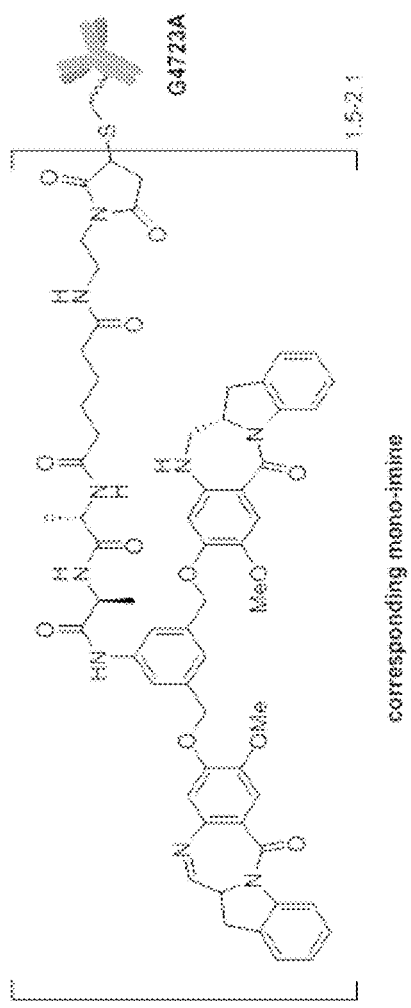
FIG. 1B shows an unsulfonated form of the immunoconjugate containing the anti-CD123 G4723A antibody linked to the cytotoxic payload DGN549-C (the mono-imine structure), which can also be present in an IMGN632 composition.
Figures 2A, 2B:
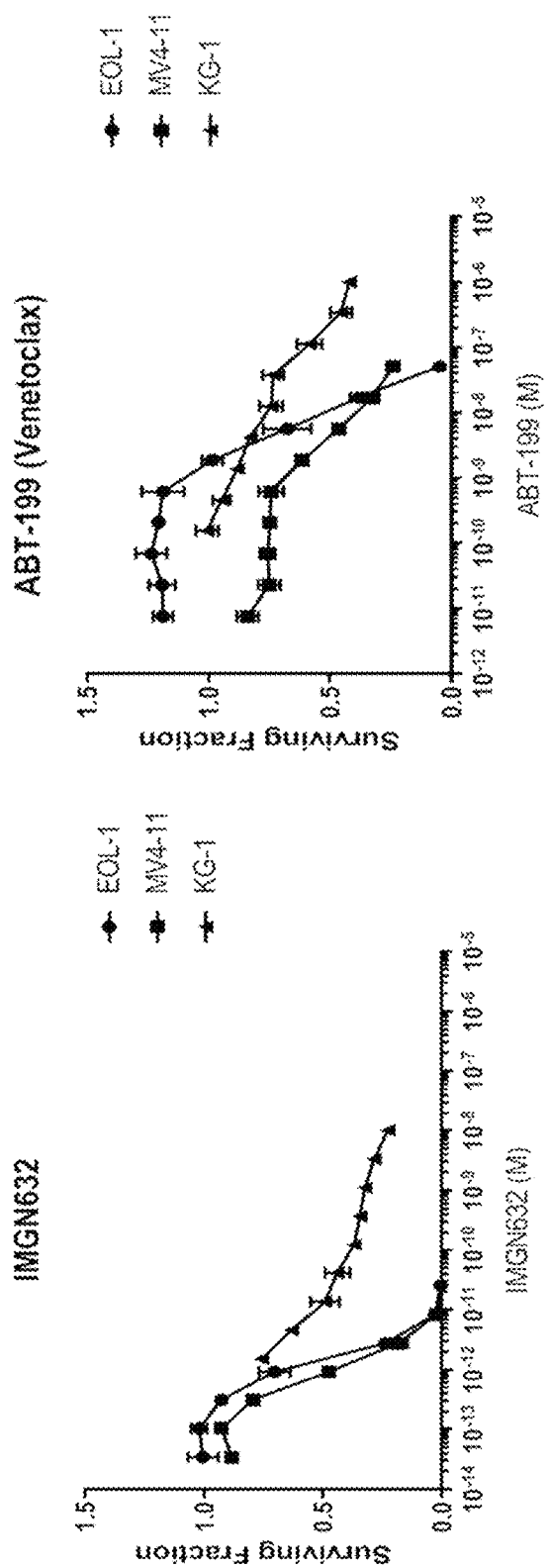
FIG. 2A shows the antitumor activity of a broad range of doses of IMGN632 against three acute myeloid leukemia (AML) (EOL-1, MV4-11, KG-1) cell lines.
FIG. 2B shows the antitumor activity of a broad range of doses of venetoclax against three AML (EOL-1, MV4-11, KG-1) cell lines.
Figures 2C, 2D:
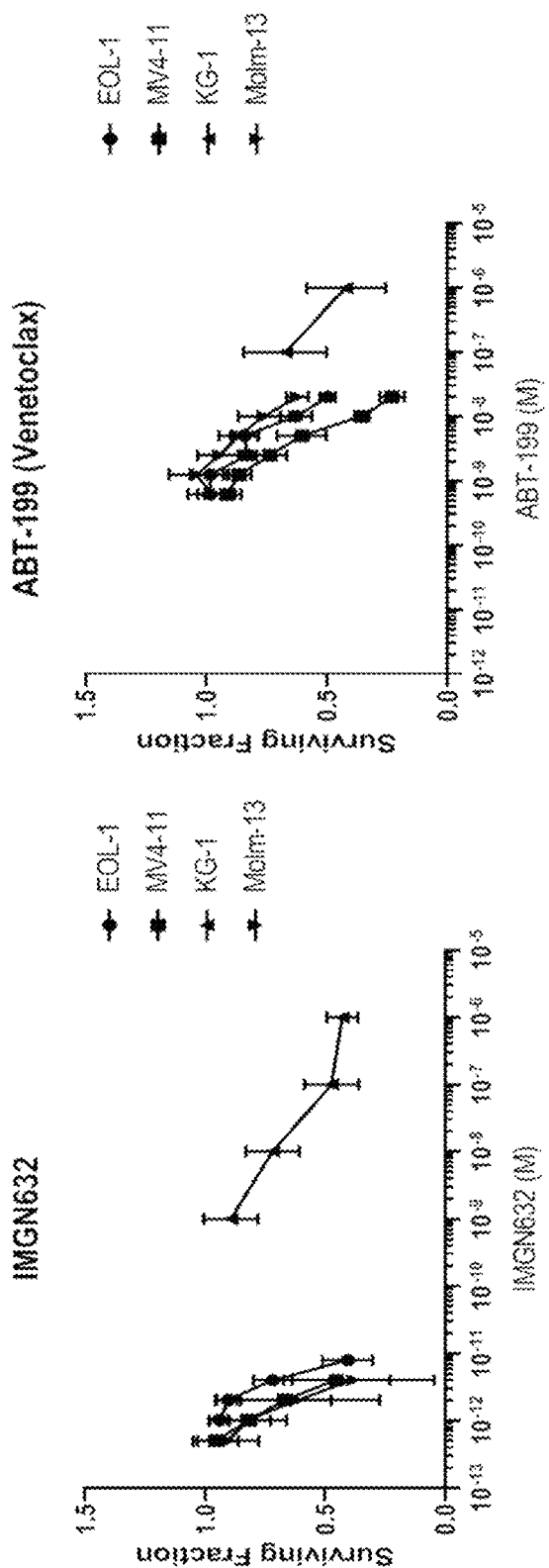
FIG. 2C shows the antitumor activity of a narrower range of doses of IMGN632 against four AML (EOL-1, MV4-11, KG-1, Molm-13) cell lines.
FIG. 2D shows the antitumor activity of a narrower range of doses of venetoclax against four AML (EOL-1, MV4-11, KG-1, Molm-13) cell lines.

The term "IMGN632" refers to the immunoconjugate composition shown in FIGS. 6A and 6B. The immunoconjugate composition comprises immunoconjugates comprising an average of 1.5 to 2.1 DGN549-C cytotoxic agents per huCD123-6Gv4.7 ("G4723A") antibody in a sulfonated version (FIG. 1A). The immunoconjugate composition can also comprise the unsulfonated immunoconjugate (the mono-imine structure shown in FIG. 1B).

The term "BCL-2 inhibitor" refers to an agent that is capable of inhibiting an activity of B-cell leukemia/lymphoma-2 ("BCL-2"). For example, a BCL-2 inhibitor can bind to BCL-2 and reduce the interaction of BCL-2 with pro-apoptotic proteins (e.g., BH3-only proteins). Venetoclax is an exemplary BCL-2 inhibitor.

The term "hypomethylating agent" or "HMA" refers to agents that inhibits DNA methylation. For example, an HMA can act by inhibiting a DNA methyltransferase. Azacitidine and decitabine are exemplary HMAs.

The terms "cancer" and "cancerous" refer to or describe the physiological condition in mammals in which a population of cells are characterized by unregulated cell growth.

Examples of cancer include, but are not limited to, carcinoma, lymphoma, blastoma, sarcoma, and leukemia. "Tumor" and "neoplasm" refer to one or more cells that result from excessive cell growth or proliferation, either benign (noncancerous) or malignant (cancerous) including pre-cancerous lesions. A cancer as disclosed herein can be a hematological malignancy. Examples of hematological malignancies include, for example, acute myeloid leukemia (AML), chronic myeloid leukemia (CML), myelodysplastic syndrome (MDS), acute lymphoblastic leukemia (ALL) such as B-cell acute lymphoblastic leukemia (B-ALL), T-cell acute lymphoblastic leukemia (T ALL), mixed-lineage leukemia ALL (MLL-ALL), B-cell precursor ALL (BCP-ALL), Ph+ ALL, Ph-like ALL, chronic lymphocytic leukemia (CLL), chronic myeloid leukemia in blast crisis/phase (BP-CML), and blastic plasmacytoid dendritic cell neoplasm (BPDCN). Additional examples of "cancer" include, B-cell lymphomas including NHL, precursor B-cell lymphoblastic leukemia/lymphoma and mature B-cell neoplasms, such as B-cell chronic lymphocytic leukemia (CLL)/small lymphocytic lymphoma (SLL), B-cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B-cell lymphoma (MALT type, nodal and splenic type), hairy cell leukemia, diffuse large B-cell lymphoma, Burkitt's lymphoma, plasmacytoma, plasma cell myeloma, post-transplant lymphoproliferative disorder, Waldenstrom's macroglobulinemia, and anaplastic large-cell lymphoma (ALCL). The cancer can be a cancer that expresses CD123 ("CD123-expressing cancer").

The terms "cancer cell," "tumor cell," and grammatical equivalents refer to the total population of cells derived from a tumor or a pre-cancerous lesion, including both non-tumorigenic cells, which comprise the bulk of the tumor cell population, and tumorigenic stem cells (cancer stem cells). As used herein, the term "tumor cell" will be modified by the term "non-tumorigenic" when referring solely to those tumor cells lacking the capacity to renew and differentiate to distinguish those tumor cells from cancer stem cells.

A "refractory" cancer is one that progresses even though an anti-cancer treatment, such as a chemotherapy, is administered to the cancer patient. The cancer may be resistant at the beginning of treatment or it may become resistant during treatment.

A "primary refractory" cancer is one that does not achieve complete remission (CR) or complete remission with incomplete recovery (CRi) after a patient has received 2 cycles of intense chemotherapy.

A "relapsed" cancer is one in which the cancer or the signs and symptoms of a cancer returns after a period of improvement.

The term "fit AML" as used herein refers to a subject having AML who is eligible for intensive therapy. The measures for determining a subject with fit AML include, e.g., physical performance (as determined by e.g., the Eastern Cooperative Oncology Group performance status (ECOG PS), the Karnofsky performance status (KPS), and the short physical performance battery (SPPB)), comorbid conditions (as determined by the Charlson comorbidity index (CCI) or the hematopoietic cell transplantation-specific comorbidity index (HCT-CI)), cognitive function, and prognostic models (including but not limited to, cytogenetic group, age, white blood cell count, LDH, type of AML). In some cases, a fit AML subject is a subject at the age of 60 or under the age of 60.

The term "unfit AML" as used herein refers to a subject having AML who is ineligible for intensive therapy. The measures for determining a subject with unfit AML include, e.g., physical performance (as determined by e.g., the Eastern Cooperative Oncology Group performance status (ECOG PS), the Karnofsky performance status (KPS), and the short physical performance battery (SPPB)), comorbid conditions (as determined by the Charlson comorbidity index (CCI) or the hematopoietic cell transplantation-specific comorbidity index (HCT-CI)), cognitive function, and prognostic models (including but not limited to, cytogenetic group, age, white blood cell count, LDH, type of AML). In some cases, an unfit AML subject is a subject over the age of 60.

The term "increased expression" or "overexpression" CD123 in a particular tumor, tissue, or cell sample refers to CD123 that is present at a level higher than that which is present in a healthy or non-diseased (native, wild type) tissue or cells of the same type or origin.

Terms such as "treating" or "treatment" or "to treat" or "alleviating" or "to alleviate" refer to therapeutic measures that cure, slow down, lessen symptoms of, and/or halt progression of a diagnosed pathologic condition or disorder. Thus, those in need of treatment include those already diagnosed with or suspected of having the disorder.

The term "therapeutically effective amount" refers to an amount of an antibody, immunoconjugate, or other drug effective to "treat" a disease or disorder in a subject or mammal. In the case of cancer, the therapeutically effective amount of the drug can reduce the number of cancer cells; reduce the tumor size or burden; inhibit (i.e., slow to some extent and in a certain embodiment, stop) cancer cell infiltration into peripheral organs; relieve to some extent one or more of the symptoms associated with the cancer; and/or result in a favorable response such as complete remission (CR), complete remission with incomplete recovery (CRi); complete remission with partial hematologic recovery (CRh); CR without minimal residual disease (CRMRD−); complete remission clinical (CRc); morphologic leukemia-free state (MLFS); partial remission (PR); duration of response (DOR); and decrease in progressive disease (PD).

The term "respond favorably" generally refers to causing a beneficial state in a subject. With respect to cancer treatment, the term refers to providing a therapeutic effect on the subject. Positive therapeutic effects in cancer can be measured in a number of ways (See, W. A. Weber, J. Nucl. Med. 50:1S-10S (2009)). A favorable response can be assessed, for example, by complete remission (CR), complete remission with incomplete recovery (CRi); CR without minimal residual disease (CRMRD−); complete remission clinical (CRc); morphologic leukemia-free state; partial remission (PR); a decrease in progressive disease (PD), or any combination thereof.

A "complete response" or "complete remission" or "CR" indicates the disappearance of all signs of tumor or cancer in response to treatment. This does not always mean the cancer has been cured. A "CRi" refers to a morphologically complete remissions with an incomplete hematological (blood count) recovery. A "CRMRD−" refers to a complete recovery without measurable residual disease.

"Minimal residual disease," "MRD" or "MRD+" refers to post-therapy persistence of cancerous (e.g., leukemic) cells at levels below morphological detection. MRD can be assessed using, for example, central flow cytometry. MRD+ status is a predictor of relapse, and it is associated with decrease survival in AML patients.

A "partial response" or "PR" refers to a decrease in the size or volume of one or more tumors or lesions, or in the extent of cancer in the body, in response to treatment.

"Progressive disease" refers to the appearance of one more new lesions or tumors and/or the unequivocal progression of existing non-target lesions. Progressive disease can also refer to a tumor growth of more than 20% since treatment began, either due to an increases in mass or in spread of the tumor.

The terms "line of treatment" or "line of therapy" refer to a therapeutic regimen that can include but is not limited to surgery, radiation therapy, chemotherapy, differentiating therapy, biotherapy, immune therapy, induction therapy, consolidation therapy, transplant, maintenance therapy, or the administration of one or more anti-cancer agents (e.g., a cytotoxic agent and/or an anti-proliferative compound).

The terms "first-line treatment," "first-line therapy," and "front-line therapy" refer to the preferred and standard initial treatment for a particular condition, e.g., induction therapy, consolidation therapy, transplant, maintenance therapy. These treatments differ from "second-line" therapies, which are tried when a first-line therapy does not work adequately. "Third-line" therapies are tried when a first-line therapy and a second-line therapy do not work adequately. "Salvage therapy" or "salvage regimen" is a treatment that is tried when the cancer has not responded to other treatments.

For example, the combination of a CD123 immunoconjugate (e.g. IMGN632) with a BCL-2 inhibitor, and/or an HMA provided herein can be given as a first-line therapy, a second-line therapy, or a third-line therapy. The combination of a CD123 immunoconjugate (e.g. IMGN632) with a BCL-2 inhibitor, and/or an HMA provided herein can be given as a line of therapy in patients having received at least 1, at least 2, or at least 3 lines of therapy (e.g., front-line therapy and one salvage therapy) prior to treatment with the combination of a CD123 immunoconjugate (e.g. IMGN632) with a BCL-2 inhibitor, and/or an HMA provided herein. In some embodiments, the combination of a CD123 immunoconjugate (e.g. IMGN632) with a BCL-2 inhibitor, and/or an HMA provided herein can be given as a line of therapy in patients having received no more than 1, no more than 2, no more than 3, no more than 4, no more than 5, or no more than 6 lines of therapy.

The term "maintenance therapy" refers to therapy that is given to help keep cancer from coming back after it has disappeared following the initial therapy.

The phrase "pharmaceutically acceptable" indicates that the substance or composition must be compatible chemically and/or toxicologically, with the other ingredients comprising a formulation, and/or the mammal being treated therewith.

The term "pharmaceutical formulation" refers to a preparation which is in such form as to permit the biological activity of the active ingredient to be effective, and which contains no additional components which are unacceptably toxic to a subject to which the formulation would be administered. The formulation can be sterile.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

Administration "in combination with" one or more further therapeutic agents includes simultaneous (concurrent) or consecutive administration in any order.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered serially, by alternation, or in parallel as separate formulations; or (3) by some other regimen. When delivered in alternation therapy, a synergistic effect can be attained when the compounds are administered or delivered sequentially, e.g., by different injections in separate syringes.

The term "instructing" means providing directions for applicable therapy, medication, treatment, treatment regimens, and the like, by any means, for example, in writing, such as in the form of package inserts or other written promotional material.

An "effective amount" of an antibody, immunoconjugate, or other drug as disclosed herein is an amount sufficient to carry out a specifically stated purpose. An "effective amount" can be determined empirically and in a routine manner, in relation to the stated purpose.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition which is isolated is substantially pure.

As used herein, "substantially pure" refers to material which is at least 50% pure (i.e., free from contaminants), at least 90% pure, at least 95% pure, at least 98% pure, or at least 99% pure.

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. Anti-CD123 Immunoconjugates

Described herein are methods of administering immunoconjugates that specifically bind CD123 (e.g., IMGN632) in combination with other agents. Immunoconjugates that specifically bind to CD123 are referred to herein as "CD123-immunoconjugates" or "anti-CD123 immunoconjugates." Such immunoconjugates comprise an anti-CD123 antibody or antigen-binding fragment thereof and a drug (e.g., a cytotoxic agent). The drug (e.g., a cytotoxic agent) can be attached to the anti-CD123 antibody or antigen-binding fragment thereof by a linker.

In some embodiments, the anti-CD123 antibodies or antigen-binding fragments thereof are humanized antibodies or antigen-binding fragments thereof. In some embodiments, the humanized antibody or fragment is a resurfaced antibody or antigen-binding fragment thereof. In other embodiments, the antibodies or antigen-binding fragments thereof is a fully human antibody or antigen-binding fragment thereof.

In one embodiment, an immunoconjugate is represented by the following formula:

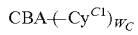

wherein CBA is an anti-CD123 antibody or antigen-binding fragment or polypeptide, covalently linked to CyC1 through a cysteine residue; and WC is 1 or 2.

In the above formula, $Cy^{C1}$ is represented by the following formulae:

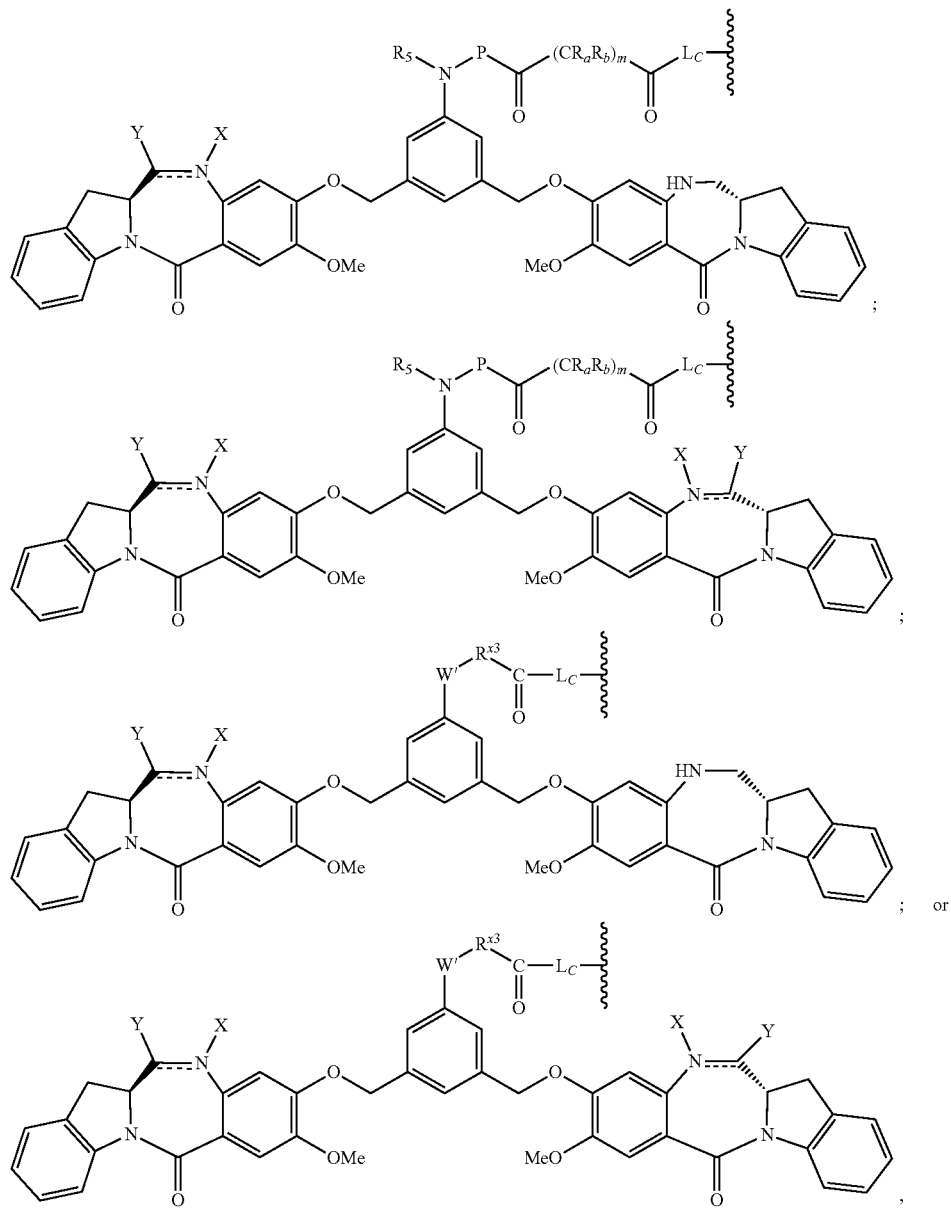

or a pharmaceutically acceptable salt thereof, wherein the double line ═ between N and C represents a single bond or a double bond, provided that when it is a double bond, X is absent and Y is —H or a (C1-C4)alkyl; and when it is a single bond, X is —H or an amine protecting moiety, Y is —OH or —SO3M, and M is H+ or a cation;

$R_5$ is —H or a $(C_1$-$C_3)$alkyl;

P is an amino acid residue or a peptide containing 2 to 20 amino acid residues;

$R_a$ and $R_b$, for each occurrence, are independently —H, $(C_1$-$C_3)$alkyl, or a charged substituent or an ionizable group Q;

W' is —NR$^{e'}$,

R$^{e'}$ is —(CH$_2$—CH$_2$—O)$_n$—R$^k$;

n is an integer from 2 to 6;

R$^k$ is —H or -Me;

$R^{x3}$ is a $(C_1$-$C_6)$alkyl; and, $L_C$ is represented by

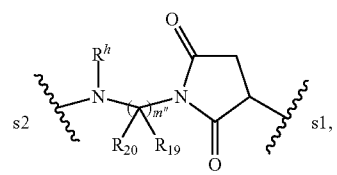

s1 is the site covalently linked to CBA, and s2 is the site covalently linked to the —C(═O)— group on $Cy^{C1}$;

wherein:

$R_{19}$ and $R_{20}$, for each occurrence, are independently —H or a $(C_1-C_3)$alkyl;

m" is an integer between 1 and 10; and $R^h$ is —H or a $(C_1-C_3)$alkyl.

In certain embodiments, $R_a$ and $R_b$ are both H; and $R_5$ is H or Me.

In certain embodiments, P is a peptide containing 2 to 5 amino acid residues. For example, P may be selected from Gly-Gly-Gly, Ala-Val, Val-Ala, Val-Cit, Val-Lys, Phe-Lys, Lys-Lys, Ala-Lys, Phe-Cit, Leu-Cit, Ile-Cit, Trp, Cit, Phe-Ala, Phe-$N^9$-tosyl-Arg, Phe-$N^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu, β-Ala-Leu-Ala-Leu, Gly-Phe-Leu-Gly, Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, and Met-Ala. In certain embodiments, P is Gly-Gly-Gly, Ala-Val, Ala-Ala, Ala-D-Ala, D-Ala-Ala, or D-Ala-D-Ala. In certain embodiments, Q is —$SO_3M$.

In certain embodiments, $R_{19}$ and $R_{20}$ are both H; and m" is an integer from 1 to 6.

In certain embodiments, $-L_C-$ is represented by the following formula:

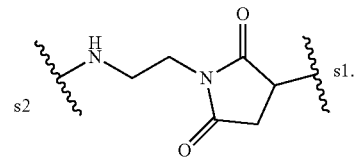 [SMILES: *NCCN1C(=O)CC(*)C1=O]

In certain embodiments, the immunoconjugate is represented by the following formulae:

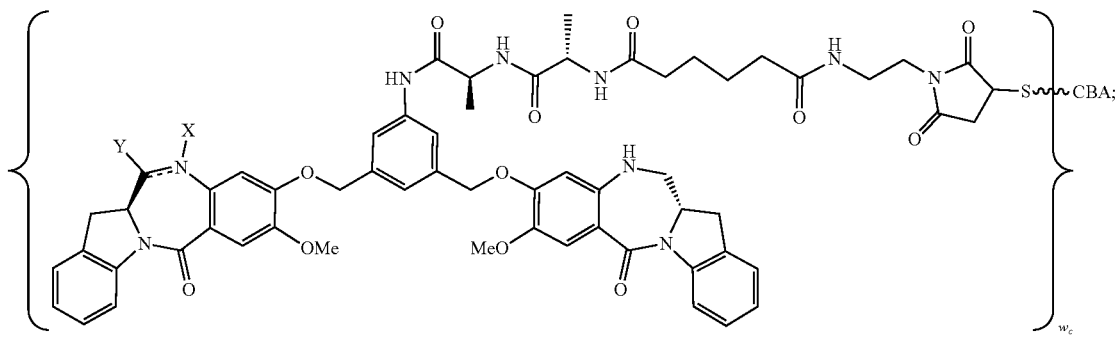

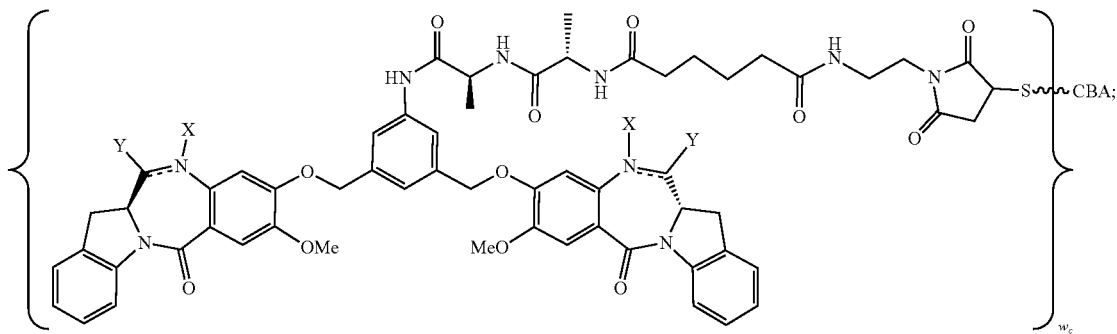

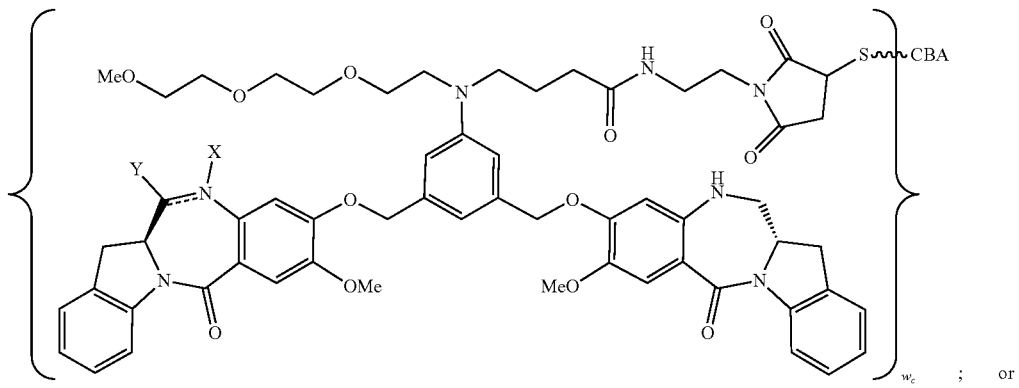

; or

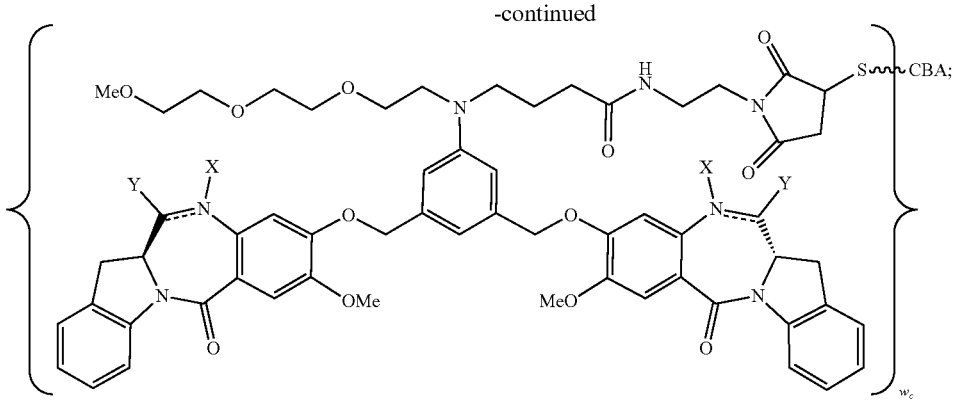

or a pharmaceutically acceptable salt thereof, wherein the double line ═ between N and C represents a single bond or a double bond, provided that when it is a double bond, X is absent and Y is —H, and when it is a single bond, X is —H, and Y is —OH or —SO3M.

By way of example, an anti-CD123 antibody or antigen-binding fragment thereof can be in an immunoconjugate used in the present methods. Anti-CD123 antibodies or antigen-binding fragments thereof have been described (see e.g., U.S. Pat. No. 10,077,313 B2, the contents of which are herein incorporated by reference in their entirety). The anti-CD123 antibody or antigen-binding fragment thereof can be the huCD123-6Gv4.7 ("G4723A") antibody (see WO 2017/004025, WO 2017/004026, and PCT/US2018/052212, the contents of each of which are herein incorporated by reference in their entireties) or can contains sequences of the G4723A antibody, e.g., as shown below in Tables 1-3. For example, an anti-CD123 antibody or antigen-binding fragment thereof for use in the methods provided herein can comprise variable heavy chain CDR-1, CDR-2, and CDR-3 comprising the sequences of SEQ ID NOs: 5, 6, and 7, respectively and/or variable light chain CDR-1, CDR-2, and CDR-3 comprising the sequences of SEQ ID NOs: 8, 9, and 10, respectively. An anti-CD123 antibody or antigen-binding fragment thereof for use in the methods provided herein can comprise a variable heavy chain domain comprising the sequence set forth in SEQ ID NO:1. An anti-CD123 antibody or antigen-binding fragment thereof for use in the methods provided herein can comprise a variable light chain domain comprising the sequence set forth in SEQ ID NO:2. An anti-CD123 antibody or antigen-binding fragment thereof for use in the methods provided herein can comprise a variable heavy chain domain comprising the sequence set forth in SEQ ID NO:1 and a variable light chain domain comprising the sequence set forth in SEQ ID NO:2. An anti-CD123 antibody or antigen-binding fragment thereof for use in the methods provided herein can comprise a heavy chain comprising the sequence set forth in SEQ ID NO:3. An anti-CD123 antibody or antigen-binding fragment thereof for use in the methods provided herein can comprise a light chain comprising the sequence set forth in SEQ ID NO:4. An anti-CD123 antibody or antigen-binding fragment thereof for use in the methods provided herein can comprise a heavy chain comprising the sequence set forth in SEQ ID NO:3 and a light chain comprising the sequence set forth in SEQ ID NO:4.

TABLE 1 huCD123-6Gv4.7 Heavy and Light Chain Variable Regions

| Name | Sequence |
|---|---|
| huCD123-6Gv7 Heavy Chain Variable Region | QVQLVQSGAEVKKPGASVKVSCKASGYIFTSSI MHWVRQAPGQGLEWIGYIKPYNDGTKYNEKFKG RATLTSDRSTSTAYMELSSLRSEDTAVYYCARE GGNDYYDTMDYWGQGTLVTVSS (SEQ ID NO: 1) |
| huCD123-6Gv4 Light Chain Variable Region | DIQMTQSPSSLSASVGDRVTITCRASQDINSYLS WFQQKPGKAPKTLIYRVNRLVDGVPSRFSGSGSG NDYTLTISSLQPEDFATYYCLQYDAFPYTFGQGT KVEIKR (SEQ ID NO: 2) |

TABLE 2 huCD123-6Gv4.7-C442 Full Length Heavy and Light Chain

| Name | Sequence |
|---|---|
| huCD123-6Gv7-C442 Full Length Heavy Chain | QVQLVQSGAEVKKPGASVKVSCKASGYIF TSSIMHWVRQAPGQGLEWIGYIKPYNDGT KYNEKFKGRATLTSDRSTSTAYMELSSLR SEDTAVYYCAREGGNDYYDTMDYWGQGTL VTVSSASTKGPSVFPLAPSSKSTSGGTAA LGCLVKDYFPEPVTVSWNSGALTSGVHTF PAVLQSSGLYSLSSVVTVPSSSLGTQTYI CNVNHKPSNTKVDKKVEPKSCDKTHTCPP CPAPELLGGPSVFLFPPKPKDTLMISRTP EVTCVVVDVSHEDPEVKFNWYVDGVEVHN AKTKPREEQYNSTYRVVSVLTVLHQDWLN GKEYKCKVSNKALPAPIEKTISKAKGQPR EPQVYTLPPSRDELTKNQVSLTCLVKGFY PSDIAVEWESNGQPENNYKTTPPVLDSDG SFFLYSKLTVDKSRWQQGNVFSCSVMHEA LHNHYTQKSLCLSPG (SEQ ID NO: 3) |
| huCD123-6Gv4 Full Length Light Chain | DIQMTQSPSSLSASVGDRVTITCRASQDI NSYLSWFQQKPGKAPKTLIYRVNRLVDGV PSRFSGSGSGNDYTLTISSLQPEDFATYY CLQYDAFPYTFGQGTKVEIKRTVAAPSVF IFPPSDEQLKSGTASVVCLLNNFYPREAK VQWKVDNALQSGNSQESVTEQDSKDSTYS LSSTLTLSKADYEKHKVYACEVTHQGLSS PVTKSFNRGEC (SEQ ID NO: 4) |

TABLE 3 huCD123-6Gv4.7 Variable Heavy and Light
Chain Complementary Determining Regions

| Name | Sequence |
| --- | --- |
| huCD123-6Gv7 Variable Heavy Chain CDR1 | SSIMH (SEQ ID NO: 5) |
| huCD123-6Gv7 Variable Heavy Chain CDR2 | YIKPYNDGTKYNEKFKG (SEQ ID NO: 6) |
| huCD123-6Gv7 Variable Heavy Chain CDR3 | EGGNDYYDTMDY (SEQ ID NO: 7) |
| huCD123-6Gv4 Variable Light Chain CDR1 | RASQDINSYLS (SEQ ID NO: 8) |
| huCD123-6Gv4 Variable Light Chain CDR2 | RVNRLVD (SEQ ID NO: 9) |
| huCD123-6Gv4 Variable Light Chain CDR3 | LQYDAFPYT (SEQ ID NO: 10) |

An anti-CD123 antibody or antigen-binding fragment thereof for use in the methods provided herein can bind to an epitope within amino acids 205 to 346 of human CD123.

An anti-CD123 antibody or antigen-binding fragment thereof for use in methods provided herein can be recombinantly produced. For example, an anti-CD123 antibody or antigen-binding fragment thereof for use in the methods provided herein can be produced in a mammalian cell line, e.g., a CHO cell.

An anti-CD123 antibody or antigen-binding fragment thereof for use in the methods provided herein can be a cysteine-engineered antibody or fragment. Cysteine-engineered antibodies can be covalently conjugated to cytotoxic agents of interest to generate immunoconjugates.

As used herein, the expression "linked to a cell-binding agent" or "linked to an anti-CD123 antibody or fragment" refers to a conjugate molecule comprising at least one cytotoxic agent bound to a cell-binding agent, e.g., anti-CD123 antibody or fragment, via a suitable linking group, or a precursor thereof. Linkers include, for example, peptide linkers.

An immunoconjugate can contain multiple cytotoxic agents bound to an antibody or antigen-binding fragment thereof. As provided herein, in certain instances, about 1 to about 3 drug molecules e.g., cytotoxic agents, are linked to an anti-CD123 antibody or antigen-binding fragment thereof. In one aspect, an immunoconjugate comprises 1, 2, or 3, cytotoxic agents per antibody or antigen-binding fragment thereof.

A composition comprising immunoconjugates can contain immunoconjugates with varying numbers of cytotoxic agents bound per antibody or antigen-binding fragment thereof. Thus, compositions comprising immunoconjugates can contain an average number of cytotoxic agents bound per antibody or antigen-binding fragment thereof. In one aspect, a pharmaceutical composition comprising anti-CD123 immunoconjugates comprises about 1 to about 3 cytotoxic agents per anti-CD123 antibody or antigen-binding fragment thereof, about 1.5 to about 2.5 cytotoxic agents per anti-CD123 antibody or antigen-binding fragment thereof, about 1.5 to about 2.1 cytotoxic agents per anti-CD123 antibody or antigen-binding fragment thereof, or about 1.5 to about 2.0 cytotoxic agents cytotoxic agents per anti-CD123 antibody or antigen-binding fragment thereof.

In certain instances, a pharmaceutical composition for use in the methods provided herein comprises anti-CD123 immunoconjugates comprising about 1 to about 3 cytotoxic agents per antibody or antigen-binding fragment thereof, for example, wherein the average number of cytotoxic agents per antibody or antigen-binding fragment thereof is from about 1 to about 3 (e.g., 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0).

In certain instances, a pharmaceutical composition for use in the methods provided herein comprises anti-CD123 immunoconjugates with an average of about 1±0.2, about 1.1±0.2, about 1.2±0.2, about 1.3±0.2, about 1.4±0.2, about 1.5±0.2, about 1.6±0.2, about 1.7±0.2, about 1.8±0.2, about 1.9±0.2, about 2.0±0.2, about 2.1±0.2, 2.2±0.2, 2.3±0.2, 2.4±0.2, 2.5±0.2, or 2.6±0.2 drug molecules (e.g., cytotoxic agents) attached per antibody or antigen-binding fragment thereof. In certain aspects, a pharmaceutical composition provided herein comprises anti-CD123 immunoconjugates with an average of about 1.5 to 2.1 drug molecules (e.g., cytotoxic agents) per antibody.

The antibodies or antigen-binding fragments thereof for use in the present disclosure may be linked to cytotoxic agents, for example, through linkage with the Lys side chain amino group, the Cys side chain thiol group, or an oxidized N-terminal Ser/Thr. Cytotoxic agents include, for example, DNA alkylating agents such as indolino-benzodiazepene (IGN) DNA alkylators. In certain instances, a cytotoxic agent is a indolino-benzodiazepine pseudodimer. In certain instances, an anti-CD123 immunoconjugate for use in the present disclosure comprises DGN549-C.

III. BCL-2 Inhibitors

Described herein are methods of administering anti-CD123 immunoconjugates such as IMGN632 in combination with BCL-2 inhibitors. Overexpression of BCL-2 has been demonstrated in CLL and AML cells, where it mediates tumor cell survival and has been associated with resistance to chemotherapeutics. BCL-2 inhibitors can reverse this effect, e.g., by promoting apoptosis.

BCL-2 inhibitors include, for example, venetoclax (Venclexta®), GX15-070 (GeminX), AT-101 (Ascenta) and ABT-263 (Navitoclax; Abbott).

Venetoclax (also known as 4-(4-{[2-(4-chlorophenyl)-4,4 dimethylcyclohex-1-en-1-yl]methyl}piperazin-1-yl)-N-({3-nitro-4-[(tetrahydro-2H-pyran-4 ylmethyl)amino]phenyl}sulfonyl)-2-(1H-pyrrolo[2,3-b]pyridin-5-yloxy)benzamide)) is a selective inhibitor of BCL-2. Venetoclax is believed to help restore the process of apoptosis by binding directly to the BCL-2 protein, displacing pro-apoptotic proteins like BIM, triggering mitochondrial outer membrane permeabilization and the activation of caspases. Venetoclax is the active ingredient in Venclexta®, which is provided as a tablets for oral administration.

In some embodiments, the BCL-2 inhibitor is a small molecule. In some embodiments, the BCL-2 inhibitor is venetoclax.

IV. Hypomethylating Agents

Described herein are methods of administering anti-CD123 immunoconjugates such as IMGN632 in combination with hypomethylating agents, e.g., azacitidine or decitabine.

Azacitidine (also known as "4-amino-1-beta-D-ribofuranosyl-s-triazin-2(1H)-one" or "5-azacytine") is a pyrimidine nucleoside analogue. It is thought to induce antineoplastic activity via two mechanisms: inhibition of DNA methyltransferase at low doses, causing hypomethylation of DNA, and direct cytotoxicity in abnormal hematopoietic cells in the bone marrow through its incorporation into DNA and RNA at high doses, resulting in cell death. Azacitine is the active ingredient in Vidaza®, which is provided as a sterile form for reconstitution as a suspension for subcutenous injection or reconstitution as a solution with further dilution for intravenous administration.

Decitabine (also known as 4-amino-1-(2-deoxy-β-D-erythro-pentofuranosyl)-1,3,5-triazin2(1H)-one) is an analog of nucleoside 2'-deoxycytidine. It is believed to exert its antineoplastic effects after phosphorylation and direct incorporation into DNA and inhibition of DNA methyltransferase, causing hypomethylation of DNA and cellular differentiation or apoptosis. Decitabine is the active ingredient in Dacogen®, which is provided as a sterile lyophilized powder for reconstitution for intravenous administration.

Administration of an HMA in combination with an anti-CD123 immunoconjugate (e.g., IMGN632) can reduce the amount and/or frequency of HMA required to achieve the same efficacy, thereby reducing the toxicity of the therapy. Administration of an HMA in combination with an anti-CD123 immunoconjugate (e.g., IMGN632) can also increase the efficacy of the therapy.

In some embodiments, the HMA is a small molecule. In some embodiments, the HMA is azacitidine. In some embodiments, the HMA is decitabine.

V. Pharmaceutical Compositions and Kits

As provided herein, anti-CD123 immunoconjugates (e.g., IMGN632) can be used in combination with BCL-2 inhibitors (e.g., venetoclax) and/or hypomethylating agents (HMAs) (e.g., azacitidine or decitabine) to treat cancer.

In some embodiments, an anti-CD123 immunoconjugate (e.g., IMGN632) and an a BCL-2 inhibitor (e.g., venetoclax) are contained within the same pharmaceutical composition. In some embodiments, an anti-CD123 immunoconjugate (e.g., IMGN632) and a BCL-2 inhibitor (e.g., venetoclax) are contained within two separate pharmaceutical compositions within a single kit. In other embodiments, a kit comprises an anti-CD123 immunoconjugate (e.g., IMGN632) and instructions to administer the anti-CD123 immunoconjugate (e.g., IMGN632) and a BCL-2 inhibitor (e.g., venetoclax). In other embodiments, a kit comprises a BCL-2 inhibitor (e.g., venetoclax) and instructions to administer the BCL-2 inhibitor (e.g., venetoclax) and an anti-CD123 immunoconjugate (e.g., IMGN632).

In some embodiments, an anti-CD123 immunoconjugate (e.g., IMGN632) and an HMA (e.g., azacitidine or decitabine) are contained within the same pharmaceutical composition. In some embodiments, an anti-CD123 immunoconjugate (e.g., IMGN632) and an HMA (e.g., azacitidine or decitabine) are contained within two separate pharmaceutical compositions within a single kit. In other embodiments, a kit comprises an anti-CD123 immunoconjugate (e.g., IMGN632) and instructions to administer the anti-CD123 immunoconjugate (e.g., IMGN632) and the HMA (e.g., azacitidine or decitabine). In other embodiments, a kit comprises an HMA (e.g., azacitidine or decitabine) and instructions to administer the HMA (e.g., azacitidine or decitabine) and an anti-CD123 immunoconjugate (e.g., IMGN632).

In some embodiments, an anti-CD123 immunoconjugate (e.g., IMGN632), a BCL-2 inhibitor (e.g., venetoclax), and an HMA (e.g., azacitidine or decitabine) are contained within the same pharmaceutical composition. In some embodiments, an anti-CD123 immunoconjugate (e.g., IMGN632), a BCL-2 inhibitor (e.g., venetoclax), and an HMA (e.g., azacitidine or decitabine) are contained within two or three separate pharmaceutical compositions within a single kit.

In other embodiments, a kit comprises an anti-CD123 immunoconjugate (e.g., IMGN632) and instructions to administer the anti-CD123 immunoconjugate (e.g., IMGN632) with a BCL-2 inhibitor (e.g., venetoclax) and an HMA (e.g., azacitidine or decitabine). In other embodiments, a kit comprises a BCL-2 inhibitor (e.g., venetoclax) and instructions to administer the BCL-2 inhibitor (e.g., venetoclax) with an anti-CD123 immunoconjugate (e.g., IMGN632) and an HMA (e.g., azacitidine or decitabine). In other embodiments, a kit comprises an HMA (e.g., azacitidine or decitabine) and instructions to administer the HMA (e.g., azacitidine or decitabine) with a BCL-2 inhibitor (e.g., venetoclax) and an anti-CD123 immunoconjugate (e.g., IMGN632).

In other embodiments, a kit comprises an anti-CD123 immunoconjugate (e.g., IMGN632), a BCL-2 inhibitor (e.g., venetoclax), and instructions to administer the anti-CD123 immunoconjugate (e.g., IMGN632) and the BCL-2 inhibitor (e.g., venetoclax) with an HMA (e.g., azacitidine or decitabine). In other embodiments, a kit comprises an anti-CD123 immunoconjugate (e.g., IMGN632), an HMA (e.g., azacitidine or decitabine), and instructions to administer the anti-CD123 immunoconjugate (e.g., IMGN632) and the HMA (e.g., azacitidine or decitabine) with a BCL-2 inhibitor (e.g., venetoclax). In other embodiments, a kit comprises a BCL-2 inhibitor (e.g., venetoclax), an HMA (e.g., azacitidine or decitabine), and instructions to administer the anti-BCL-2 inhibitor (e.g., venetoclax), the an HMA (e.g., azacitidine or decitabine) with an anti-CD123 immunoconjugate (e.g., IMGN632).

In certain embodiments, the pharmaceutical compositions provided herein comprise an anti-CD123 immunoconjugate (e.g., IMGN632), a BCL-2 inhibitor (e.g., venetoclax), and/or an HMA (e.g., azacitidine or decitabine) and a pharmaceutically acceptable vehicle. These pharmaceutical compositions find use in inhibiting tumor growth and treating cancer in subjects (e.g., human patients).

The pharmaceutical compositions for use as provided herein can have an anti-CD123 immunoconjugate (e.g., IMGN632), a BCL-2 inhibitor (e.g., venetoclax), and/or an HMA (e.g., azacitidine or decitabine) having the desired degree of purity in a physiologically acceptable carrier, excipient, or stabilizer (Remington's Pharmaceutical Sciences (1990) Mack Publishing Co., Easton, Pa.). Acceptable carriers, excipients, or stabilizers are nontoxic to recipients at the dosages and concentrations employed. (See, e.g., Gennaro, Remington: The Science and Practice of Pharmacy with Facts and Comparisons: Drugfacts Plus, 20th ed. (2003); Ansel et al., Pharmaceutical Dosage Forms and Drug Delivery Systems, 7th ed., Lippencott Williams and Wilkins (2004); Kibbe et al., Handbook of Pharmaceutical Excipients, 3rd ed., Pharmaceutical Press (2000)). The compositions to be used for in vivo administration can be sterile. This is readily accomplished by filtration through, e.g., sterile filtration membranes.

In certain embodiments, a pharmaceutical composition comprising an anti-CD123 immunoconjugate (e.g., IMGN632) and/or an HMA (e.g., azacitidine or decitabine) is formulated for parenteral (e.g., intravenous) administration.

In certain embodiments, a pharmaceutical composition comprising a BCL-2 inhibitor (e.g., venetoclax) is formulated for oral administration, e.g., as a tablet.

VI. Methods of Use

As provided herein, anti-CD123 immunoconjugates (e.g., IMGN632) can be used in combination with BCL-2 inhibitors and/or hypomethylating agents (HMAs) to treat hematological cancers.

VI(A). Cancer Selection

Cancers that can be treated by the methods provided herein include hematological cancers. In certain embodiments, the hematological malignancy is of myeloid origin. In certain embodiments, the hematological malignancy is of lymphoid origin. In certain embodiments, the hematological malignancy is of both myeloid and lymphoid origins. In certain embodiments, the hematological malignancy is a B-cell malignancy. In certain embodiments, the hematological malignancy is a CD123-expressing hematological malignancy.

In certain embodiments, the hematological malignancy is selected from the group consisting of acute myeloid leukemia (AML), myelodysplastic syndrome (MDS), acute lymphoblastic leukemia (ALL), B-cell acute lymphoblastic leukemia (B-ALL), T-cell acute lymphoblastic leukemia (T-ALL), chronic myeloid leukemia in blast crisis/phase (BP-CML), and blastic plasmacytoid dendritic cell neoplasm (BPDCN). In certain embodiments, the hematological malignancy is chronic myelomonocytic leukemia (CMML). In certain embodiments, the hematological malignancy is myelofibrosis (MF).

In certain embodiments, the hematological malignancy is a relapsed hematological malignancy. In certain embodiments, the hematological malignancy is a refractory hematological malignancy.

In certain embodiments, the hematological malignancy is AML. In certain embodiments, the AML is relapsed AML. In certain embodiments, the AML is refractory AML. In certain embodiments, the AML is not secondary AML. In certain embodiments, the AML is fit AML. In certain embodiments, the AML is unfit AML.

In certain embodiments, the hematological malignancy is BPDCN. In certain embodiments, the BPDCN is relapsed BPDCN. In certain embodiments, the BPDCN is refractory BPDCN.

In certain embodiments, the hematological malignancy is ALL. In certain embodiments, the ALL is relapsed ALL. In certain embodiments, the ALL is refractory ALL.

In certain embodiments, the hematological malignancy is MDS. In certain embodiments, the MDS is high risk MDS.

In certain embodiments, the hematological malignancy is chronic myelomonocytic leukemia (CMML).

In certain embodiments, the hematological malignancy is myelofibrosis (MF).

In certain embodiments, the hematological malignancy is chemotherapy resistant.

In certain embodiments, the hematological malignancy is chemotherapy sensitive.

In certain embodiments, the hematological malignancy expresses multidrug resistance 1 (MDR1). In certain embodiments, the hematological malignancy expresses the multidrug resistance (MDR)-related P-glycoprotein (P-gp). In certain embodiments, the hematological malignancy overexpresses MDR1 and P-gp.

In certain embodiments, the hematological malignancy or the subject with the hematological malignancy has an FLT3-ITD mutation. In certain embodiments, the hematological malignancy or the subject with the hematological malignancy does not have an FLT3-ITD mutation.

In certain embodiments, the hematological malignancy is present in the subject as minimal residual disease (MRD). In certain embodiments, an MRD+ patient has fit AML. In certain embodiments, an MRD+ patient has unfit AML. The methods provided herein can covert MRD+ patients to MRD− patients. The methods provided herein can also increase the relapse-free survival time (e.g., the median relapse-free survival time) in MRD+ patients.

In some embodiments, at least about 80% of cells of the hematological malignancy are CD123+ (e.g, as determined by local flow cytometry or immunohistochemistry).

In some embodiments, it has been determined prior to the administration that at least 80% of cells of the hematological malignancy are CD123-positive (e.g, as determined by local flow cytometry or immunohistochemistry).

In certain instances, the cancer has not previously been treated.

In certain instances, the human subject has received at least one prior treatment regimen for the cancer. In certain instances, the human subject has received one prior treatment regimen for the cancer. In certain instances, the human subject has received two prior treatment regimens for the cancer. In certain instances, the human subject has received two prior treatment regimens for the cancer. In certain instances, the human subject has received no more than six prior treatment regimens for the cancer. In certain instances, the human subject has received at least one prior treatment, but no more than six prior treatment regimens for the cancer.

In one instance the cancer has previously been treated with a BCL-2 inhibitor. In one instance, the cancer has not previously been treated with a BCL-2 inhibitor (i.e., the patient is "BCL-2 inhibitor naive").

In one instance the cancer has previously been treated with venetoclax. In one instance, the cancer has not previously been treated with venetoclax (i.e., the patient is "venetoclax naive").

In one instance the cancer has previously been treated with a hypomethylating agent. In one instance, the cancer has not previously been treated with a hypomethylating agent (i.e., the patient is "hypomethylating agent naive").

In one instance the cancer has previously been treated with azacitidine. In one instance, the cancer has not previously been treated with azacitidine (i.e., the patient is "azacitidine naive").

In one instance the cancer has previously been treated with decitabine. In one instance, the cancer has not previously been treated with decitabine (i.e., the patient is "decitabine naive").

VI(B). Dosing

As provided herein, an anti-CD123 immunoconjugate (e.g., IMGN632) can be administered at a particular dose and/or at particular timing intervals. Administration of anti-CD123 immunoconjugates (e.g., IMGN632) can be, for example, intravenous.

In certain embodiments, the anti-CD123 immunoconjugate (e.g., IMGN632) is administered once in a three-week (21-day) cycle. In certain embodiments, the anti-CD123 immunoconjugate (e.g., IMGN632) is administered three times in a three-week cycle, for example, wherein the first administration is on a first day (e.g, Day 1), wherein the second administration is three days after the first administration (e.g., Day 4), and wherein the third administration is four days after the second administration (e.g. Day 7) of a 21-day cycle. By way of example, when the first administration of the immunoconjugate (e.g., IMGN632) is on Day 7 of a 21-day cycle (e.g., when the immunoconjugate is administered in combination with a BCL-2 inhibitor (e.g., venetoclax)), the immunoconjugate (e.g., IMGN632) can be administered on Day 7, Day 10, and Day 14 of a 21-day cycle.

In certain embodiments, the anti-CD123 immunoconjugate (e.g., IMGN632) is administered once in a four-week (28-day) cycle. In certain embodiments, the anti-CD123 immunoconjugate (e.g., IMGN632) is administered three times in a four-week cycle, for example, wherein the first administration is on a first day (e.g, Day 1), wherein the second administration is three days after the first administration (e.g., Day 4), and wherein the third administration is four days after the second administration (e.g. Day 7) of a 28-day cycle. By way of example, when the first administration of the immunoconjugate (e.g., IMGN632) is on Day 7 of a 28-day cycle (e.g., when the immunoconjugate is administered in combination with an HMA (e.g., azacitidine) or with a BCL-2 inhibitor (e.g., venetoclax) and an HMA (e.g., azacitidine)), the immunoconjugate (e.g., IMGN632) can be administered on Day 7, Day 10, and Day 14 of a 28-day cycle.

In certain embodiments, one cycle of treatment is therapeutically effective. In certain embodiments, two cycles of treatment are therapeutically effective. In certain embodiments, one to four cycles of treatment are therapeutically effective. In certain embodiments, two to twelve cycles of treatment In some embodiments, patients can be treated for one cycle (e.g., a 21-day cycle or a 28-day cycle), e.g., wherein the immunoconjugate is administered once in the cycle or three times in the cycle. In some embodiments, patients can be treated for at least two cycles (e.g., 21-day cycles or 28-day cycles), e.g., wherein the immunoconjugate is administered once per cycle or three times per cycle. In some embodiments, patients can be treated for at least three cycles (e.g., 21-day cycles or 28-day cycles), e.g., wherein the immunoconjugate is administered once per cycle or three times per cycle. In some embodiments, patients can be treated for at least four cycles (e.g., 21-day cycles or 28-day cycles), e.g., wherein the immunoconjugate is administered once per cycle or three times per cycle. In some embodiments, patients can be treated for at least five cycles (e.g., 21-day cycles or 28-day cycles), e.g., wherein the immunoconjugate is administered once per cycle or three times per cycle. In some embodiments, patients can be treated for at least six cycles (e.g., 21-day cycles or 28-day cycles), e.g., wherein the immunoconjugate is administered once per cycle or three times per cycle. In some embodiments, patients can be treated for at least seven cycles (e.g., 21-day cycles or 28-day cycles), e.g., wherein the immunoconjugate is administered once per cycle or three times per cycle. In some embodiments, patients can be treated for at least eight cycles (e.g., 21-day cycles or 28-day cycles), e.g., wherein the immunoconjugate is administered once per cycle or three times per cycle. In some embodiments, patients can be treated for at least nine cycles (e.g., 21-day cycles or 28-day cycles), e.g., wherein the immunoconjugate is administered once per cycle or three times per cycle. In some embodiments, patients can be treated for at least ten cycles (e.g., 21-day cycles or 28-day cycles), e.g., wherein the immunoconjugate is administered once per cycle or three times per cycle. In some embodiments, patients can be treated for at least eleven cycles (e.g., 21-day cycles or 28-day cycles), e.g., wherein the immunoconjugate is administered once per cycle or three times per cycle. In some embodiments, patients can be treated for at least twelve cycles (e.g., 21-day cycles or 28-day cycles), e.g., wherein the immunoconjugate is administered once per cycle or three times per cycle.

In some embodiments, patients can be treated for one to ten cycles (e.g., 21-day cycles or 28-day cycles), e.g., wherein the immunoconjugate is administered once per cycle or three times cycle. In some embodiments, patients can be treated for two to ten cycles (e.g., 21-day cycles or 28-day cycles), e.g., wherein the immunoconjugate is administered once per cycle or three times per cycle. In some embodiments, patients can be treated for three to ten cycles (e.g., 21-day cycles or 28-day cycles), e.g., wherein the immunoconjugate is administered once per cycle or three times per cycle. In some embodiments, patients can be treated for four to ten cycles (e.g., 21-day cycles or 28-day cycles), e.g., wherein the immunoconjugate is administered once per cycle or three times per cycle. In some embodiments, patients can be treated for five to ten cycles (e.g., 21-day cycles or 28-day cycles), e.g., wherein the immunoconjugate is administered once per cycle or three times per cycle.

In some embodiments, patients can be treated for one to twelve cycles (e.g., 21-day cycles or 28-day cycles), e.g., wherein the immunoconjugate is administered once per cycle or three times per cycle. In some embodiments, patients can be treated for two to twelve cycles (e.g., 21-day cycles or 28-day cycles), e.g., wherein the immunoconjugate is administered once per cycle or three times per cycle. In some embodiments, patients can be treated for three to twelve cycles (e.g., 21-day cycles or 28-day cycles), e.g., wherein the immunoconjugate is administered once per cycle or three times per cycle. In some embodiments, patients can be treated for four to twelve cycles (e.g., 21-day cycles or 28-day cycles), e.g., wherein the immunoconjugate is administered once per cycle or three times per cycle. In some embodiments, patients can be treated for five to twelve cycles (e.g., 21-day cycles or 28-day cycles), e.g., wherein the immunoconjugate is administered once per cycle or three times per.

In certain embodiments, about 0.015 mg/kg to about 0.09 mg/kg of an anti-CD123 immunoconjugate (e.g., IMGN632) is administered once in a three-week (21-day) cycle. In certain embodiments, about 0.015 mg/kg to about 0.09 mg/kg of an anti-CD123 immunoconjugate (e.g., IMGN632) is administered once in a four-week (28-day) cycle. In certain embodiments, about 0.015 mg/kg to about 0.135 mg/kg of an anti-CD123 immunoconjugate (e.g., IMGN632) is administered once in a three-week (21-day) cycle. In certain embodiments, about 0.015 mg/kg to about 0.135 mg/kg of an anti-CD123 immunoconjugate (e.g., IMGN632) is administered once in a four-week (28-day) cycle.

In certain embodiments, 0.015 mg/kg to about 0.045 mg/kg of an anti-CD123 immunoconjugate (e.g., IMGN632) is administered once in a three-week (21-day) cycle. In certain embodiments, about 0.03 mg/kg of an anti-CD123 immunoconjugate (e.g., IMGN632) is administered once in a three-week (21-day) cycle. In certain embodiments, 0.015 mg/kg to about 0.045 mg/kg of an anti-CD123 immunoconjugate (e.g., IMGN632) is administered once in a four-week (28-day) cycle. In certain embodiments, about 0.03 mg/kg of an anti-CD123 immunoconjugate (e.g., IMGN632) is administered once in a four-week (28-day) cycle.

In certain embodiments, 0.045 mg/kg to about 0.09 mg/kg of an anti-CD123 immunoconjugate (e.g., IMGN632) is administered once in a three-week (21-day) cycle. In certain embodiments, 0.045 mg/kg to about 0.09 mg/kg of an anti-CD123 immunoconjugate (e.g., IMGN632) is administered once in a four-week (28-day) cycle.

In certain embodiments, 0.045 mg/kg to about 0.135 mg/kg of an anti-CD123 immunoconjugate (e.g., IMGN632) is administered once in a three-week (21-day) cycle. In certain embodiments, 0.045 mg/kg to about 0.135 mg/kg of an anti-CD123 immunoconjugate (e.g., IMGN632) is administered once in a four-week (28-day) cycle In certain embodiments, about 0.015 mg/kg of the anti-CD123 immunoconjugate (e.g., IMGN632) is administered once in a three-week (21-day) or four week (28-day) cycle. In certain embodiments, about 0.03 mg/kg of the anti-CD123 immunoconjugate (e.g., IMGN632) is administered once in a three-week (21-day) or four week (28-day) cycle. In certain embodiments, about 0.045 mg/kg of the anti-CD123 immunoconjugate (e.g., IMGN632) is administered once in a three-week (21-day) or four week (28-day) cycle. In certain embodiments, about 0.09 mg/kg of the anti-CD123 immunoconjugate (e.g., IMGN632) is administered once in a three-week (21-day) or four week (28-day) cycle. In certain embodiments, about 0.135 mg/kg of the anti-CD123 immunoconjugate (e.g., IMGN632) is administered once in a three-week (21-day) or four week (28-day) cycle.

In certain embodiments, a total dose of 0.045 mg/kg to about 0.18 mg/kg of an anti-CD123 immunoconjugate (e.g., IMGN632) is administered over the course of a three-week cycle or a four-week cycle, wherein the total dose is divided into three separate administrations (e.g., on Days 1, 4, and 8 or Days 7, 10, and 14 of the cycle). Thus, in certain embodiments, about 0.015 mg/kg to about 0.09 mg/kg of an anti-CD123 immunoconjugate (e.g., IMGN632) is administered three times in a three-week cycle or a four-week cycle, for example, on Days 1, 4, and 8 or Days 7, 10, and 14 of the cycle. In certain embodiments, about 0.015 mg/kg to about 0.135 mg/kg of an anti-CD123 immunoconjugate (e.g., IMGN632) is administered three times in a three-week cycle or a four-week cycle, for example, on Days 1, 4, and 8 or Days 7, 10, and 14 of the cycle. In certain embodiments, about 0.015 mg/kg to about 0.06 mg/kg of an anti-CD123 immunoconjugate (e.g., IMGN632) is administered three times in a three-week cycle or a 4-week cycle, for example, on Days 1, 4, and 8 or Days 7, 10, and 14 of the cycle. In certain embodiments, about 0.015 mg/kg to about 0.03 mg/kg of an anti-CD123 immunoconjugate (e.g., IMGN632) is administered three times in a three-week cycle or a four-week cycle, for example, on Days 1, 4, and 8 or Days 7, 10, and 14 of the cycle. In certain embodiments, about 0.03 mg/kg to about 0.06 mg/kg of an anti-CD123 immunoconjugate (e.g., IMGN632) is administered three times in a three-week cycle or a four-week cycle, for example, on Days 1, 4, and 8 or Days 7, 10, and 14 of the cycle.

In certain embodiments, about 0.015 mg/kg of the anti-CD123 immunoconjugate (e.g., IMGN632) is administered three times in a three-week cycle or a four-week cycle, for example, on Days 1, 4, and 8 or Days 7, 10, and 14 of the cycle. In certain embodiments, about 0.03 mg/kg of the anti-CD123 immunoconjugate (e.g., IMGN632) is administered three times in a three-week cycle or a four-week cycle, for example, on Days 1, 4, and 8 or Days 7, 10, and 14 of the cycle. In certain embodiments, about 0.06 mg/kg of the anti-CD123 immunoconjugate (e.g., IMGN632) is administered three times in a three-week cycle or a four-week cycle, for example, on Days 1, 4, and 8 or Days 7, 10, and 14 of the cycle. In certain embodiments, about 0.09 mg/kg of the anti-CD123 immunoconjugate (e.g., IMGN632) is administered three times in a three-week cycle or a four-week cycle, for example, on Days 1, 4, and 8 or Days 7, 10, and 14 of the cycle. In certain embodiments, about 0.135 mg/kg of the anti-CD123 immunoconjugate (e.g., IMGN632) is administered three times in a three-week cycle or a four-week cycle, for example, on Days 1, 4, and 8 or Days 7, 10, and 14 of the cycle.

As provided herein, a BCL-2 inhibitor can be administered at a particular dose and/or at particular timing intervals. Administration of a BCL-2 inhibitor (e.g., venetoclax) can be, for example, oral (e.g., in a tablet form).

In certain embodiments, a BCL-2 inhibitor (e.g., venetoclax) is administered at a daily dose of 400 mg. In certain embodiments, a BCL-2 inhibitor (e.g., venetoclax) is administered at a daily dose of 200 mg.

In certain embodiments, a BCL-2 inhibitor (e.g., venetoclax) is administered in a 21-day cycle. The BCL-2 inhibitor (e.g., venetoclax) can be administered, for example, on days 1-7, days 1-8, days 1-14, days 1-18, or days 1-21 of a 21-day cycle. In certain embodiments, a BCL-2 inhibitor (e.g., venetoclax) is administered in a 28-day cycle. The BCL-2 inhibitor (e.g., venetoclax) can be administered, for example, on days 1-7, days 1-8, days 1-14, days 1-18, days 1-21, or days 1-28 of a 28-day cycle.

In certain embodiments, e.g., in a first Cycle, a BCL-2 inhibitor (e.g., venetoclax) is administered orally (PO) at 100 mg on Day 1, at 200 mg on Day 2, and at 400 mg on all subsequent days of the cycle, e.g., Days 3-21 of a 21-day cycle or Days 3-28 of a 28-day cycle.

In certain embodiments, e.g., in a first Cycle, a BCL-2 inhibitor (e.g., venetoclax) is administered orally (PO) at 100 mg on Day 1, at 200 mg on Day 2, and at 400 mg on Days 3-18 of a 21-day cycle or a 28-day cycle. In certain embodiments, e.g., in a first Cycle, a BCL-2 inhibitor (e.g., venetoclax) is administered orally (PO) at 100 mg on Day 1, at 200 mg on Day 2, and at 400 mg on Days 3-14 of a 21-day cycle or a 28-day cycle. In certain embodiments, e.g., in a first Cycle, a BCL-2 inhibitor (e.g., venetoclax) is administered orally (PO) at 100 mg on Day 1, at 200 mg on Day 2, and at 400 mg on Days 3-8 of a 21-day cycle or a 28-day cycle. In certain embodiments, e.g., in a first Cycle, a BCL-2 inhibitor (e.g., venetoclax) is administered orally (PO) at 100 mg on Day 1, at 200 mg on Day 2, and at 400 mg on Days 3-7 of a 21-day cycle or a 28-day cycle.

In certain embodiments, e.g., in a first Cycle, a BCL-2 inhibitor (e.g., venetoclax) is administered orally (PO) at 100 mg on Day 1 and at 200 mg on all subsequent days of a cycle, e.g., Days 2-21 of a 21-day cycle or Days 2-28 of a 28-day cycle. In certain embodiments, e.g., in a first Cycle, a BCL-2 inhibitor (e.g., venetoclax) is administered orally (PO) at 100 mg on Day 1 and at 200 mg on Days 2-18 of a 21-day cycle or a 28-day cycle. In certain embodiments, e.g., in a first Cycle, a BCL-2 inhibitor (e.g., venetoclax) is administered orally (PO) at 100 mg on Day 1 and at 200 mg on Days 2-14 of a 21-day cycle or a 28-day cycle. In certain embodiments, e.g., in a first Cycle, a BCL-2 inhibitor (e.g., venetoclax) is administered orally (PO) at 100 mg on Day 1 and at 200 mg on Days 2-8 of a 21-day cycle or a 28-day cycle. In certain embodiments, e.g., in a first Cycle, a BCL-2 inhibitor (e.g., venetoclax) is administered orally (PO) at 100 mg on Day 1 and at 200 mg on Days 2-7 of a 21-day cycle or a 28-day cycle.

In certain embodiments, administration of an anti-CD123 immunoconjugate (e.g., IMGN632) is initiated on Day 7 after a seventh BCL-2 inhibitor (e.g., venetoclax) dose.

A cycle (e.g., a 21-day cycle or a 28-day cycle) of administration of an anti-CD123 immunoconjugate and a BCL-2 inhibitor (e.g. ventoclax) can be repeated, e.g., for 2-12 cycles.

In certain embodiments, a BCL-2 inhibitor (e.g., venetoclax) is administered daily. In certain embodiments, a BCL-2 inhibitor (e.g., venetoclax) is administered orally. In certain embodiments, a BCL-2 inhibitor (e.g., venetoclax) is administered orally daily.

In certain embodiments, 400 mg of a BCL-2 inhibitor (e.g., venetoclax) is administered daily. In certain embodiments, 400 mg of a BCL-2 inhibitor (e.g., venetoclax) is administered orally. In certain embodiments, 400 mg of a BCL-2 inhibitor (e.g., venetoclax) is administered orally daily.

After administration of an anti-CD123 immunoconjugate and a BCL-2 inhibitor (e.g., venetoclax), the anti-CD123 immunoconjugate (e.g., IMGN632) can be administered as a maintenance therapy.

As provided herein, an HMA can be administered at a particular dose and/or at particular timing intervals. Administration of an HMA (e.g., azacitidine or decitabine) can be, for example, subcutaneous or intravenous.

In certain embodiments, azacitidine can be administered at 75 mg/m$^2$ subcutaneously (SC) or intravenous (IV). In certain embodiments, azacitidine can be administered at 75 mg/m$^2$ subcutaneously (SC) or intravenous (IV) daily for 7 consecutive days. In certain embodiments, azacitidine can be administered at 75 mg/m$^2$ subcutaneously (SC) or intravenous (IV) daily for 7 consecutive days in a 28-day cycle. In certain embodiments, azacitidine can be administered at 75 mg/m$^2$ subcutaneously (SC) or intravenous (IV) daily for 5 consecutive days. In certain embodiments, azacitidine can be administered at 75 mg/m$^2$ subcutaneously (SC) or intravenous (IV) daily for 5 consecutive days in a 28-day cycle In certain embodiments, an HMA (e.g., azacitidine) is administered at a dose of 75 mg/m$^2$. In certain embodiments, an HMA (e.g., azacitidine) is administered at a dose of 100 mg/m$^2$.

In certain embodiments, an HMA (e.g., azacitidine) is administered daily for 7 days every 4 weeks. In certain embodiments, an HMA (e.g., azacitidine) is administered daily for 5 days every 4 weeks.

In certain embodiments, 75 mg/m$^2$ of an HMA (e.g., azacitidine) is administered daily for 7 days every 4 weeks. In certain embodiments, 100 mg/m$^2$ of an HMA (e.g., azacitidine) is administered daily for 7 days every 4 weeks. In certain embodiments, 75 mg/m$^2$ of an HMA (e.g., azacitidine) is administered daily for 5 days every 4 weeks. In certain embodiments, 100 mg/m$^2$ of an HMA (e.g., azacitidine) is administered daily for 5 days every 4 weeks.

In certain embodiments, 75 mg/m$^2$ of an HMA (e.g., azacitidine) is administered subcutaneously or intravenously daily for 7 days every 4 weeks. In certain embodiments, 100 mg/m$^2$ of an HMA (e.g., azacitidine) is administered subcutaneously or intravenously daily for 7 days every 4 weeks. In certain embodiments, 75 mg/m$^2$ of an HMA (e.g., azacitidine) is administered subcutaneously or intravenously daily for 5 days every 4 weeks. In certain embodiments, 100 mg/m$^2$ of an HMA (e.g., azacitidine) is administered subcutaneously or intravenously daily for 5 days every 4 weeks.

After administration of an anti-CD123 immunoconjugate and an HMA (e.g., azacitidine), the anti-CD123 immunoconjugate (e.g., IMGN632) can be administered as a maintenance therapy.

In certain embodiments, an HMA (e.g., decitabine) is administered at a dose of 15 mg/m$^2$. In certain embodiments, an HMA (e.g., decitabine) is administered at a dose of 20 mg/m$^2$.

In certain embodiments, an HMA (e.g., decitabine) is administered by intravenous infusion over 3 hours, repeated every 8 hours for 3 days, and repeated every six weeks. In certain embodiments, an HMA (e.g., decitabine) is administered by intravenous infusion over 1 hour for 5 days and repeated every four weeks.

In certain embodiments, 15 mg/m$^2$ of an HMA (e.g., decitabine) is administered by intravenous infusion over 3 hours, repeated every 8 hours for 3 days, and repeated every six weeks. In certain embodiments, 20 mg/m$^2$ of an HMA (e.g., decitabine) is administered by intravenous infusion over 1 hour for 5 days and repeated every four weeks.

After administration of an anti-CD123 immunoconjugate and an HMA (e.g., decitabine), the anti-CD123 immunoconjugate (e.g., IMGN632) can be administered as a maintenance therapy.

In certain embodiments, 0.015 mg/kg to about 0.09 mg/kg (e.g., 0.015, 0.045, or 0.09 mg/kg) of an anti-CD123 immunoconjugate (e.g., IMGN632) is administered once every three or four weeks and 400 mg of a BCL-2 inhibitor (e.g., venetoclax) is administered daily. In certain embodiments, 0.03 mg/kg of an anti-CD123 immunoconjugate (e.g., IMGN632) is administered once every three or four weeks and 400 mg of a BCL-2 inhibitor (e.g., venetoclax) is administered daily. In certain embodiments, 0.015 mg/kg to about 0.09 mg/kg (e.g., 0.015, 0.045, or 0.09 mg/kg) of an anti-CD123 immunoconjugate (e.g., IMGN632) is administered intravenously once every three or four weeks and 400 mg of a BCL-2 inhibitor (e.g., venetoclax) is administered orally daily. In certain embodiments, 0.03 mg/kg of an anti-CD123 immunoconjugate (e.g., IMGN632) is administered intravenously once every three or four weeks and 400 mg of a BCL-2 inhibitor (e.g., venetoclax) is administered orally daily. The BCL-2 inhibitor (e.g., venetoclax) can be administered daily on days 1-7, days 1-8, days 1-14, days 1-18, or days 1-21 of a 21-day (three-week) cycle. The BCL-2 inhibitor (e.g., venetoclax) can be administered daily on days 1-7, days 1-8, days 1-14, days 1-18, days 1-21, or days 1-28 of a 28-day (four-week) cycle.

In certain embodiments, 0.015 mg/kg to about 0.135 mg/kg (e.g., 0.135 mg/kg) of an anti-CD123 immunoconjugate (e.g., IMGN632) is administered once every three or four weeks and 400 mg of a BCL-2 inhibitor (e.g., venetoclax) is administered daily. In certain embodiments, 0.03 mg/kg of an anti-CD123 immunoconjugate (e.g., IMGN632) is administered once every three or four weeks and 400 mg of a BCL-2 inhibitor (e.g., venetoclax) is administered daily. In certain embodiments, 0.015 mg/kg to about 0.135 mg/kg (e.g., 0.135 mg/kg) of an anti-CD123 immunoconjugate (e.g., IMGN632) is administered intravenously once every three or four weeks and 400 mg of a BCL-2 inhibitor (e.g., venetoclax) is administered orally daily. In certain embodiments, 0.03 mg/kg of an anti-CD123 immunoconjugate (e.g., IMGN632) is administered intravenously once every three or four weeks and 400 mg of a BCL-2 inhibitor (e.g., venetoclax) is administered orally daily. In certain embodiments, 0.03 mg/kg of an anti-CD123 immunoconjugate (e.g., IMGN632) is administered intravenously once every three or four weeks and 400 mg of a BCL-2 inhibitor (e.g., venetoclax) is administered orally daily. The BCL-2 inhibitor (e.g., venetoclax) can be administered daily on days 1-7, days 1-8, days 1-14, days 1-18, or days 1-21 of a 21-day (three-week) cycle. The BCL-2 inhibitor (e.g., venetoclax) can be administered daily on days 1-7, days 1-8, days 1-14, days 1-18, days 1-21, or days 1-28 of a 28-day (four-week) cycle.

In certain embodiments, a total dose of 0.045 mg/kg to about 0.18 mg/kg of an anti-CD123 immunoconjugate (e.g., IMGN632) is administered over the course of a three-week cycle, wherein the total dose is divided into three separate administrations (e.g., on Days 1, 4, and 8 or Days 7, 10, and 14 of the cycle), and a BCL-2 inhibitor (e.g., venetoclax) is administered daily. Thus, in certain embodiments, about 0.015 mg/kg to about 0.06 mg/kg (e.g., 0.015, 0.03, or 0.06 mg/kg) of an anti-CD123 immunoconjugate (e.g., IMGN632) is administered three times in a 21-day cycle (e.g., on days 7, 10, and 14 of the 21-day cycle) a BCL-2 inhibitor (e.g., venetoclax) is administered daily. In certain embodiments, about 0.015 mg/kg to about 0.06 mg/kg (e.g., 0.015, 0.03, or 0.06 mg/kg) of an anti-CD123 immunoconjugate (e.g., IMGN632) is administered intravenously three times in a 21-day cycle (e.g., on days 7, 10, and 14 of the 21-day cycle) and a BCL-2 inhibitor (e.g., venetoclax) is administered orally daily. The BCL-2 inhibitor (e.g., venetoclax) can be administered at a dose of 100 mg, 200 mg, and/or 400 mg. The BCL-2 inhibitor (e.g., venetoclax) can be administered at a dose of 100 mg on Day 1, 200 mg on Day 2, and 400 mg on Days 3-21 of a 21-day cycle (e.g., a first 21-day cycle). The BCL-2 inhibitor (e.g., venetoclax) can be administered at a dose of 100 mg on Day 1 and 200 mg on Days 2-21 of a 21-day cycle (e.g., a first 21-day cycle). The BCL-2 inhibitor (e.g., venetoclax) can be administered as a daily oral dose of 400 mg on all days (e.g., Days 1-21) of the 21-day cycle. The BCL-2 inhibitor (e.g., venetoclax) can be administered as a daily oral dose of 200 mg on all days (e.g., Days 1-21) of the 21-day cycle.

In certain embodiments, 0.015 mg/kg to about 0.09 mg/kg (e.g., 0.015, 0.045, or 0.09 mg/kg) of an anti-CD123 immunoconjugate (e.g., IMGN632) is administered once every four weeks and 75 mg/m$^2$ or 100 mg/m$^2$ of an HMA (e.g., azacitidine) is administered daily for 7 days every 4 weeks. In certain embodiments, 0.03 mg/kg of an anti-CD123 immunoconjugate (e.g., IMGN632) is administered once every four weeks and 75 mg/m$^2$ or 100 mg/m$^2$ of an HMA (e.g., azacitidine) is administered daily for 7 days every 4 weeks. In certain embodiments, 0.015 mg/kg to about 0.09 mg/kg (e.g., 0.015, 0.045, or 0.09 mg/kg) of an anti-CD123 immunoconjugate (e.g., IMGN632) is administered intravenously once every four weeks and 75 mg/m$^2$ or 100 mg/m$^2$ of an HMA (e.g., azacitidine) is administered subcutaneously or intravenously daily for 7 days every 4 weeks. In certain embodiments, 0.03 mg/kg of an anti-CD123 immunoconjugate (e.g., IMGN632) is administered intravenously once every four weeks and 75 mg/m$^2$ or 100 mg/m$^2$ of an HMA (e.g., azacitidine) is administered subcutaneously or intravenously daily for 7 days every 4 weeks.

In certain embodiments, 0.015 mg/kg to about 0.09 mg/kg (e.g., 0.015, 0.045, or 0.09 mg/kg) of an anti-CD123 immunoconjugate (e.g., IMGN632) is administered once every four weeks and 75 mg/m$^2$ or 100 mg/m$^2$ of an HMA (e.g., azacitidine) is administered daily for 5 days every 4 weeks. In certain embodiments, 0.03 mg/kg of an anti-CD123 immunoconjugate (e.g., IMGN632) is administered once every four weeks and 75 mg/m$^2$ or 100 mg/m$^2$ of an HMA (e.g., azacitidine) is administered daily for 5 days every 4 weeks. In certain embodiments, 0.015 mg/kg to about 0.09 mg/kg (e.g., 0.015, 0.045, or 0.09 mg/kg) of an anti-CD123 immunoconjugate (e.g., IMGN632) is administered intravenously once every four weeks and 75 mg/m$^2$ or 100 mg/m$^2$ of an HMA (e.g., azacitidine) is administered subcutaneously or intravenously daily for 5 days every 4 weeks. In certain embodiments, 0.03 mg/kg of an anti-CD123 immunoconjugate (e.g., IMGN632) is administered intravenously once every four weeks and 75 mg/m$^2$ or 100 mg/m$^2$ of an HMA (e.g., azacitidine) is administered subcutaneously or intravenously daily for 5 days every 4 weeks.

In certain embodiments, 0.015 mg/kg to about 0.135 mg/kg (e.g., 0.135 mg/kg) of an anti-CD123 immunoconjugate (e.g., IMGN632) is administered once every four weeks and 75 mg/m$^2$ or 100 mg/m$^2$ of an HMA (e.g., azacitidine) is administered daily for 7 days every 4 weeks. In certain embodiments, 0.015 mg/kg to about 0.135 mg/kg (e.g., 0.135 mg/kg) of an anti-CD123 immunoconjugate (e.g., IMGN632) is administered intravenously once every four weeks and 75 mg/m$^2$ or 100 mg/m$^2$ of an HMA (e.g., azacitidine) is administered subcutaneously or intravenously daily for 7 days every 4 weeks.

In certain embodiments, 0.015 mg/kg to about 0.135 mg/kg (e.g., 0.135 mg/kg) of an anti-CD123 immunoconjugate (e.g., IMGN632) is administered once every four weeks and 75 mg/m$^2$ or 100 mg/m$^2$ of an HMA (e.g., azacitidine) is administered daily for 5 days every 4 weeks. In certain embodiments, 0.015 mg/kg to about 0.135 mg/kg (e.g., 0.135 mg/kg) of an anti-CD123 immunoconjugate (e.g., IMGN632) is administered intravenously once every four weeks and 75 mg/m$^2$ or 100 mg/m$^2$ of an HMA (e.g., azacitidine) is administered subcutaneously or intravenously daily for 5 days every 4 weeks.

In certain embodiments, a total dose of 0.045 mg/kg to about 0.18 mg/kg of an anti-CD123 immunoconjugate (e.g., IMGN632) is administered over the course of a four-week cycle, wherein the total dose is divided into three separate administrations (e.g., on Days 1, 4, and 8 or Days 7, 10, and 14 of the cycle), and 75 mg/m$^2$ or 100 mg/m$^2$ of an HMA (e.g., azacitidine) is administered daily for 7 days every 4 weeks. In certain embodiments, about 0.015 mg/kg to about 0.06 mg/kg (e.g., 0.015, 0.03, or 0.06 mg/kg) of an anti-CD123 immunoconjugate (e.g., IMGN632) is administered three times in a 21-day cycle (e.g., on days 7, 10, and 14 of the 28-day cycle) and and 75 mg/m$^2$ or 100 mg/m$^2$ of an HMA (e.g., azacitidine) is administered daily for 7 days every 4 weeks. In certain embodiments, about 0.015 mg/kg to about 0.06 mg/kg (e.g., 0.015, 0.03, or 0.06 mg/kg) of an anti-CD123 immunoconjugate (e.g., IMGN632) is administered intravenously three times in a 28-day cycle (e.g., on days 7, 10, and 14 of the 28-day cycle) and 75 mg/m$^2$ or 100 mg/m$^2$ of an HMA (e.g., azacitidine) is administered subcutaneously or intravenously daily for 7 days every 4 weeks.

In certain embodiments, about 0.015 mg/kg to about 0.09 mg/kg (e.g., 0.015, 0.045, or 0.09 mg/kg) of an anti-CD123 immunoconjugate (e.g., IMGN632) is administered once every three weeks and 15 mg/m$^2$ of an HMA (e.g., decitabine) is administered over 3 hours, repeated every 8 hours for 3 days, and repeated every six weeks. In certain embodiments, about 0.03 mg/kg of an anti-CD123 immunoconjugate (e.g., IMGN632) is administered once every three weeks and 15 mg/m$^2$ of an HMA (e.g., decitabine) is administered over 3 hours, repeated every 8 hours for 3 days, and repeated every six weeks. In certain embodiments, about 0.015 mg/kg to about 0.09 mg/kg (e.g., 0.015, 0.045, or 0.09 mg/kg) of an anti-CD123 immunoconjugate (e.g., IMGN632) is administered intravenously once every three weeks and 15 mg/m$^2$ of an HMA (e.g., decitabine) is administered by intravenous infusion over 3 hours, repeated every 8 hours for 3 days, and repeated every six weeks. In certain embodiments, about 0.03 mg/kg of an anti-CD123 immunoconjugate (e.g., IMGN632) is administered intravenously once every three weeks and 15 mg/m$^2$ of an HMA (e.g., decitabine) is administered by intravenous infusion over 3 hours, repeated every 8 hours for 3 days, and repeated every six weeks.

In certain embodiments, about 0.015 mg/kg to about 0.135 mg/kg (e.g., 0.135 mg/kg) of an anti-CD123 immunoconjugate (e.g., IMGN632) is administered once every three weeks and 15 mg/m² of an HMA (e.g., decitabine) is administered over 3 hours, repeated every 8 hours for 3 days, and repeated every six weeks. In certain embodiments, about 0.015 mg/kg to about 0.135 mg/kg (e.g., 0.135 mg/kg) of an anti-CD123 immunoconjugate (e.g., IMGN632) is administered intravenously once every three weeks and 15 mg/m² of an HMA (e.g., decitabine) is administered by intravenous infusion over 3 hours, repeated every 8 hours for 3 days, and repeated every six weeks.

In certain embodiments, a total dose of 0.045 mg/kg to about 0.18 mg/kg of an anti-CD123 immunoconjugate (e.g., IMGN632) is administered over the course of a four-week cycle, wherein the total dose is divided into three separate administrations (e.g., on Days 1, 4, and 8 or Days 7, 10, and 14 of the cycle), and 15 mg/m² of an HMA (e.g., decitabine) is administered over 3 hours, repeated every 8 hours for 3 days, and repeated every six weeks. In certain embodiments, about 0.015 mg/kg to about 0.09 mg/kg (e.g., 0.015, 0.03, or 0.06 mg/kg) of an anti-CD123 immunoconjugate (e.g., IMGN632) is administered three times in a 21-day cycle (e.g., on days 7, 10, and 14 of the 21-day cycle) and 15 mg/m² of an HMA (e.g., decitabine) is administered over 3 hours, repeated every 8 hours for 3 days, and repeated every six weeks. In certain embodiments, about 0.015 mg/kg to about 0.135 mg/kg (e.g., 0.135 mg/kg) of an anti-CD123 immunoconjugate (e.g., IMGN632) is administered three times in a 21-day cycle (e.g., on days 7, 10, and 14 of the 21-day cycle) and 15 mg/m² of an HMA (e.g., decitabine) is administered over 3 hours, repeated every 8 hours for 3 days, and repeated every six weeks. In certain embodiments, about 0.015 mg/kg to about 0.06 mg/kg (e.g., 0.015, 0.045, or 0.09 mg/kg) of an anti-CD123 immunoconjugate (e.g., IMGN632) is administered intravenously three times in a 21-day cycle (e.g., on days 7, 10, and 14 of the 21-day cycle) and 15 mg/m² of an HMA (e.g., decitabine) is administered by intravenous infusion over 3 hours, repeated every 8 hours for 3 days, and repeated every six weeks.

In certain embodiments, about 0.015 mg/kg to about 0.09 mg/kg (e.g., 0.015, 0.045, or 0.09 mg/kg) of an anti-CD123 immunoconjugate (e.g., IMGN632) is administered once every four weeks and 20 mg/m² of an HMA (e.g., decitabine) is administered by over 1 hour for 5 days and repeated every four weeks. In certain embodiments, about 0.03 mg/kg of an anti-CD123 immunoconjugate (e.g., IMGN632) is administered once every four weeks and 20 mg/m² of an HMA (e.g., decitabine) is administered by over 1 hour for 5 days and repeated every four weeks. In certain embodiments, about 0.015 mg/kg to about 0.09 mg/kg (e.g., 0.015, 0.045, or 0.09 mg/kg) of an anti-CD123 immunoconjugate (e.g., IMGN632) is administered intravenously once every four weeks and 20 mg/m² of an HMA (e.g., decitabine) is administered by intravenous infusion over 1 hour for 5 days and repeated every four weeks. In certain embodiments, about 0.03 mg/kg of an anti-CD123 immunoconjugate (e.g., IMGN632) is administered intravenously once every four weeks and 20 mg/m² of an HMA (e.g., decitabine) is administered by intravenous infusion over 1 hour for 5 days and repeated every four weeks.

In certain embodiments, about 0.015 mg/kg to about 0.135 mg/kg (e.g., 0.135 mg/kg) of an anti-CD123 immunoconjugate (e.g., IMGN632) is administered once every four weeks and 20 mg/m² of an HMA (e.g., decitabine) is administered by over 1 hour for 5 days and repeated every four weeks. In certain embodiments, about 0.015 mg/kg to about 0.135 mg/kg (e.g., 0.135 mg/kg) of an anti-CD123 immunoconjugate (e.g., IMGN632) is administered intravenously once every four weeks and 20 mg/m² of an HMA (e.g., decitabine) is administered by intravenous infusion over 1 hour for 5 days and repeated every four weeks.

In certain embodiments, a total dose of 0.045 mg/kg to about 0.18 mg/kg of an anti-CD123 immunoconjugate (e.g., IMGN632) is administered over the course of a four-week cycle, wherein the total dose is divided into three separate administrations (e.g., on Days 1, 4, and 8 or Days 7, 10, and 14 of the cycle), and 20 mg/m² of an HMA (e.g., decitabine) is administered over 1 hour for 5 days and repeated every four weeks. In certain embodiments, about 0.015 mg/kg to about 0.06 mg/kg (e.g., 0.015, 0.03, or 0.06 mg/kg) of an anti-CD123 immunoconjugate (e.g., IMGN632) is administered three times in a 28-day cycle (e.g., on days 7, 10, and 14 of the 21-day cycle) and 20 mg/m² of an HMA (e.g., decitabine) is administered over 1 hour for 5 days and repeated every four weeks. In certain embodiments, about 0.015 mg/kg to about 0.06 mg/kg (e.g., 0.015, 0.03, or 0.06 mg/kg) of an anti-CD123 immunoconjugate (e.g., IMGN632) is administered intravenously three times in a 28-day cycle (e.g., on days 7, 10, and 14 of the 21-day cycle) and 20 mg/m² of an HMA (e.g., decitabine) is administered by intravenous infusion over 1 hour for 5 days and repeated every four weeks.

In certain embodiments, 0.015 mg/kg to about 0.09 mg/kg (e.g., 0.015, 0.045, or 0.09 mg/kg) of an anti-CD123 immunoconjugate (e.g., IMGN632) is administered once every four weeks, 100, 200, and/or 400 mg of a BCL-2 inhibitor (e.g., venetoclax) is administered daily (e.g., 100 mg on Day 1, 200 my on Day 2, and 400 mg on Days 3-28 in Cycle 1 and 400 mg daily on Days 1-28 in subsequent cycles), and 75 mg/m² or 100 mg/m² of an HMA (e.g., azacitidine) is administered daily (e.g., on days 1-7). In certain embodiments, 0.03 mg/kg of an anti-CD123 immunoconjugate (e.g., IMGN632) is administered once every four weeks, 100, 200, and/or 400 mg of a BCL-2 inhibitor (e.g., venetoclax) is administered daily (e.g., 100 mg on Day 1, 200 my on Day 2, and 400 mg on Days 3-28 in Cycle 1 and 400 mg daily on Days 1-28 in subsequent cycles), and 75 mg/m² or 100 mg/m² of an HMA (e.g., azacitidine) is administered daily (e.g., on days 1-7). In certain embodiments, 0.015 mg/kg to about 0.09 mg/kg (e.g., 0.015, 0.045, or 0.09 mg/kg) of an anti-CD123 immunoconjugate (e.g., IMGN632) is administered intravenously once every four weeks, 100, 200, and/or 400 mg of a BCL-2 inhibitor (e.g., venetoclax) is administered orally daily (e.g., 100 mg on Day 1, 200 my on Day 2, and 400 mg on Days 3-28 in Cycle 1 and 400 mg daily on Days 1-28 in subsequent cycles), and 75 mg/m² or 100 mg/m² of an HMA (e.g., azacitidine) is administered subcutaneously or intravenously daily for 7 days (e.g., on days 1-7). In certain embodiments, 0.03 mg/kg of an anti-CD123 immunoconjugate (e.g., IMGN632) is administered intravenously once every four weeks, 100, 200, and/or 400 mg of a BCL-2 inhibitor (e.g., venetoclax) is administered orally daily (e.g., 100 mg on Day 1, 200 my on Day 2, and 400 mg on Days 3-28 in Cycle 1 and 400 mg daily on Days 1-28 in subsequent cycles), and 75 mg/m² or 100 mg/m² of an HMA (e.g., azacitidine) is administered subcutaneously or intravenously daily for 7 days (e.g., on days 1-7).

In certain embodiments, 0.015 mg/kg to about 0.09 mg/kg (e.g., 0.015, 0.03, 0.045, or 0.09 mg/kg) of an anti-CD123 immunoconjugate (e.g., IMGN632) is administered once every four weeks, 100, 200, and/or 400 mg of a BCL-2 inhibitor (e.g., venetoclax) is administered daily (e.g., 100 mg on Day 1, 200 my on Day 2, and 400 mg on Days 3-7, 3-8, 3-14, 3-18 or 3-21, or 3-28 in Cycle 1 and 400 mg daily on Days 1-7, 1-8, 1-14, 1-18, 1-21, or 1-28 in subsequent cycles), and 75 mg/m² or 100 mg/m² of an HMA (e.g., azacitidine) is administered daily (e.g., on days 1-5 or 1-7). In certain embodiments, 0.015 mg/kg to about 0.09 mg/kg (e.g., 0.015, 0.03, 0.045, or 0.09 mg/kg) of an anti-CD123 immunoconjugate (e.g., IMGN632) is administered intravenously once every four weeks, 100, 200, and/or 400 mg of a BCL-2 inhibitor (e.g., venetoclax) is administered orally daily (e.g., 100 mg on Day 1, 200 my on Day 2, and 400 mg on Days 3-7, 3-8, 3-14, 3-18 or 3-21, or 3-28 in Cycle 1 and 400 mg daily on Days 1-7, 1-8, 1-14, 1-18, 1-21, or 1-28 in subsequent cycles), and 75 mg/m² or 100 mg/m² of an HMA (e.g., azacitidine) is administered subcutaneously or intravenously daily for 7 days (e.g., on days 1-5 or 1-7).

In certain embodiments, 0.015 mg/kg to about 0.135 mg/kg (e.g., 0.135 mg/kg) of an anti-CD123 immunoconjugate (e.g., IMGN632) is administered once every four weeks, 100, 200, and/or 400 mg of a BCL-2 inhibitor (e.g., venetoclax) is administered daily (e.g., 100 mg on Day 1, 200 my on Day 2, and 400 mg on Days 3-28 in Cycle 1 and 400 mg daily on Days 1-28 in subsequent cycles), and 75 mg/m² or 100 mg/m² of an HMA (e.g., azacitidine) is administered daily (e.g., on days 1-7). In certain embodiments, 0.015 mg/kg to about 0.135 mg/kg (e.g., 0.135 mg/kg) of an anti-CD123 immunoconjugate (e.g., IMGN632) is administered intravenously once every four weeks, 100, 200, and/or 400 mg of a BCL-2 inhibitor (e.g., venetoclax) is administered orally daily (e.g., 100 mg on Day 1, 200 my on Day 2, and 400 mg on Days 3-28 in Cycle 1 and 400 mg daily on Days 1-28 in subsequent cycles), and 75 mg/m² or 100 mg/m² of an HMA (e.g., azacitidine) is administered subcutaneously or intravenously daily for 7 days (e.g., on days 1-7).

In certain embodiments, a total dose of 0.045 mg/kg to about 0.18 mg/kg of an anti-CD123 immunoconjugate (e.g., IMGN632) is administered over the course of a four-week cycle, wherein the total dose is divided into three separate administrations (e.g., on Days 1, 4, and 8 or Days 7, 10, and 14 of the cycle); 100, 200, and/or 400 mg of a BCL-2 inhibitor (e.g., venetoclax) is administered daily (e.g., 100 mg on Day 1, 200 my on Day 2, and 400 mg on Days 3-28 in Cycle 1 and 400 mg daily on Days 1-28 in subsequent cycles), and 75 mg/m² or 100 mg/m² of an HMA (e.g., azacitidine) is administered daily for 7 days (e.g., on days 1-7). In certain embodiments, about 0.015 mg/kg to about 0.06 mg/kg (e.g., 0.015, 0.03, or 0.06 mg/kg) of an anti-CD123 immunoconjugate (e.g., IMGN632) is administered three times in a 28-day cycle (e.g., on days 7, 10, and 14 of the 28-day cycle), 100, 200, and/or 400 mg of a BCL-2 inhibitor (e.g., venetoclax) is administered daily (e.g., 100 mg on Day 1, 200 my on Day 2, and 400 mg on Days 3-28 in Cycle 1 and 400 mg daily on Days 1-28 in subsequent cycles), and 75 mg/m² or 100 mg/m² of an HMA (e.g., azacitidine) is administered daily for 7 days (e.g., on days 1-7). In certain embodiments, about 0.015 mg/kg to about 0.06 mg/kg (e.g., 0.015, 0.03, or 0.06 mg/kg) of an anti-CD123 immunoconjugate (e.g., IMGN632) is administered intravenously three times in a 28-day cycle (e.g., on days 7, 10, and 14 of the 28-day cycle), 100, 200, and/or 400 mg of a BCL-2 inhibitor (e.g., venetoclax) is administered orally daily (e.g., 100 mg on Day 1, 200 my on Day 2, and 400 mg on Days 3-28 in Cycle 1 and 400 mg daily on Days 1-28 in subsequent cycles), and 75 mg/m² or 100 mg/m² of an HMA (e.g., azacitidine) is administered subcutaneously or intravenously daily for 7 days (e.g., on days 1-7).

After administration of an anti-CD123 immunoconjugate, a BCL-2 inhibitor, and an HMA (e.g., azacitidine or decitabine), the anti-CD123 immunoconjugate (e.g., IMGN632) can be administered as a maintenance therapy.

In one instance, the immunoconjugate that binds to CD123 (e.g., IMGN632) and the BCL-2 inhibitor are administered simultaneously. In one instance, the anti-CD123 immunoconjugate (e.g., IMGN632) and the BCL-2 inhibitor are administered in separate pharmaceutical compositions. In one instance, the anti-CD123 immunoconjugate (e.g., IMGN632) and the BCL-2 inhibitor are administered sequentially. In one instance, the BCL-2 inhibitor is administered for a period of time after which both the BCL-2 inhibitor and the anti-CD123 immunoconjugate (e.g., IMGN632) are administered (either simultaneously or sequentially). In such instances an HMA can optionally be administered simultaneously (in the same pharmaceutical composition or a separate pharmaceutical composition) or sequentially with the anti-CD123 immunoconjugate (e.g., IMGN632) or with the BCL-2 inhibitor.

In one instance, the immunoconjugate that binds to CD123 (e.g., IMGN632) and the HMA are administered simultaneously. In one instance, the anti-CD123 immunoconjugate (e.g., IMGN632) and the HMA are administered in the same pharmaceutical composition. In one instance, the anti-CD123 immunoconjugate (e.g., IMGN632) and the HMA are administered in separate pharmaceutical compositions. In one instance, the anti-CD123 immunoconjugate (e.g., IMGN632) and the HMA are administered sequentially. In one instance, the HMA is administered for a period of time after which both the HMA and the anti-CD123 immunoconjugate (e.g., IMGN632) are administered (either simultaneously or sequentially). In such instances a BCL-2 inhibitor can optionally be administered simultaneously or sequentially with the anti-CD123 immunoconjugate (e.g., IMGN632) or the HMA.

VI(C). Assessment and Monitoring

In certain embodiments, the combination of an anti-CD123 immunoconjugate (e.g., IMGN632) and a BCL-2 inhibitor and/or an HMA is useful for inhibiting tumor growth. In certain embodiments, the combination of an anti-CD123 immunoconjugate (e.g., IMGN632) and a BCL-2 inhibitor and/or an HMA is useful for reducing tumor volume. In certain embodiments, the combination of an anti-CD123 immunoconjugate (e.g., IMGN632) and a BCL-2 inhibitor and/or an HMA is useful for increasing survival.

For example, in some embodiments, treatment with a combination of an anti-CD123 immunoconjugate (e.g., IMGN632) and a BCL-2 inhibitor and/or an HMA results in a % T/C value that is less than about 50%, less than about 45%, less than about 40%, less than about 35%, less than about 30%, less than about 25%, less than about 20%, less than about 15%, less than about 10%, or less than about 5%.

In certain embodiments, the combination of an anti-CD123 immunoconjugate (e.g., IMGN632) and a BCL-2 inhibitor and/or an HMA can inhibit tumor growth in an EOL-1 subcutaneous xenograft model. In certain embodiments, the combination of an anti-CD123 immunoconjugate (e.g., IMGN632) and a BCL-2 inhibitor and/or an HMA can inhibit tumor growth in a KG-1 subcutaneous xenograft model.

In certain embodiments, the combination of an anti-CD123 immunoconjugate (e.g., IMGN632) and a BCL-2 inhibitor and/or an HMA can increase survival in an MOLM-1 disseminated xenograft model. In certain embodiments, the combination of an anti-CD123 immunoconjugate (e.g., IMGN632) and a BCL-2 inhibitor and/or an HMA can increase survival in an MV4-11 disseminated xenograft model.

In certain embodiments, the combination of combination of an anti-CD123 immunoconjugate (e.g., IMGN632) and a BCL-2 inhibitor and/or an HMA produces a synergistic effect.

In certain embodiments, administration of combination of an anti-CD123 immunoconjugate (e.g., IMGN632) and a BCL-2 inhibitor and/or an HMA does not produce more toxicity than administration of the BCL-2 inhibitor and/or HMA. In some embodiments, administration of the combination of an anti-CD123 immunoconjugate (e.g., IMGN632) and a BCL-2 inhibitor and/or an HMA does not produce more toxicity than administration of the anti-CD123 immunoconjugate. In some embodiments, administration of combination of an anti-CD123 immunoconjugate (e.g., IMGN632) and a BCL-2 inhibitor and/or an HMA does not produce more toxicity than administration of either the anti-CD123 immunoconjugate or the BCL-2 inhibitor and/or HMA.

VI(D). Additional Therapies

In some embodiments, patients receiving an anti-CD123 immunoconjugate in combination with a BCL-2 inhibitor (e.g., venetoclax) and/or a hypomethylating agent (HMA) (e.g., azacitidine or decitabine) as disclosed herein have received pretreatment with a corticosteroid. Accordingly, in some embodiments, the methods provided herein comprise administering a corticosteroid to a patient prior to administering an anti-CD123 immunoconjugate to the patient. In certain instances, the corticosteroid can be selected from the group consisting of prednisone, prednisolone, methylprednisolone, beclamethasone, betamethasone, dexamethasone, fludrocortisone, hydrocortisone, and triamcinolone. In certain instances the corticosteroid is administered intravenously. In certain instances, the steroid is administered orally.

For example, in some embodiments, patients receiving an anti-CD123 immunoconjugate in combination with a BCL-2 inhibitor (e.g., venetoclax) and/or a hypomethylating agent (HMA) (e.g., azacitidine or decitabine) as disclosed herein have received pretreatment with diphenhydramine. In some embodiments, patients receiving an anti-CD123 immunoconjugate in combination with a BCL-2 inhibitor (e.g., venetoclax) and/or a hypomethylating agent (HMA) (e.g., azacitidine or decitabine) as disclosed herein have received pretreatment with 25-50 mg diphenhydramine. In some embodiments, diphenhydramine is given intravenously. In some embodiments, diphenhydramine is given orally. Accordingly, in some embodiments, the methods provided herein comprise administering diphenhydramine to a patient prior to administering an anti-CD123 immunoconjugate to the patient.

In some embodiments, patients receiving an anti-CD123 immunoconjugate in combination with a BCL-2 inhibitor (e.g., venetoclax) and/or a hypomethylating agent (HMA) (e.g., azacitidine or decitabine) as disclosed herein have received pretreatment with acetaminophen. In some embodiments, patients receiving an anti-CD123 immunoconjugate in combination with a BCL-2 inhibitor (e.g., venetoclax) and/or a hypomethylating agent (HMA) (e.g., azacitidine or decitabine) as disclosed herein have received pretreatment with 325-650 mg acetaminophen. In some embodiments, acetaminophen is given intravenously. In some embodiments, acetaminophen is given orally. Accordingly, in some embodiments, the methods provided herein comprise administering acetaminophen to a patient prior to administering an anti-CD123 immunoconjugate to the patient.

In some embodiments, patients receiving an anti-CD123 immunoconjugate in combination with a BCL-2 inhibitor (e.g., venetoclax) and/or a hypomethylating agent (HMA) (e.g., azacitidine or decitabine) as disclosed herein have received pretreatment with paracetamol. In some embodiments, patients receiving an anti-CD123 immunoconjugate in combination with a BCL-2 inhibitor (e.g., venetoclax) and/or a hypomethylating agent (HMA) (e.g., azacitidine or decitabine) as disclosed herein have received pretreatment with 325-650 mg paracetamol. In some embodiments, paracetamol is given intravenously. In some embodiments, paracetamol is given orally. Accordingly, in some embodiments, the methods provided herein comprise administering paracetamol to a patient prior to administering an anti-CD123 immunoconjugate to the patient.

In some embodiments, patients receiving an anti-CD123 immunoconjugate in combination with a BCL-2 inhibitor (e.g., venetoclax) and/or a hypomethylating agent (HMA) (e.g., azacitidine or decitabine) as disclosed herein have received pretreatment with dexamethasone. In some embodiments, patients receiving anti-CD123 immunoconjugate in combination with a BCL-2 inhibitor (e.g., venetoclax) and/or a hypomethylating agent (HMA) (e.g., azacitidine or decitabine) as disclosed herein have received pretreatment with 8 mg dexamethasone. In some embodiments, dexamethasone is given intravenously. In some embodiments, dexamethasone is given orally. Accordingly, in some embodiments, the methods provided herein comprise administering dexamethasone to a patient prior to administering an anti-CD123 immunoconjugate to the patient.

Embodiments of the present disclosure can be further defined by reference to the following non-limiting examples. It will be apparent to those skilled in the art that many modifications, both to materials and methods, can be practiced without departing from the scope of the present disclosure.

EXAMPLES

It is understood that the examples and embodiments described herein are for illustrative purposes only and that various modifications or changes in light thereof will be suggested to persons skilled in the art and are to be included within the spirit and purview of this application Example 1

In Vitro Studies of the Combination of IMGN632 and Venetoclax in AML Cell Lines

The activity of IMGN632 alone, venetoclax alone, and IMGN632 and venetoclax in combination were investigated in in vitro cytotoxicity assays in four different acute myeloid leukemia (AML) cells lines: EOL-1, KG-1, Molm-13, and MV4-11.

EOL-1, KG-1, Molm-13, and MV4-11 cell lines were obtained at low-passage (under 10 passages), and cell cultures were maintained as recommended by their suppliers. Cells were collected from cell culture in log growth phase, counted by an automated hemocytometer, and distributed evenly to wells in 96-well plates such that each well would contain five thousand live cells per well. Each well contained Fc receptor-blocking, non-mammalian-targeted chKTI monoclonal antibody such that the final well volume (200 μL) would contain chKTI at 100 nM. Dose ranges of IMGN632 alone, venetoclax alone, and IMGN632+venetoclax (along with the respective DMSO controls, in the case of venetoclax) were then prepared in media appropriate to the cell line being assayed.

The dilutions were prepared, and then added, to the cells in 96-well plates on the same day that the cells were plated. Additions of cells and drugs were made such that final well volumes were always 200 μL. Each treatment condition was prepared in triplicate for each assay run. Treated 96-well plates were left undisturbed in dark 37° C. incubators at 90% humidity and 10% $CO_2$ for 4 days (EOL-1, Molm-13; MV4-11) or 5 days (KG-1). At Day 4 or Day 5, 20 μL of WST-8 was added to each well, and the 96-well plate was replaced in the incubator for between 2 (EOL-1; Molm-13) and 7 (MV4-11; KG-1) hours to develop. Upon development, plates were read in a spectrophotometer, with readings taken upon absorbances at 650 nm. Each dose-finding assay run was performed once. Each combination assay run was repeated three (EOL-1; Molm-13; MV4-11) or four (KG-1) times.

Two-step calculations were performed on collected data. The average media-only control absorbances were subtracted from each condition with cells in it, and background-corrected absorbances were indexed to the average background-corrected absorbances of their non-treated control counterparts. These calculated values were plotted in Graph-Pad Prism as the averages and standard deviations of technical replicates across bioreplicate assay runs. The same final calculated values input into GraphPad were further processed for the evaluation of synergy via CalcuSyn. The average "surviving fraction" from each condition was subtracted from 1 to obtain the average "fraction affected" (Fa) from each condition. These Fa values, coupled with drug doses, were input into CalcuSyn (NB: only values "x" for which $0<x<1$ were usable). The input values were used to calculate both Combination Indices (CIs) measuring drug observed versus expected effects, and normalized fractional affect values used in combination treatment isobolograms.

Figure 3A:
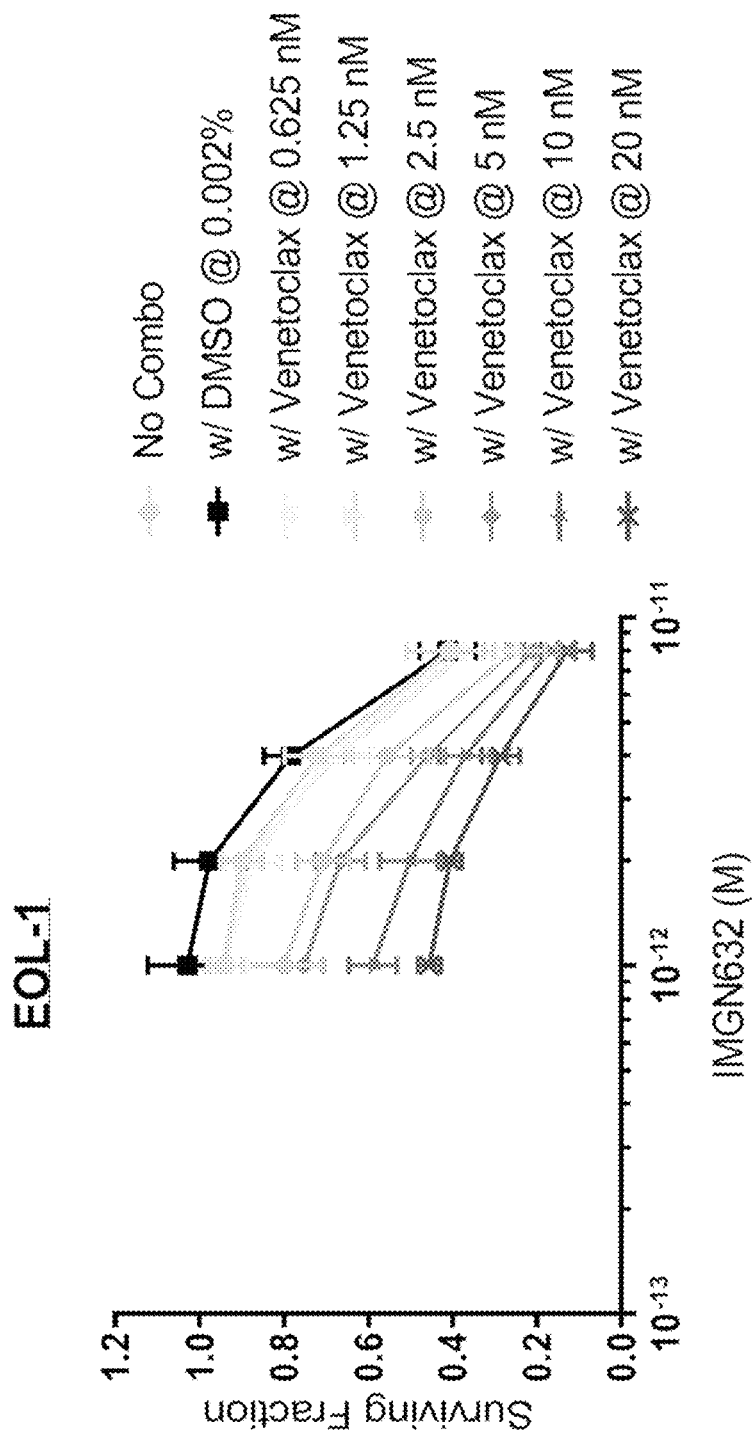
FIG. 3A shows the antitumor activity of IMGN632 and increasing doses of venetoclax (0.625 nM, 1.25 nM, 2.5 nM, 5 nM, 10 nM, 20 nM) against the EOL-1 cell line.
Figure 3B:
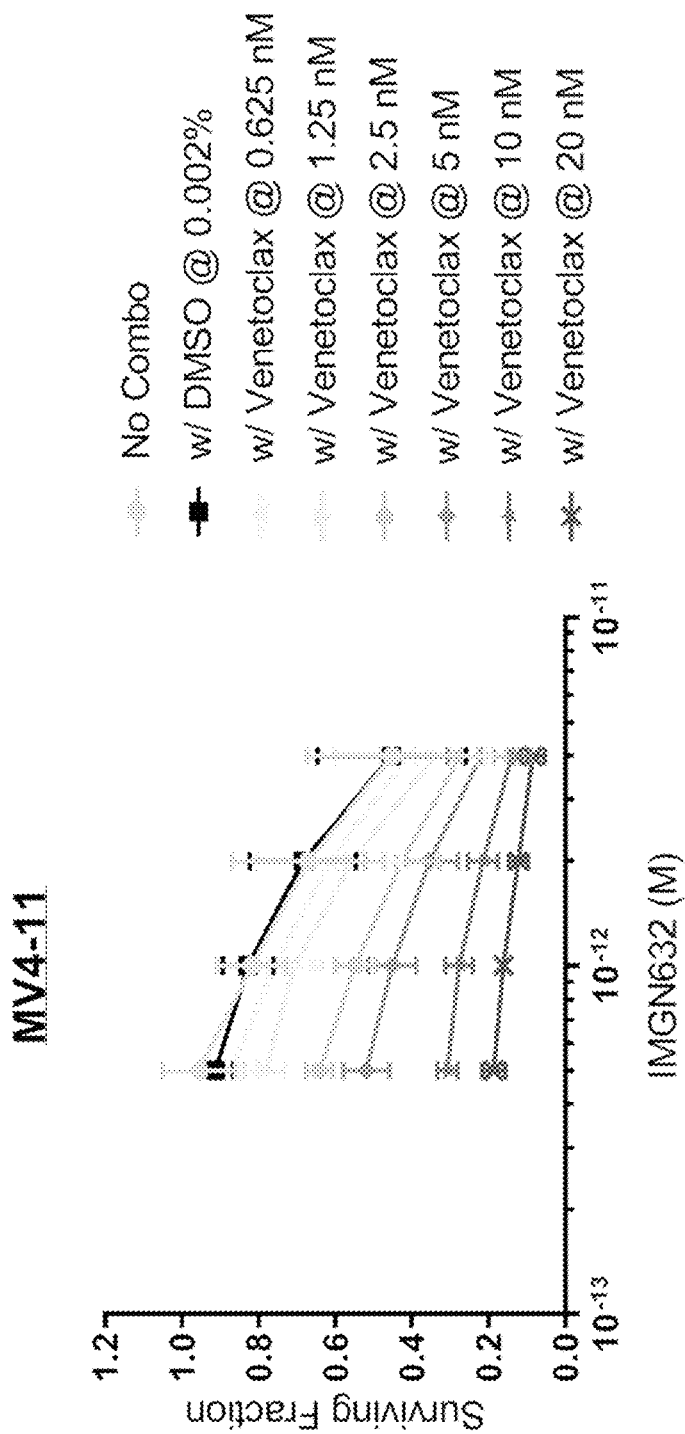
FIG. 3B shows the antitumor activity of IMGN632 and increasing doses of venetoclax (0.625 nM, 1.25 nM, 2.5 nM, 5 nM, 10 nM, 20 nM) in the MV4-11 cell line.
Figure 3C:
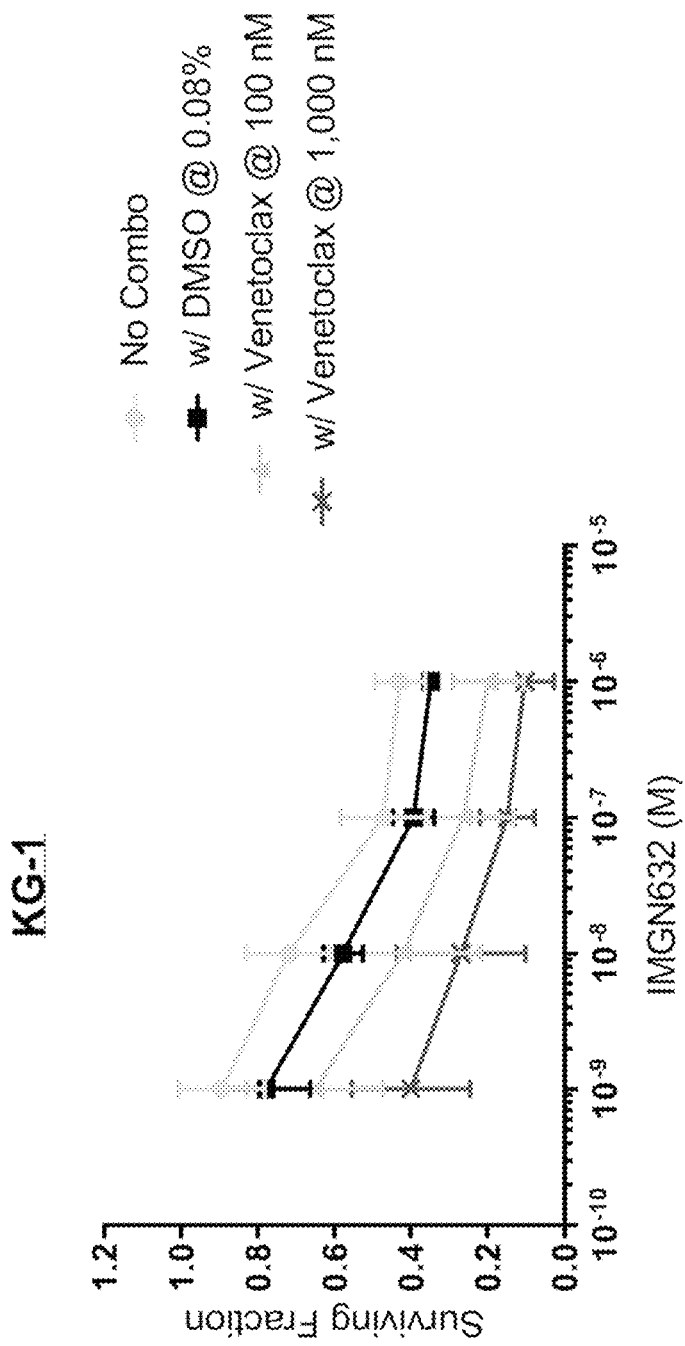
FIG. 3C shows the antitumor activity of IMGN632 and increasing doses of venetoclax (0.625 nM, 1.25 nM, 2.5 nM, 5 nM, 10 nM, 20 nM) in the KG-1 cell line.
Figure 3D:
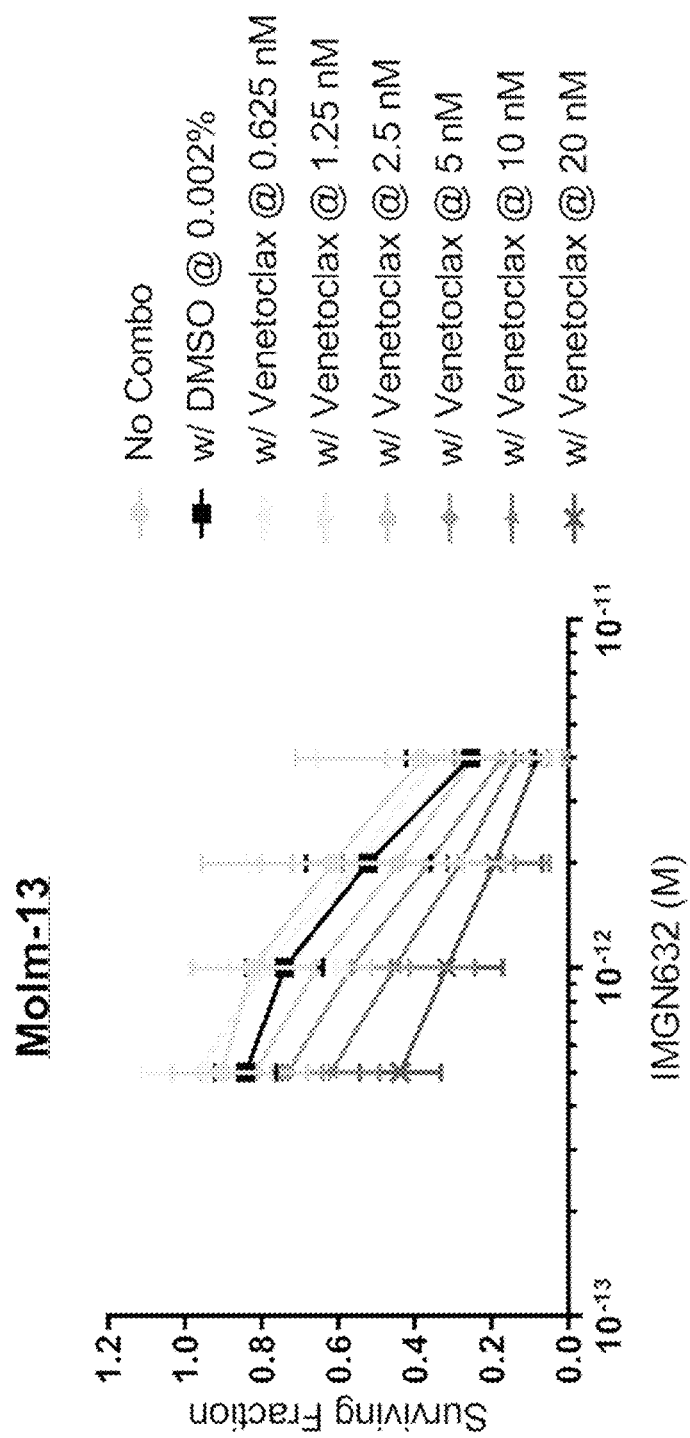
FIG. 3D shows the antitumor activity of IMGN632 and increasing doses of venetoclax (0.625 nM, 1.25 nM, 2.5 nM, 5 nM, 10 nM, 20 nM) in the Molm-13 cell line.
Figure 4A:
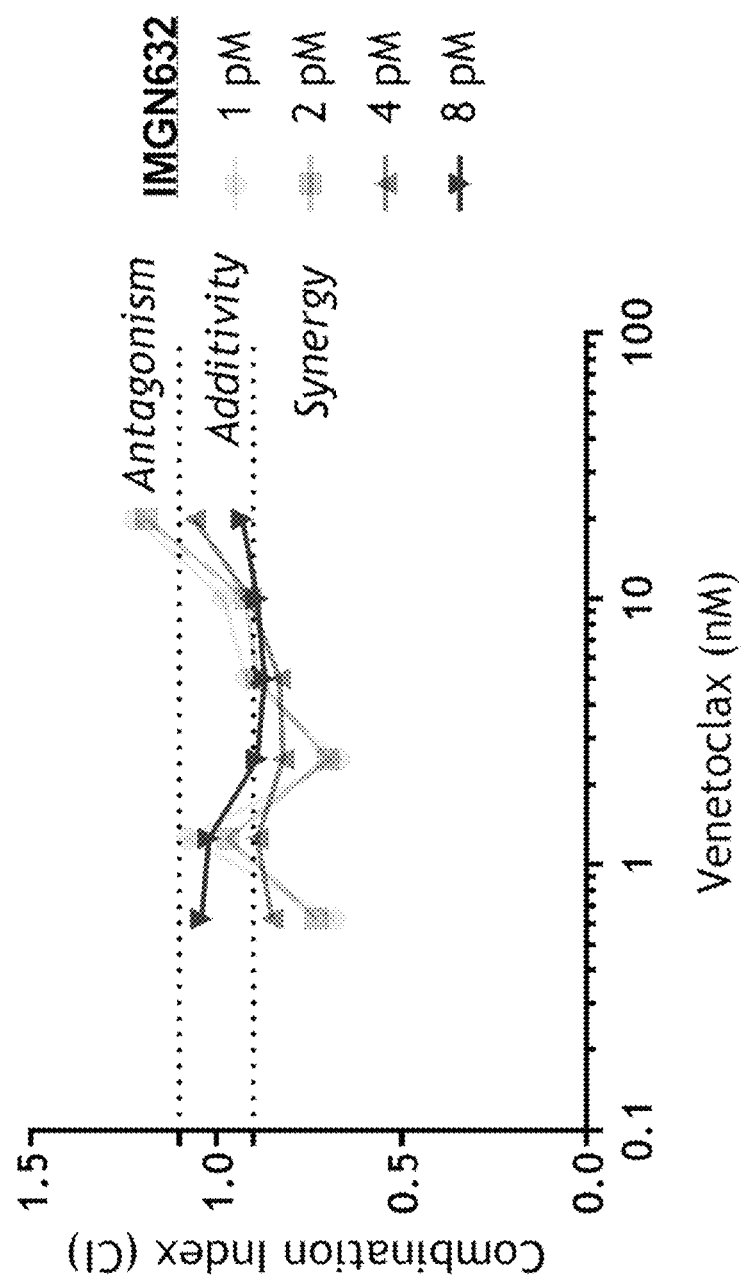
FIG. 4A shows the combination efficacy readouts for the combination of IMGN632 and venetoclax as a function of dose in the EOL-1 cell line.
Figure 4B:
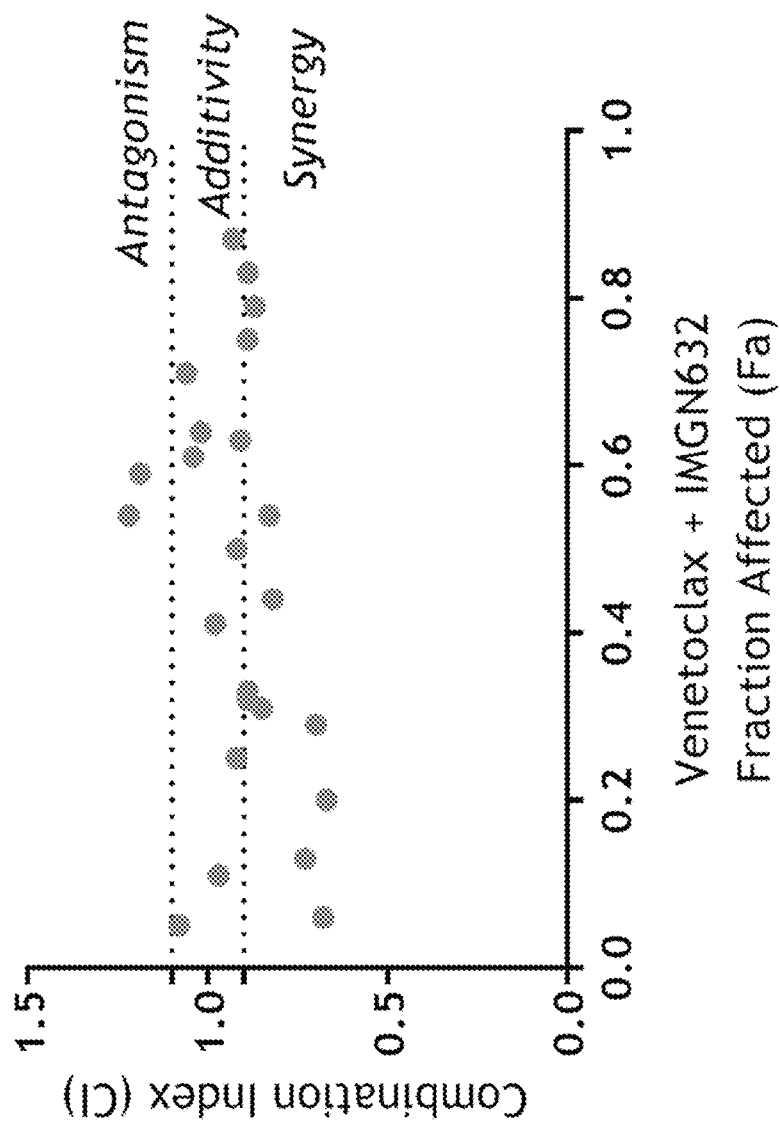
FIG. 4B shows the combination efficacy readouts for the combination of IMGN632 and venetoclax as a function of treatment effect in the EOL-1 cell line.
Figure 4C:
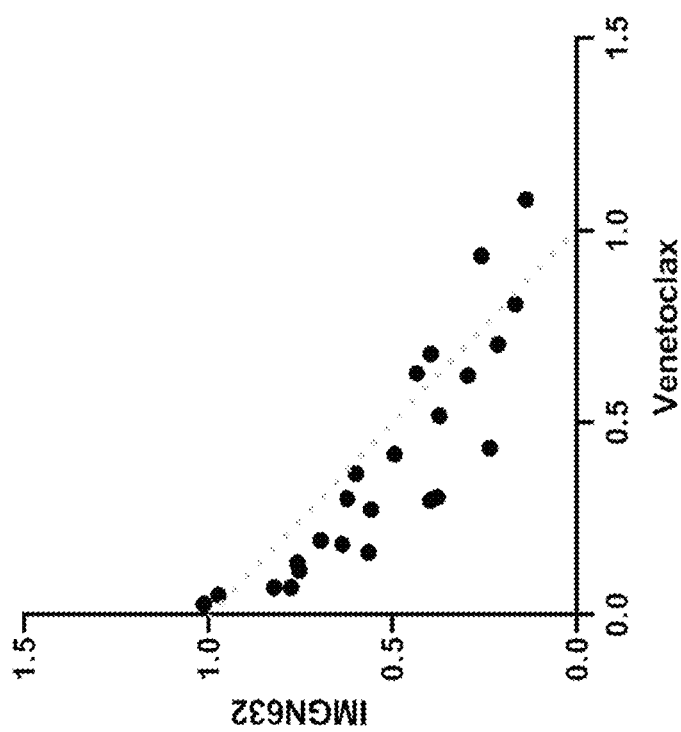
FIG. 4C shows the combination efficacy readouts for the combination of IMGN632 and venetoclax relative to expected dose-effects on a normalized scale in the EOL-1 cell line.
Figure 4D:
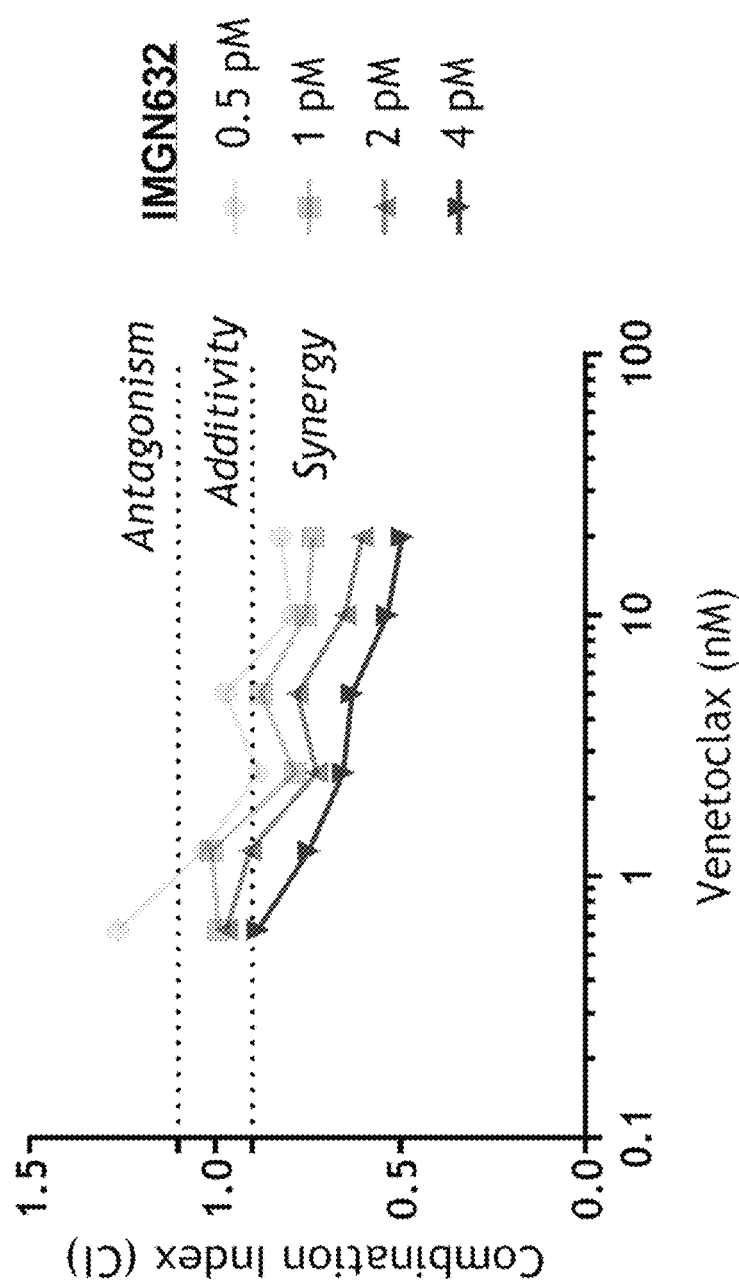
FIG. 4D shows the combination efficacy readouts for the combination of IMGN632 and venetoclax as a function of dose in the MV4-11 cell line.
Figure 4E:
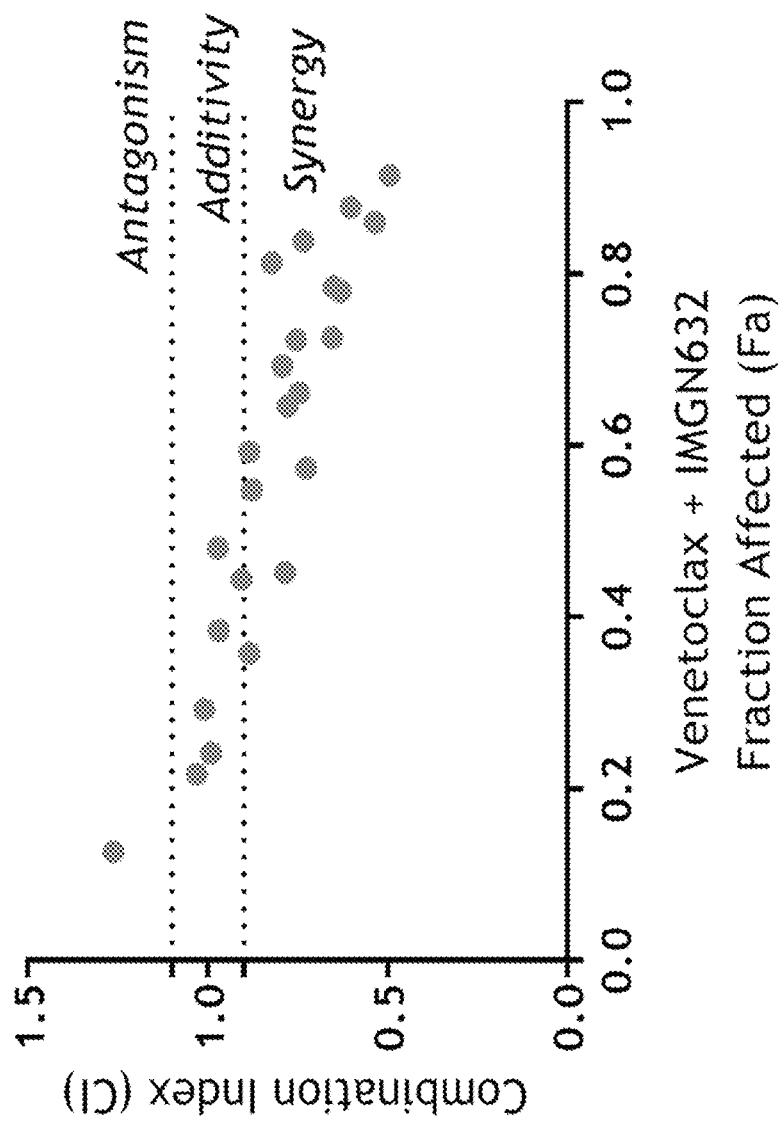
FIG. 4E shows the combination efficacy readouts for the combination of IMGN632 and venetoclax as a function of treatment effect in the MV4-11 cell line.
Figure 4F:
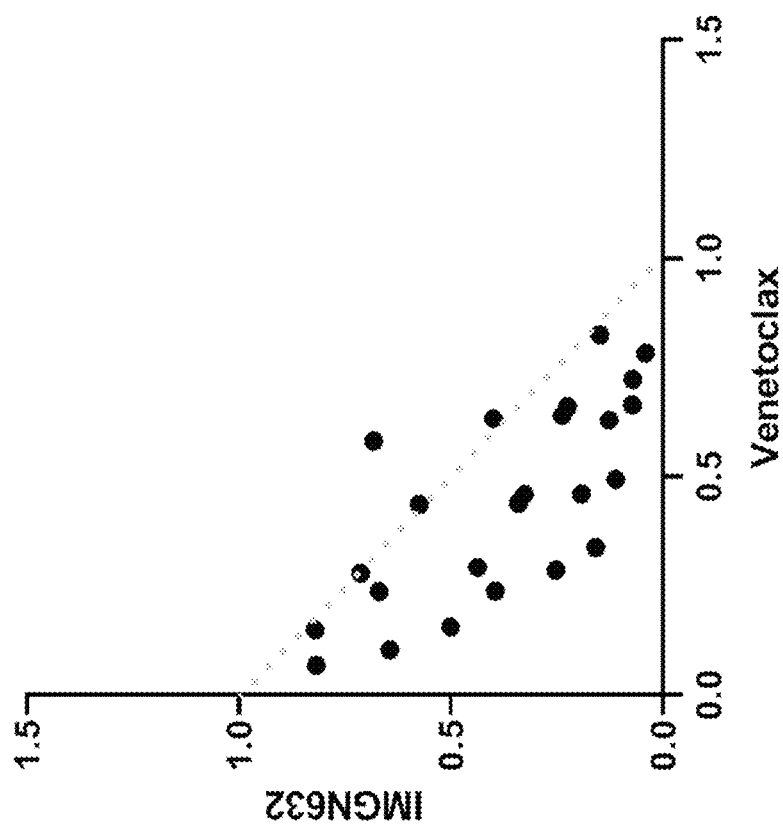
FIG. 4F shows the combination efficacy readouts for the combination of IMGN632 and venetoclax relative to expected dose-effects on a normalized scale in the MV4-11 cell line.
Figure 4G:
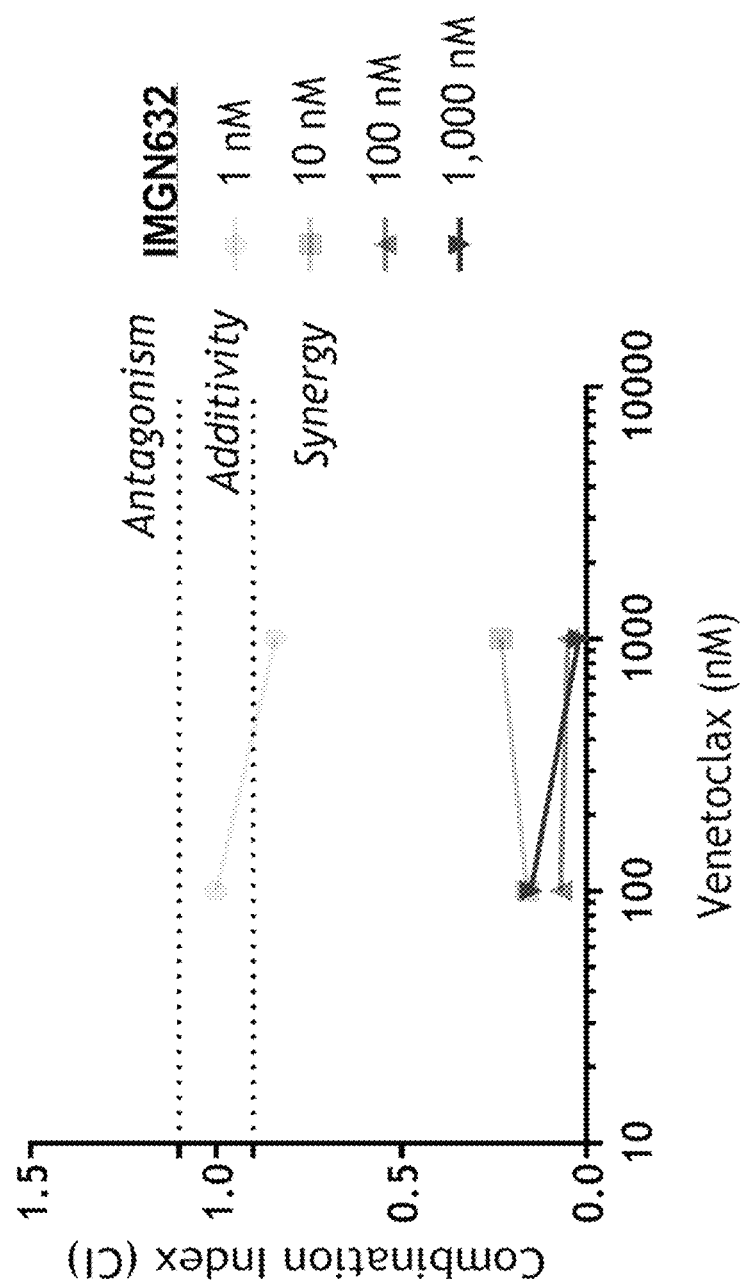
FIG. 4G shows the combination efficacy readouts for the combination of IMGN632 and venetoclax as a function of dose in the KG-1 cell line.
Figure 4H:
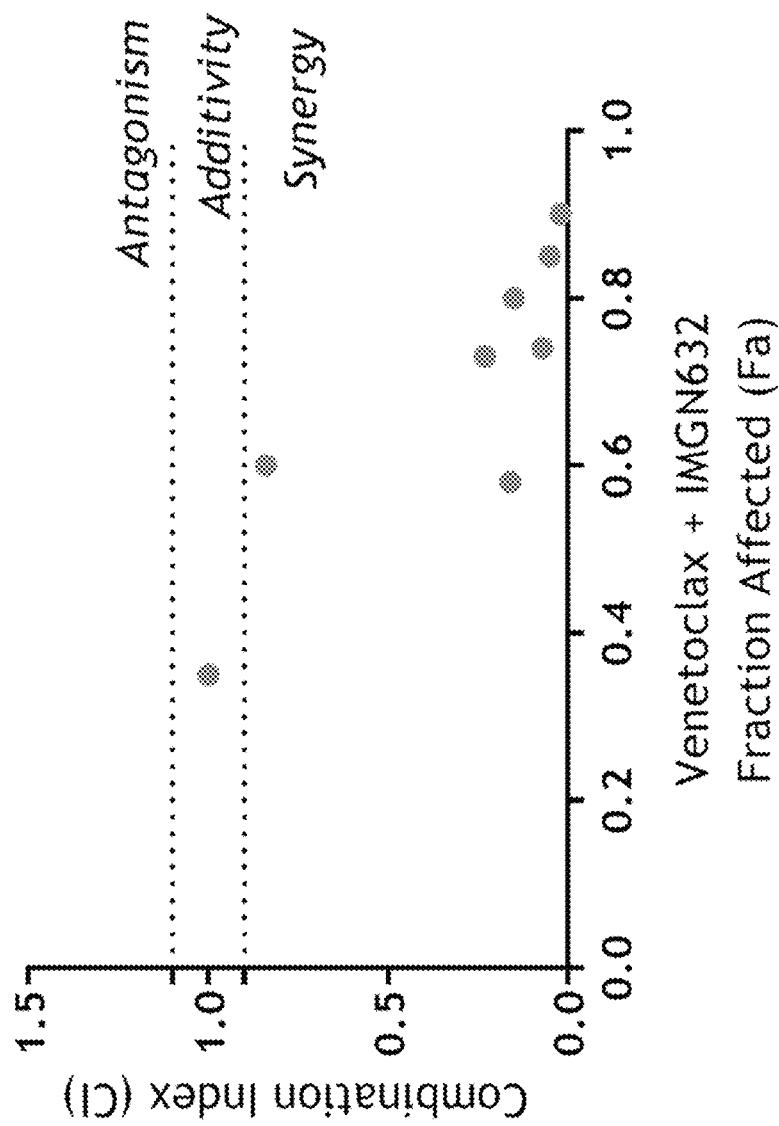
FIG. 4H shows the combination efficacy readouts for the combination of IMGN632 and venetoclax as a function of treatment effect in the KG-1 cell line.
Figure 4I:
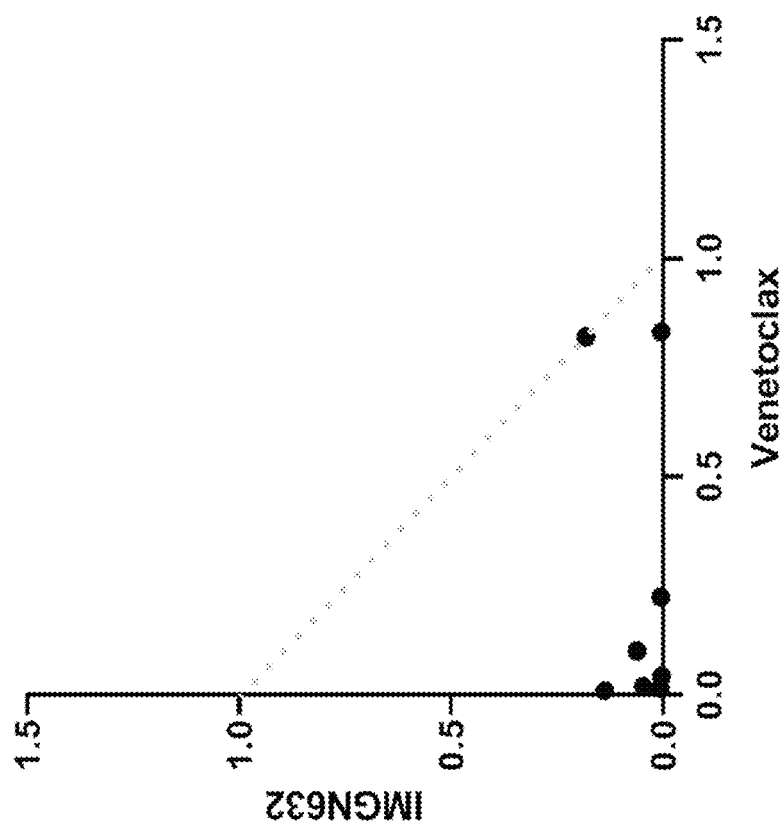
FIG. 4I shows the combination efficacy readouts for the combination of IMGN632 and venetoclax relative to expected dose-effects on a normalized scale in the KG-1 cell line.
Figure 4J:
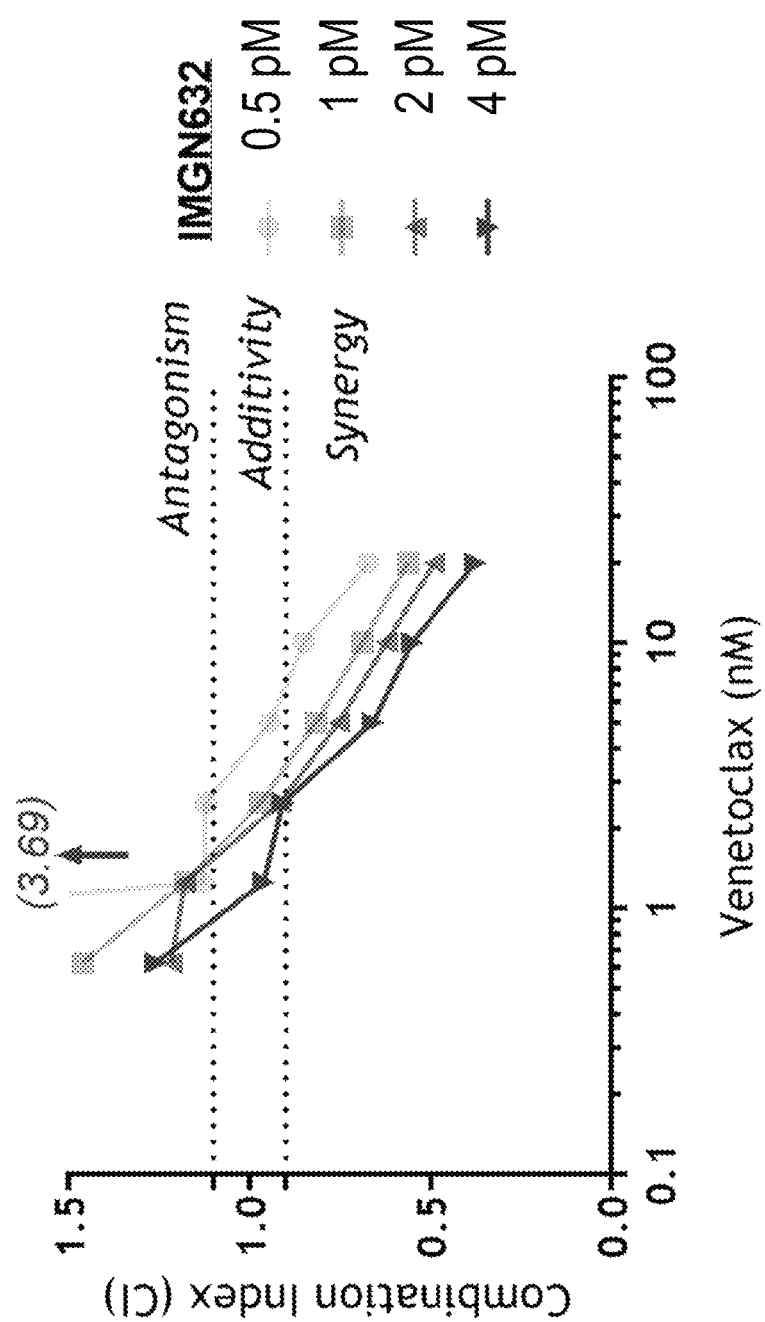
FIG. 4J shows the combination efficacy readouts for the combination of IMGN632 and venetoclax as a function of dose in the Molm-13 cell line.
Figure 4K:
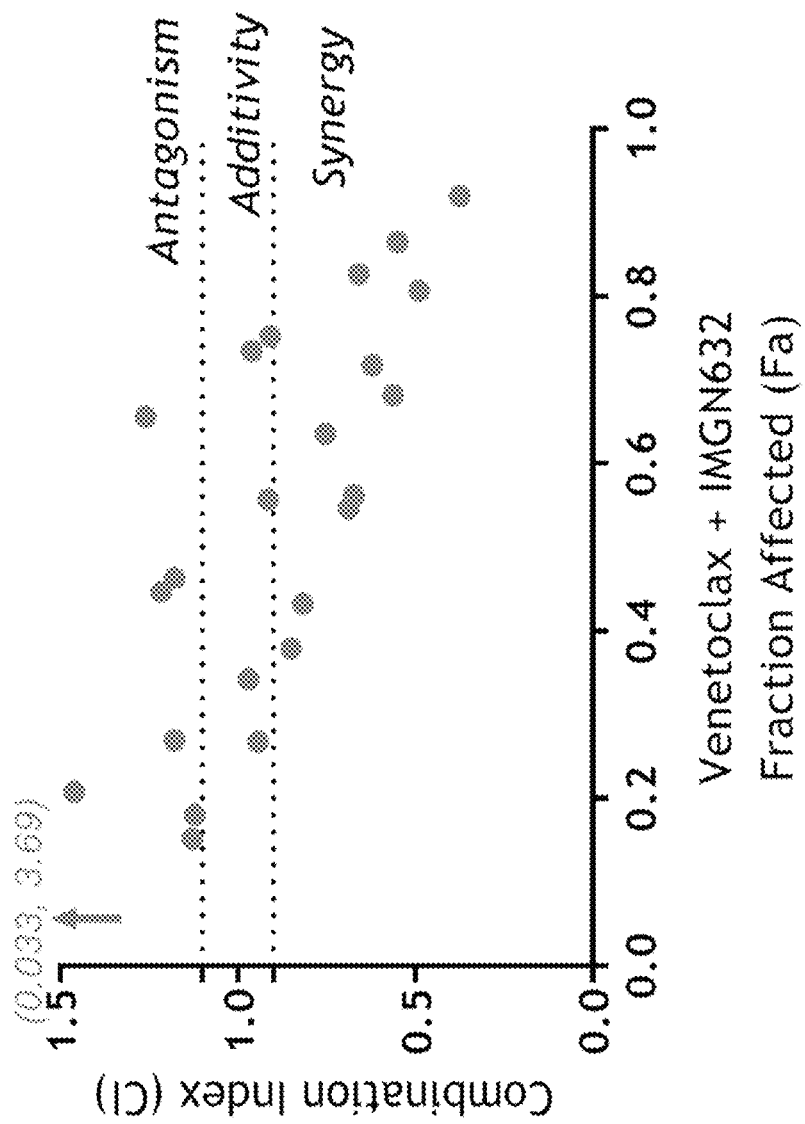
FIG. 4K shows the combination efficacy readouts for the combination of IMGN632 and venetoclax as a function of treatment effect in the Molm-13 cell line.
Figure 4L:
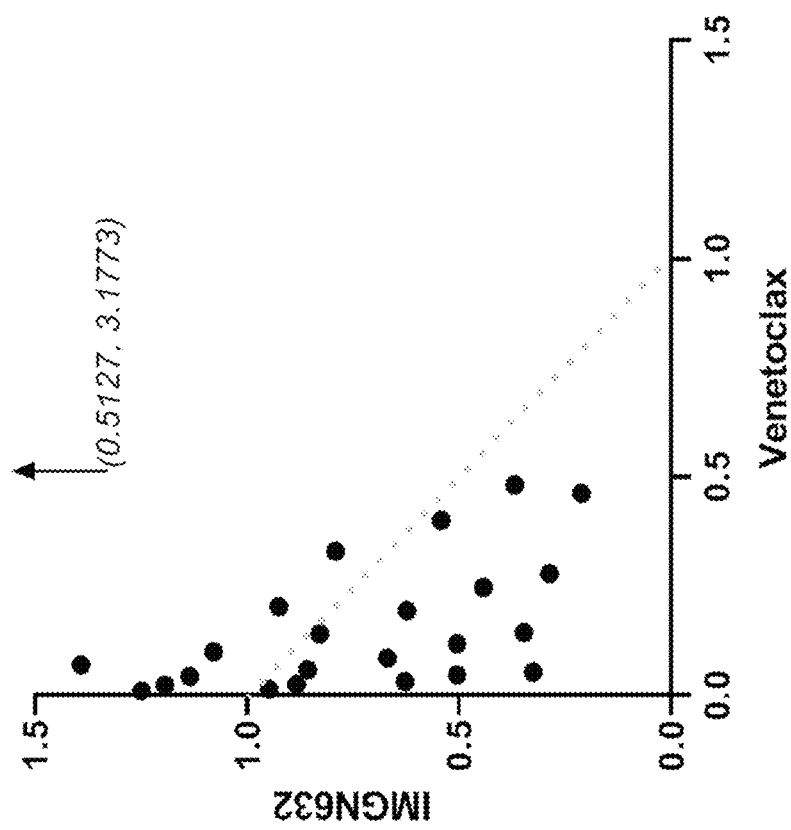
FIG. 4L shows the combination efficacy readouts for the combination of IMGN632 and venetoclax relative to expected dose-effects on a normalized scale in the Molm-13 cell line.

The results of the in vitro cytotoxicity assays of IMGN632 and venetoclax alone are shown in FIGS. 2A-2D. Broad dose ranges of IMGN632 (FIG. 2A) and venetoclax (FIG. 2B) doses were tested for potency against three AML cell lines (EOL-1, MV4-11, KG-1). Doses near the inflection points of these sensitivity curves were selected for use in IMGN632 and venetoclax combination assays. Narrower ranges of IMGN632 (FIG. 2C) and venetoclax (FIG. 2D) doses were run as single-agent controls for the combination studies, and these doses represent a dynamic range of drug potencies. FIGS. 3A-3D show the results of combinations of IMGN632 and venetoclax assessed in four AML cell lines: EOL-1 (FIG. 3A), MV4-11 (FIG. 3B), KG-1 (FIG. 3C), and Molm-13 (FIG. 3D). In each of the four AML cell lines assessed, IMGN632 and venetoclax kill more cells in combination than IMGN632 alone, in a dose-dependent fashion. FIGS. 4A-4L show combination efficacy readouts for the combination of IMGN632 and venetoclax comparing the observed combination results of FIGS. 3A-3D to the expected combination results based on the single-agent treatment results of FIGS. 2C and 2D. Combination Index values and normalized relative effect values were generated for each IMGN632 and venetoclax dose pairing. The results were plotted so as to show: combination efficacy as a function of drug doses (FIGS. 4A, 4D, 4G, and 4J), combination efficacy as a function of treatment effect (FIGS. 4B, 4E, 4H, and 4K), and combination efficacy relative to expected dose-effects, on normalized scales (FIGS. 4C, 4F, 4I, and 4L). Each row represents results from a single cell line: EOL-1 (FIG. 4A-4C), MV4-11 (FIGS. 4D-4F), KG-1 (FIGS. 4G-4I), or Molm-13 (FIGS. 4J-4L).

The results from the in vitro cytotoxicity assays of AML cell lines treated with IMGN632 and venetoclax indicate an additive-to-synergistic combinatory cytotoxic effect of the combination.

Example 2

Materials and Methods Used for Subcutaneous and Disseminated Xenograft Models

For all subcutaneous xenograft models, mice were weighed twice a week and were monitored for clinical signs throughout the duration of the study. Animals were euthanized when hind leg paralysis was present, body weight decreased by >20% of pre-treatment weight, tumor ulceration occurred, or when any signs of distress were visible.

Tumor volumes in subcutaneous xenograft models were measured one to two times weekly in three dimensions using a caliper. The tumor volume was expressed in $mm^3$ using the formula V=Length×Width×Height×½ (Tomayko and Reynolds, *Cancer Chemother. Pharmacol.* 24: 148-54 (1989)). Activity was assessed as described in Bissery et al., *Cancer Res.* 51: 4845-52 (1991).

Tumor Growth Inhibition (T/C Value) was assessed in subcutaneous xenograft models using the following formula: T/C (%)=(Median tumor volume of the treated/Median tumor volume of the control)×100%. Tumor volume was determined simultaneously for the treated (T) and the vehicle control (C) groups when tumor volume of the vehicle control reached a predetermined size (Bissery et al., *Cancer Res.* 51: 4845-52 (1991). The daily median tumor volume of each treated group was determined, including tumor-free mice (0 $mm^3$). According to National Cancer Institute (NCI) standards, a T/C≤42% is the minimum level of anti-tumor activity. A T/C<10% is considered a high anti-tumor activity level.

For all disseminated xenograft models, mice were weighed twice a week and were monitored for clinical signs throughout the duration of the study. The measured endpoint was survival. Animals were euthanized when hind leg paralysis was present, body weight decreased by >20% of pre-treatment weight, a visible tumor appeared, or any signs of distress were visible. Spontaneous deaths were recorded when they were observed.

Tumor Growth Delay in disseminated xenograft models was calculated as T−C, where T is the median survival time (in days) of a treated group, and C is the median survival time (in days) of the vehicle control group. The Percent Increased Life Span (% ILS) for disseminated models was calculated using the following formula: % ILS=(T−C)/C× 100%. Anti-tumor activity was evaluated as per NCI standards for disseminated models: ILS<25% is inactive, ILS≥25% is minimum active, ILS>40% is active, and ILS≥50% is highly active.

Example 3

In Vivo Efficacy of the Combination of IMGN632 (Single Dose) and Venetoclax (QD×28) in EOL-1 Subcutaneous Model To test the efficacy of IMGN632, venetoclax, or the combination of these two agents for the ability to decrease tumor burden in vivo, a subcutaneous tumor model was used as described in the protocol below.

Female athymic nude mice were each inoculated with 1×10$^7$ EOL-1 cells (a human AML cell line) in 100 µl of 50% Matrigel: 50% serum free medium (v/v) subcutaneously in the right flank. On day 9, which is 24 hours prior to conjugate administration for groups receiving conjugate treatment (either alone or in combination with venetoclax), all the mice in these treatment groups were injected intraperitoneally with 150 mg/kg of non-targeted chKTI antibody to block Fc receptors on the EOL-1 AML cells, preventing non-specific up-take of conjugate. On day 9 post-EOL-1 inoculation, mice were randomized into the study groups based on tumor volume.

On day 10 post-EOL-1 inoculation, the mice received a single intravenous injection, in the lateral tail vein, of either vehicle, or 1 µg/kg (by DGN549; 0.080 mg/kg by huCD123Ab) IMGN632, or 0.5 µg/kg (by DGN549; 0.040 mg/kg by huCD123Ab) IMGN632. Venetoclax administration was also initiated on day 10, and the mice receiving venetoclax were given a single oral dose of 100 mg/kg venetoclax on each day of days 10 through 37, inclusive, post-cell implantation, for a total of 28 consecutive daily administrations. In the combination groups, the mice received administrations of both IMGN632 and venetoclax as outlined above.

Figure 5:
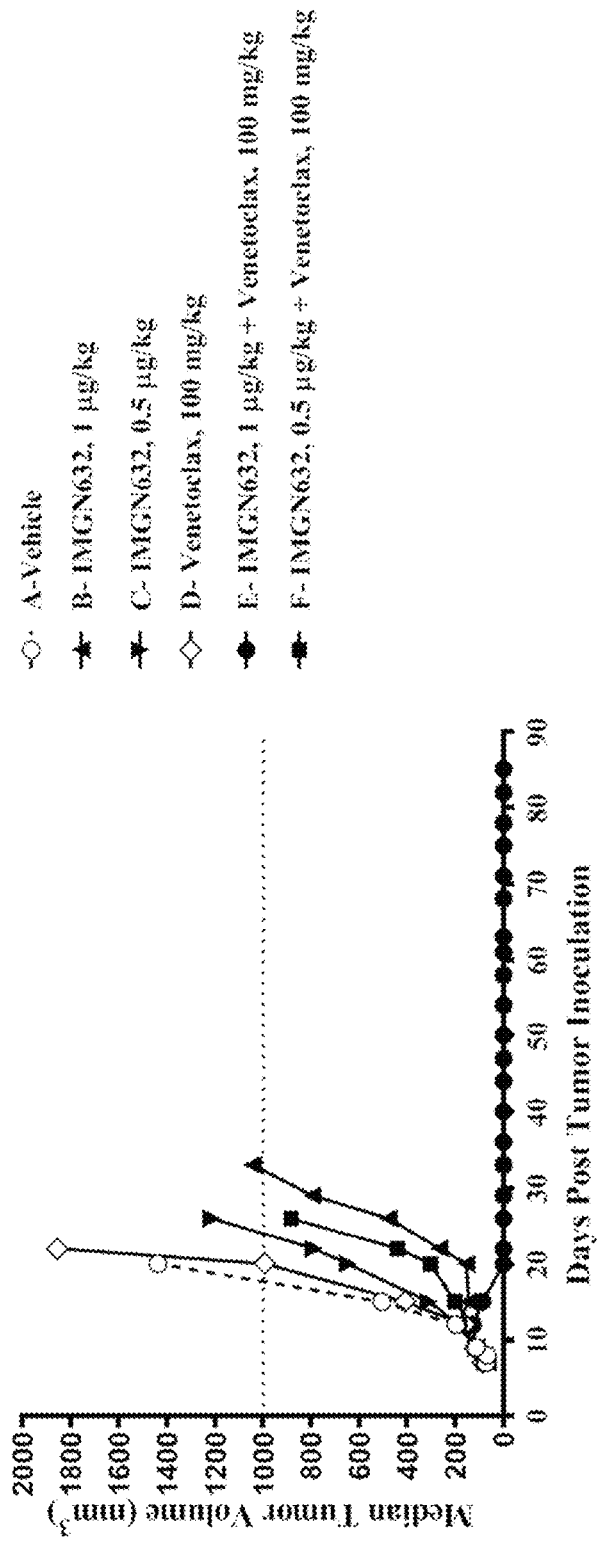
FIG. 5 shows the in vivo efficacy of a single dose of IMGN632 alone (1 μg/kg or 0.5 μg/kg), venetoclax alone (QD×28; 100 mg/kg), and the combination of IMGN632 (1 μg/kg or 0.5 μg/kg) and venetoclax (QD×28; 100 mg/kg) by plotting the median tumor volume (mm$^3$) as a function of days post inoculation of the EOL-1 cell line.

The results are reported in Table 4 (below) and in FIG. 5.

A single dose of 1 µg/kg or 0.5 µg/kg of IMGN632 resulted in a T/C value of 10.7% (active) or 45.0% (inactive), respectively, and resulted in 2/6 or in 0/6 long-term complete regressions (tumor free survivors, TFS), respectively, at the end of the study (day 85).

A regimen of 100 mg/kg of venetoclax, once-a-day (QD) for 28 days (×28), was inactive, resulting in a T/C of 69.1% and in 1/6 TFS on day 85.

The combination of a single dose of 1 µg/kg of IMGN632 and the QD×28 regimen of venetoclax was highly active and resulted in a T/C of 0% and 4/6 TFS on day 85, which is 2 TFS more than were obtained with IMGN632 single agent treatment, demonstrating the additional benefit of the combination treatment. The combination of a single dose of 0.5 µg/kg of IMGN632 and the QD×28 regimen of venetoclax was active, resulting in a T/C of 21.1% and 1/6 TFS on day 85, which is a lower % T/C value than was generated by either 0.5 ug/kg IMGN632 alone (45%) or venetoclax alone (69.1%), indicating the combination was able to slow tumor growth more than either corresponding monotherapy.

TABLE 4

Results from Combination of IMGN632 and Venetoclax in EOL-1 Subcutaneous Model

| Group/Treatment | Treatment Days | % T/C (Day 20) | PR | CR | Tumor Free Survivors (Day 85) | Result |
|---|---|---|---|---|---|---|
| A) Vehicle | — | — | 2/6 | 2/6 | 2/6 | — |
| B) IMGN632, single dose, 1 µg/kg by DGN549 | Day 10 | 10.7 | 2/6 | 2/6 | 2/6 | Active |
| C) IMGN632, single dose, 0.5 µg/kg by DGN549 | Day 10 | 45.0 | 0/6 | 0/6 | 0/6 | Inactive |
| D) Venetoclax, daily x28, 100 mg/kg | Days 10 to 37 (28 days total) | 69.1 | 1/6 | 1/6 | 0/6 | Inactive |
| E) IMGN632 (single dose, 1 µg/kg by DGN549) and Venetoclax (daily x28, 100 mg/kg) | IMGN632: Day 10, and Venetoclax: Days 10 to 37 (28 days total) | 0 | 4/6 | 4/6 | 4/6 | Highly Active |
| F) IMGN632 (single dose, 1 µg/kg by DGN549) and Venetoclax (daily x28, 100 mg/kg) | IMGN632: Day 10, and Venetoclax: Days 10 to 37 (28 days total) | 21.1 | 1/6 | 1/6 | 1/6 | Active |

Example 4

In Vivo Efficacy of the Combination of IMGN632 (QW×3) and Venetoclax (QD×28) in KG-1 Subcutaneous Model To test the efficacy of IMGN632, venetoclax, or the combination of these two agents for the ability to decrease tumor burden in vivo, a subcutaneous tumor model was used as described in the protocol below.

Female C. B17 SCID mice were each inoculated with 1×10$^7$ KG-1 cells (a relatively IMGN632-resistant human AML cell line) in 100 µl of 50% Matrigel: 50% serum free medium (v/v) subcutaneously in the right flank. On days 17, 24, and 31, which are 24 hours prior to each conjugate administration day for groups receiving conjugate treatment (either alone or in combination with venetoclax), all the mice in these treatment groups were injected intraperitoneally with 150 mg/kg of non-targeted chKTI antibody to block Fc receptors on the KG-1 AML cells, preventing non-specific up-take of conjugate. On day 17 post-KG-1 inoculation, mice were randomized into the study groups based on tumor volume.

On days 18, 25, and 32 post-KG-1 inoculation, the mice received a single intravenous injection, in the lateral tail vein, of either vehicle, 3 µg/kg (by DGN549; 0.24 mg/kg by huCD123 Ab) IMGN632, or 10 µg/kg (by DGN549; 0.80 mg/kg by huCD123 Ab) IMGN632. Venetoclax administration was also initiated on day 18, and the mice receiving venetoclax were given a single oral dose of 100 mg/kg venetoclax on each of 28 consecutive days (days 18 through 45). In the combination group, the mice received administrations of both IMGN632 and venetoclax as outlined above.

Figure 6:
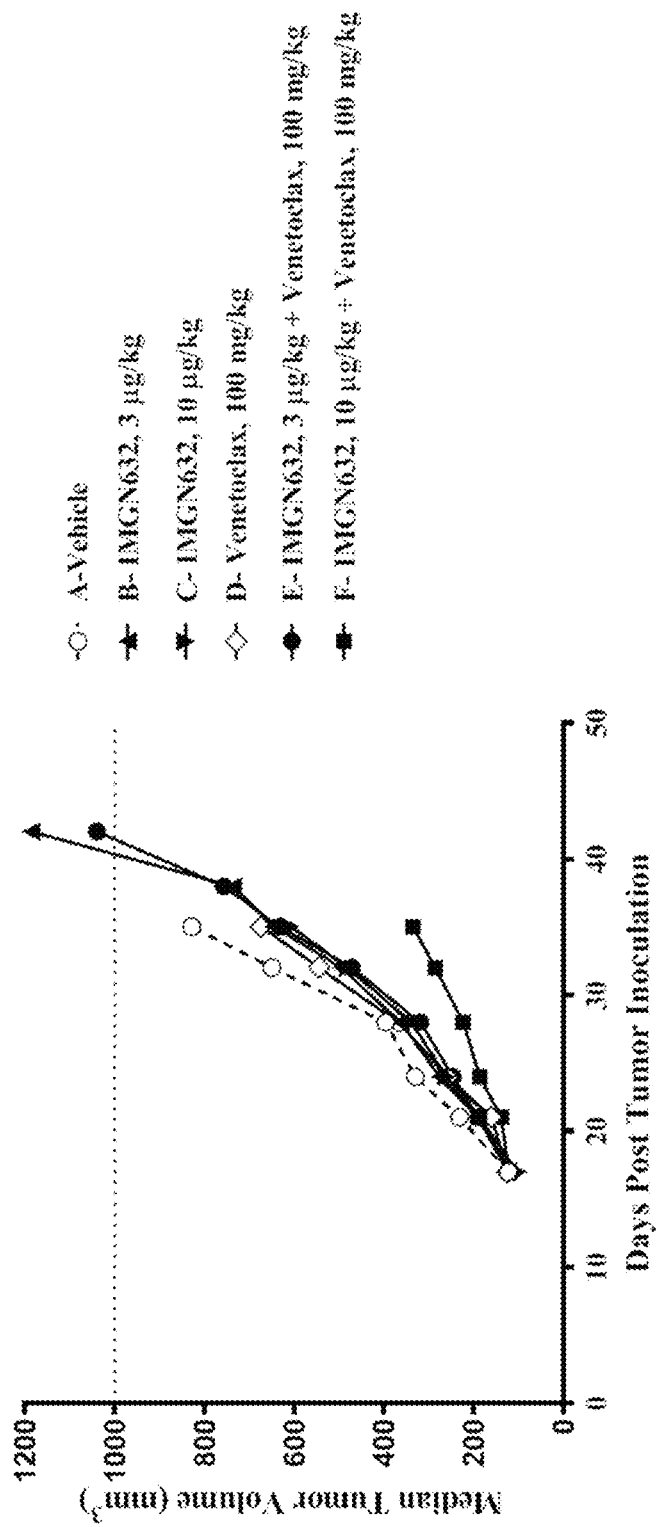
FIG. 6 shows the in vivo efficacy of IMGN632 alone (QW×3; 3 μg/kg or 10 μg/kg), venetoclax alone (QD×28; 100 mg/kg), and the combination of IMGN632 (QW×3; 3 μg/kg or 10 μg/kg) and venetoclax (QD×28; 100 mg/kg) by plotting the median tumor volume (mm$^3$) as a function of days post inoculation of the KG-1 cell line.

The results are reported in Table 5 (below) and in FIG. 6.

A QW×3 regimen of 3 µg/kg of IMGN632 was inactive in this study, resulting in a T/C value of 78% and 0/6 long-term complete regressions (tumor free survivors, TFS) at the end of the study (day 56). Similarly, a QW×3 regimen of 10 µg/kg of IMGN632 was inactive in this study, resulting in a T/C value of 73% and 0/6 TFS. A regimen of 100 mg/kg of venetoclax, once-a-day (QD) for 28 days (×28), was also inactive, resulting in a T/C of 82% and 0/6 TFS.

The combination of 3 µg/kg of IMGN632, QW×3, and the QD×28 regimen of venetoclax was also inactive, resulting in a T/C of 76% and 0/6 TFS. However, he combination of 10 µg/kg of IMGN632, QW×3, and the QD×28 regimen of venetoclax was active, resulting in a T/C of 40% and 0/6 TFS. These results demonstrating that combination treatment can be effective even where either agent alone is inactive.

TABLE 5

Results from Combination of IMGN632 and Venetoclax in KG-1 Subcutaneous Model

| Group/Treatment | Treatment Days | % T/C (Day 35) | PR | CR | Tumor Free Survivors (Day 56) | Result |
| --- | --- | --- | --- | --- | --- | --- |
| A) Vehicle | — | — | 0/6 | 0/6 | 0/6 | — |
| B) IMGN632, QW×3, 3 µg/kg by DGN549 | Days 18, 25, 32 | 78 | 0/6 | 0/6 | 0/6 | Inactive |
| C) IMGN632, QW×3, 10 µg/kg by DGN549 | Days 18, 25, 32 | 73 | 0/6 | 0/6 | 0/6 | Inactive |
| D) Venetoclax, daily x28, 100 mg/kg | Days 18 through 45 (28 days total) | 82 | 0/6 | 0/6 | 0/6 | Inactive |
| E) IMGN632 (QW×3, 3 µg/kg by DGN549) and Venetoclax (daily x28, 100 mg/kg) | IMGN632: Days 18, 25, 32; and Venetoclax: Days 18 through 45 (28 days total) | 76 | 0/6 | 0/6 | 0/6 | Inactive |
| F) IMGN632 (QW×3, 10 µg/kg by DGN549) and Venetoclax (daily x28, 100 mg/kg) | IMGN632: Days 18, 25, 32; and Venetoclax: Days 18 through 45 (28 days total) | 40 | 0/6 | 0/6 | 0/6 | Active |

In conclusion, the combination of IMGN632 and venetoclax demonstrated synergistic cytotoxicity in vitro and greater tumor growth inhibition and prolonged survival in vivo.

Example 5

In Vivo Efficacy of the Combination of IMGN632 (QW×3) and Azacitidine (QD×5) in Molm-13 Disseminated Model To test the efficacy of IMGN632, azacitidine, or the combination of these two agents for the ability to decrease tumor burden in vivo, a disseminated tumor model was used as described in the protocol below.

Female NOD SCID mice were pre-treated with 150 mg/kg cyclophosphamide to partially ablate bone marrow to improve the engraftment of Molm-13 cells. The cyclophosphamide (Sigma, C0768, Lot #MKBX1822V) was dissolved in 0.9% NaCl and was administered intraperitoneally to the mice on day −2 prior to Molm-13 cell inoculation on day 0.

Following cyclophosphamide treatment as described above, the mice were each injected intravenously in the lateral tail vein with $2\times10^5$ Molm-13 cells (a human AML cell line) in 100 µl of serum-free medium on day 0 in the study. On day 6 post-Molm-13 inoculation, mice were randomized into study groups based on body weight. At 24 hours prior to each conjugate administration, for all groups receiving conjugate treatment (either alone or in combination with azacitidine), the mice were injected intraperitoneally with 150 mg/kg of non-targeted chKTI antibody to block Fc receptors on the Molm-13 AML cells, preventing non-specific up-take of conjugate.

Mice received IMGN632 at a dose of 0.3 µg/kg by DGN549 (0.024 mg/kg by huCD123 Ab) once a week (QW) for three doses (×3) according to three different IMGN632 dosing schedules, either alone or in combination with azacitidine. These three different IMGN632 dosing schedules were: i) days 7, 14, and 21 (referred to as "Day 7" for IMGN632); ii) days 11, 18, and 25 (referred to as "Day 11" for IMGN632); and iii) days 14, 21, and 28 (referred to as "Day 14" for IMGN632), where the noted start day of IMGN632 treatment was moved progressively away from day 0 (the day of Molm-13 inoculation) in the study time line.

Azacitidine was given once a day (QD) at a dose of 3.5 mg/kg for 5 consecutive days (×5; days 7, 8, 9, 10, and 11; the "Day 7" schedule), either alone or in combination with IMGN632.

Mice were treated with a combination regimen of IMGN632 (QW×3) and 3.5 mg/kg azacitidine (QD×5) according to one of three different dosing schedules for combining the two drugs: i) the Day 7 schedule for IMGN632 and the Day 7 schedule for azacitidine (Group F), ii) the Day 11 schedule for IMGN632 and the Day 7 schedule for azacitidine (Group G), and iii) the Day 14 schedule for IMGN632 and the Day 7 schedule for azacitidine (Group H).

Figure 7:
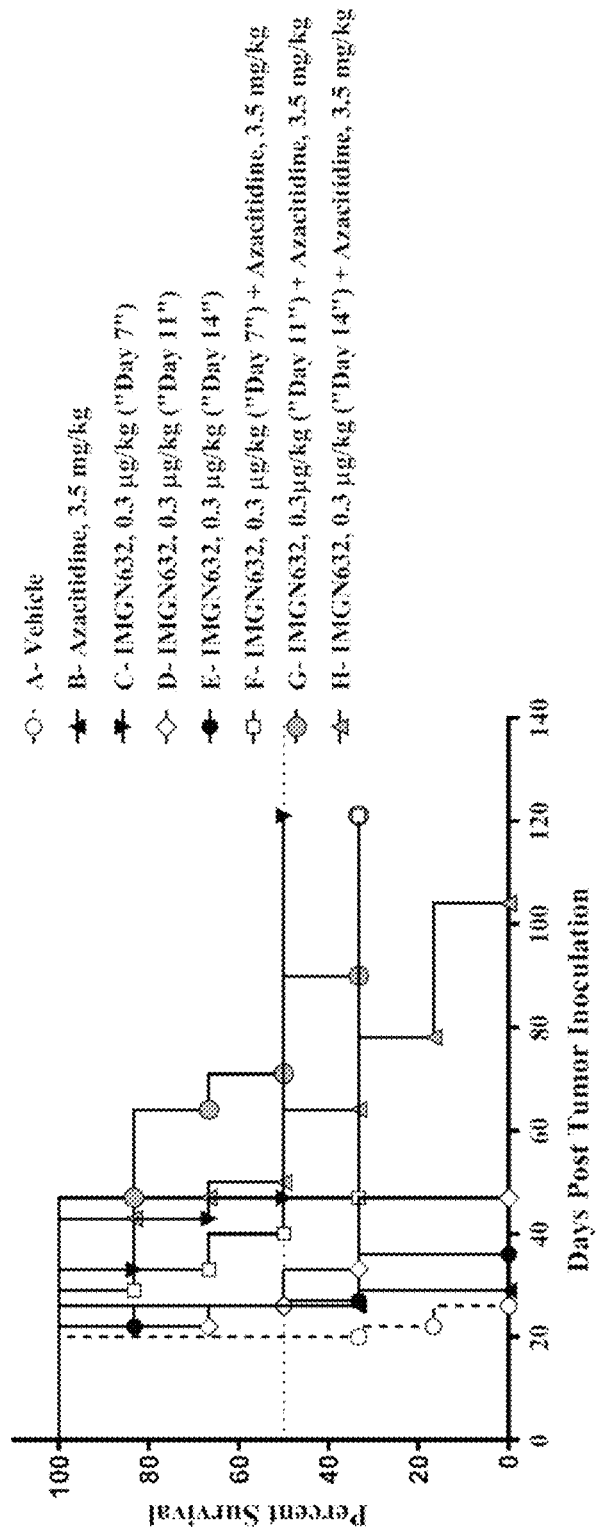
FIG. 7 shows the survival of mice as a function of time post Molm-3 tumor cell inoculation. Mice received IMGN632 alone (QW×3; 0.3 μg/kg) according to three different dosing schedules, azacitidine alone (QD×5; 3.5 mg/kg), or a combination of IMGN632 (QW×3; 0.3 μg/kg) and azacitidine (QD×5; 3.5 mg/kg).

The results are represented in Table 6 (below) and in FIG. 7.

Azacitidine single-agent (Group B), administered at 3.5 mg/kg, QD×5, according to the Day 7 schedule, was minimally active in this study, resulting in a tumor growth delay (T–C value) of 6 days, and a 30% ILS (Increased Life Span) compared to vehicle treatment. The three different treatment schedules of single-agent IMGN632 were either highly active ("Day 7" or "Day 11") or minimally active ("Day 14") in this study, resulting in the following T–C values and % ILS: i) the Day 7 schedule of IMGN632 (Group C) generated a T–C of >101 days and a >505% ILS (highly active); ii) the Day 11 schedule of IMGN632 (Group D) generated a T–C of 9.5 days and a 47.5% ILS (highly active); and iii) the Day 14 schedule of IMGN632 (Group E) generated a T–C of 6.5 days and a 32.5% ILS (minimally active).

The three different azacitidine plus IMGN632 combination therapy regimens outlined above resulted in the following anti-tumor activity: i) a T–C value of 23.5 days and a 117.5% ILS (highly active) for the combination of the IMGN632 Day 7 schedule plus azacitidine (Group F); ii) a T–C value of 60.5 days and a 302.5% ILS (highly active) for the combination of the IMGN632 Day 11 schedule plus azacitidine (Group G); and iii) a T–C value of 37 days and a 185% ILS (highly active) for the combination of the IMGN632 Day 14 schedule plus azacitidine (Group H). Comparing all three combination schedules, the combination schedule producing the highest % ILS was Group G (302.5% ILS), where the IMGN632 treatment began on the last azacitidine dosing day (day 11).

It is noteworthy that while all three of the IMGN632 plus azacitidine combination drug administration schedules tested resulted in highly active combinations, it was only the Group G (302.5% ILS) and the Group H (185% ILS) schedules, where the start of IMGN632 treatment was delayed relative to the start of azacitidine treatment, that produced a % ILS greater than that of the corresponding IMGN632 single agent regimens (Group D, "Day 11": 47.5% ILS, and Group E, "Day 14": 32.5% ILS, respectively). In contrast, the Group F drug combination administration schedule (which used the same starting day for both IMGN632 and azacitidine, Day 7) resulted in a 117.5% ILS which, while highly active, was markedly lower than that of the corresponding IMGN632 single agent group (Group C, "Day 7"), which produced a >505% ILS.

TABLE 6

Results from Combination of IMGN632 and Azacitidine in Molm-13 Disseminated Model

| Group/ Treatment | Treatment Days | Median Survival Time (Days) | Tumor Growth Delay (T-C, (Days) | % Increased Life Span (ILS) | Result |
| --- | --- | --- | --- | --- | --- |
| A) Vehicle | As below | 20 | — | — | — |
| B) Azacitidine, daily x 5, 3.5 mg/kg ("Day 7") | Days 7,8,9,10,11 | 26 | 6 | 30 | Minimally Active |
| C) IMGN632, QWx3, 0.3 µg/kg by DGN549 ("Day 7") | Days 7, 14, 21 | >121 | >101 | >505 | Highly Active |
| D) IMGN632, QWx3, 0.3 µg/kg by DGN549 ("Day 11") | Days 11, 18, 25 | 29.5 | 9.5 | 47.5 | Highly Active |
| E) IMGN632, QWx3, 0.3 µg/kg by DGN549 ("Day 14") | Days 14, 21, 28 | 26.5 | 6.5 | 32.5 | Minimally Active |
| F) IMGN632, QWx3, 0.3 µg/kg by DGN549 ("Day 7") and Azacitidine, daily x 5, 3.5 mg/kg ("Day 7") | IMGN632: Days 7, 14, 21; and Azacitidine: Days 7,8,9,10,11 | 43.5 | 23.5 | 117.5 | Highly Active |
| G) IMGN632, QWx3, 0.3 µg/kg by DGN549 ("Day 11") and Azacitidine, daily x 5, 3.5 mg/kg ("Day 7") | IMGN632: Days 11, 18, 25; and Azacitidine: Days 7,8,9,10,11 | 80.5 | 60.5 | 302.5 | Highly Active |
| H) IMGN632, QWx3, 0.3 µg/kg by DGN549 ("Day 14") and Azacitidine, daily x 5, 3.5 mg/kg ("Day 7") | IMGN632: Days 14, 21, 28; and Azacitidine: Days 7,8,9,10,11 | 57 | 37 | 185 | Highly Active |

Example 6

In Vivo Efficacy of the Combination of IMGN632 (QW×3) and Decitabine (QD×5) in Molm-13 Disseminated Model To test the efficacy of IMGN632, decitabine, or the combination of these two agents for the ability to decrease tumor burden in vivo, a disseminated tumor model was used as described in the protocol below.

Female NOD SCID mice were pre-treated with 150 mg/kg cyclophosphamide to partially ablate bone marrow in order to improve the engraftment of Molm-13 cells. The cyclophosphamide (Sigma, C0768, Lot #MKBX1822V) was dissolved in 0.9% NaCl and was administered intraperitoneally to the mice on day −2 prior to Molm-13 cell inoculation on day 0.

Following cyclophosphamide treatment as described above, the mice were each injected intravenously in the lateral tail vein with $2 \times 10^5$ Molm-13 cells (a human AML cell line) in 100 µl of serum-free medium on day 0 in the study. On day 5 post-Molm-13 inoculation, mice were randomized into study groups based on body weight. At 24 hours prior to each conjugate administration, for all groups receiving conjugate treatment (either alone or in combination with decitabine), the mice were injected intraperitoneally with 150 mg/kg of non-targeted chKTI antibody to block Fc receptors on the Molm-13 AML cells, preventing non-specific up-take of conjugate.

Mice received IMGN632 at a dose of 0.3 µg/kg by DGN549 (0.024 mg/kg by huCD123 Ab) once a week (QW) for three doses (×3) according to three different IMGN632 dosing schedules, either alone or in combination with decitabine. These three different IMGN632 dosing schedules were: i) days 7, 14, and 21 (referred to as "Day 7" for IMGN632); ii) days 11, 18, and 25 (referred to as "Day 11" for IMGN632); and iii) days 14, 21, and 28 (referred to as "Day 14" for IMGN632), where the noted start day of IMGN632 treatment was moved progressively away from day 0 (the day of Molm-13 inoculation) in the study time line.

Decitabine was given once a day (QD) at a dose of 0.75 mg/kg for 5 consecutive days (×5; days 7, 8, 9, 10, and 11; the "Day 7" schedule), either alone or in combination with IMGN632.

Mice were treated with a combination regimen of IMGN632 (QW×3) and 0.75 mg/kg decitabine (QD×5) according to one of three different dosing schedules for combining the two drugs: i) the Day 7 schedule for IMGN632 and the Day 7 schedule for decitabine (Group F), ii) the Day 11 schedule for IMGN632 and the Day 7 schedule for decitabine (Group G), or iii) the Day 14 schedule for IMGN632 and the Day 7 schedule for decitabine (Group H).

Figure 8:
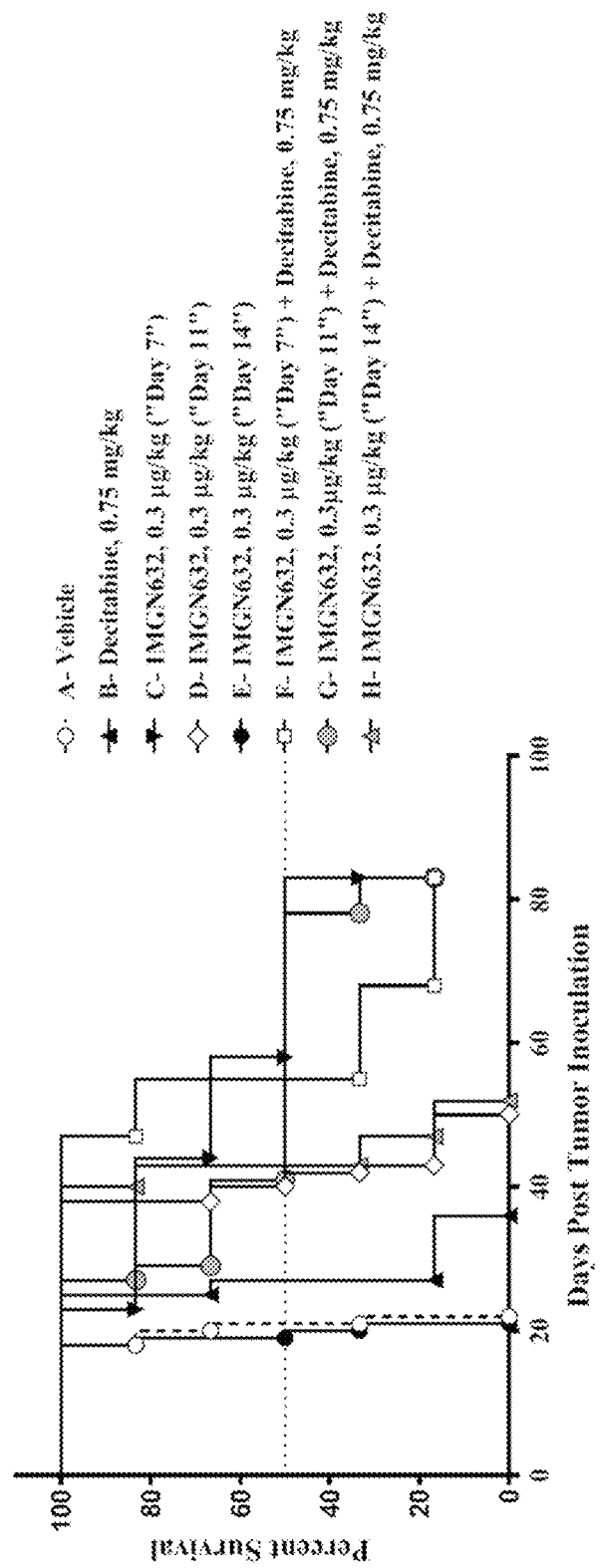
FIG. 8 shows the survival of mice as a function of time post Molm-3 tumor cell inoculation. Mice received IMGN632 alone (QW×3; 0.3 μg/kg) according to three different dosing schedules, decitabine alone (QD×5; 0.75 mg/kg), or a combination of IMGN632 (QW×3; 0.3 μg/kg) and decitabine alone (QD×5; 0.75 mg/kg).

The results are represented in Table 7 (below) and in FIG. 8.

Decitabine single-agent (Group B), administered at 0.75 mg/kg, QD×5, according to the Day 7 schedule, was minimally active in this study, resulting in a tumor growth delay (T–C value) of 6 days, and a 28.6% ILS (Increased Life Span), compared to vehicle treatment. The three different treatment schedules of single-agent IMGN632 were either highly active ("Day 7" or "Day 11") or inactive ("Day 14") in this study, resulting in the following T–C values and % ILS: i) the Day 7 schedule of IMGN632 (Group C) generated a T–C of 49.5 days and a 235.7% ILS (highly active); ii) the Day 11 schedule of IMGN632 (Group D) generated a T–C of 20 days and a 95.2% ILS (highly active); and iii) the Day 14 schedule of IMGN632 (Group E) generated a T–C of 0 days and a 0% ILS (inactive).

The three different decitabine plus IMGN632 combination therapy regimens outlined above resulted in the following anti-tumor activity: i) a T–C value of 34 days and a 161.9% ILS (highly active) for the combination of the IMGN632 Day 7 schedule plus decitabine (Group F); ii) a T–C value of 38.5 days and a 183.3% ILS (highly active) for the combination of the IMGN632 Day 11 schedule plus decitabine (Group G); and iii) a T–C value of 22 days and a 104.8% ILS (highly active) for the combination of the IMGN632 Day 14 schedule plus decitabine (Group H). Comparing all three combination schedules, the combination schedule producing the highest % ILS was used in Group G (183.3% ILS), where the IMGN632 treatment began on the last decitabine dosing day (which was day 11).

It is noteworthy that while all three of the IMGN632 plus decitabine combination drug administration schedules tested resulted in highly active combinations, it was only the Group G (183.3% ILS) and the Group H (104.8% ILS) schedules, where the start of IMGN632 treatment was delayed relative to the start of decitabine treatment, that produced a % ILS greater than that of the corresponding IMGN632 single agent regimens (Group D, "Day 11": 95.2% ILS, and Group E, "Day 14": 0% ILS, respectively). In contrast, the Group F drug combination administration schedule (which used the same starting day for both IMGN632 and decitabine, Day 7) resulted in a 161.9% ILS which, while highly active, was markedly lower than that of the corresponding IMGN632 single agent group (Group C, "Day 7"), which produced a 235.7% ILS.

TABLE 7

Results from Combination of IMGN632 and Decitabine in Molm-13 Disseminated Model

| Group/ Treatment | Treatment Days | Median Survival Time (Days) | Tumor Growth Delay (T-C, Days) | % Increased Life Span (ILS) | Result |
|---|---|---|---|---|---|
| A) Vehicle | As below | 21 | — | — | — |
| B) Decitabine, daily x 5, 0.75 mg/kg ("Day 7") | Days 7,8,9,10,11 | 27 | 6 | 28.6 | Minimally Active |
| C) IMGN632, QWx3, 0.3 µg/kg by DGN549 ("Day 7") | Days 7, 14, 21 | 70.5 | 49.5 | 235.7 | Highly Active |
| D) IMGN632, QWx3, 0.3 µg/kg by DGN549 ("Day11") | Days 11, 18, 25 | 41 | 20 | 95.2 | Highly Active |
| E) IMGN632, QWx3, 0.3 µg/kg by DGN549 ("Day 14") | Days 14, 21, 28 | 19.5 | 0 | 0 | Inactive |
| F) IMGN632, QWx3, 0.3 µg/kg by DGN549 ("Day 7") and Decitabine, daily x 5, 0.75 mg/kg ("Day 7") | IMGN632: Days 7, 14, 21; and Decitabine: Days 7,8,9,10,11 | 55 | 34 | 161.9 | Highly Active |
| G) IMGN632, QWx3, 0.3 µg/kg by DGN549 ("Day 11") and Decitabine, daily x 5, 0.75 mg/kg ("Day 7") | IMGN632: Days 11, 18, 25; and Decitabine: Days 7,8,9,10,11 | 59.5 | 38.5 | 183.3 | Highly Active |
| H) IMGN632, QWx3, 0.3 µg/kg by DGN549 ("Day 14") and Decitabine, daily x 5, 0.75 mg/kg ("Day 7") | IMGN632: Days 14, 21, 28; and Decitabine: Days 7,8,9,10,11 | 43 | 22 | 104.8 | Highly Active |

Example 7

In Vivo Efficacy of Combination of IMGN632 (Single Dose) and Azacitidine (QD×5) and Venetoclax (QD×28) in EOL-1 Subcutaneous Model To test the efficacy of IMGN632, the combination of azacitidine and venetoclax, or the combination of these three agents for the ability to decrease tumor burden in vivo, a subcutaneous tumor model was used as described in the protocol below.

Female athymic nude mice were each inoculated with $1 \times 10^7$ EOL-1 cells (a human AML cell line) in 100 µl of 50% Matrigel: 50% serum free medium (v/v) subcutaneously in the right flank. On day 12, which is 24 hours prior to conjugate administration for groups receiving conjugate treatment (either alone or in combination with azacitidine plus venetoclax), all the mice in these treatment groups were injected intraperitoneally with 150 mg/kg of non-targeted chKTI antibody to block Fc receptors on the EOL-1 AML cells, preventing non-specific up-take of conjugate. On day 12 post-EOL-1 inoculation, mice were randomized into study groups based on tumor volume.

On day 13 post-EOL-1 inoculation, the mice received a single intravenous injection, in the lateral tail vein, of either vehicle or 1 µg/kg (by DGN549; 0.080 mg/kg by huCD123Ab) of IMGN632. Venetoclax administration was also initiated on day 13, and the mice receiving venetoclax were given a single oral dose of 100 mg/kg venetoclax on each day of days 13 through 40, inclusive, post-cell implantation, for a total of 28 consecutive (×28) daily (QD) administrations. Azacitidine administration was also initiated on day 13, and the mice receiving azacitidine were given a single intraperitoneal dose of 3 mg/kg azacytidine daily (QD) on each of 5 consecutive days (×5). In the combination groups, the mice received administrations of IMGN632 and either venetoclax plus azacitidine or just azacitidine as outlined above.

Figure 9:
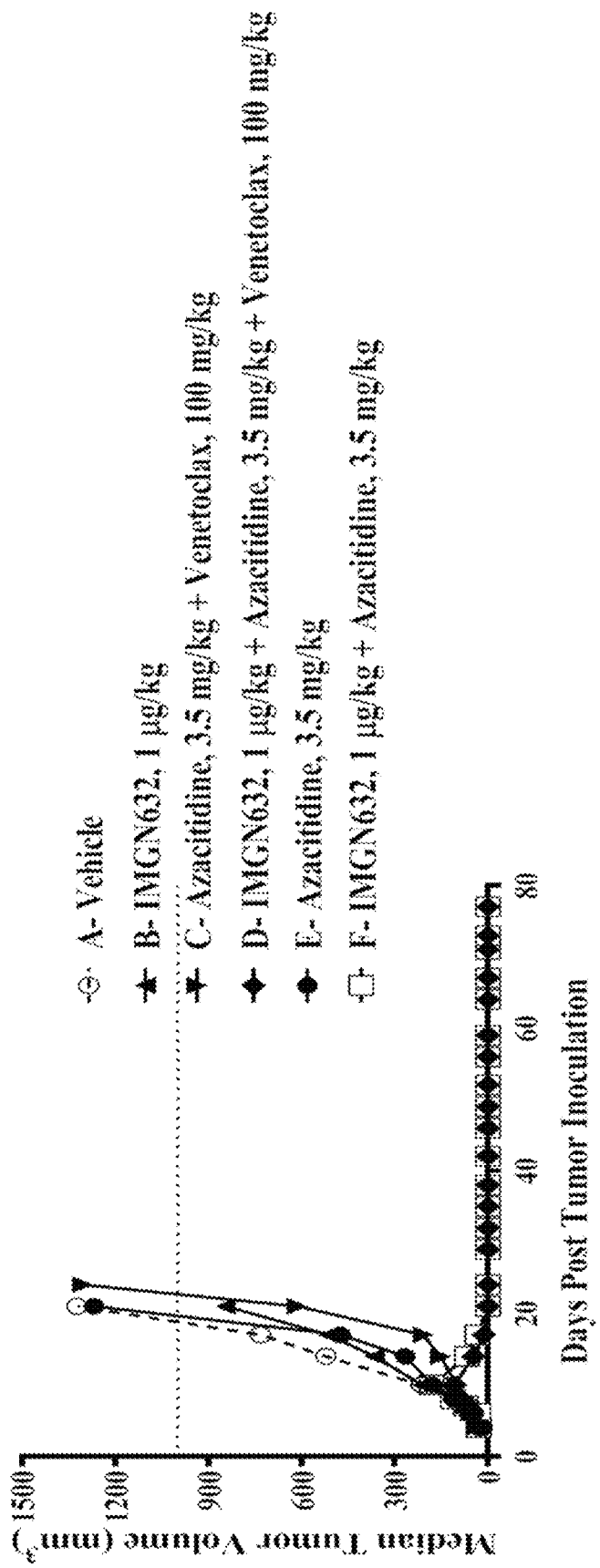
FIG. 9 shows the in vivo efficacy of a single dose of IMGN632 alone (1 μg/kg), venetoclax (QD×28; 100 mg/kg) and azacitidne (QD×5; 3 mg/kg), or the combination of IMGN632 (1 μg/kg) with venetoclax (QD×28; 100 mg/kg) and azacitidne (QD×5; 3 mg/kg) by plotting the median tumor volume (mm$^3$) as a function of days post inoculation of the EOL-1 cell line.

The results are represented in Table 8 and in FIG. 9.

A single dose of single-agent 1 µg/kg of IMGN632 resulted in a T/C value of 64% (inactive) and in 2/6 long-term complete regressions (tumor free survivors, TFS) at the end of the study (day 77). A single-agent regimen of 3 mg/kg of azacitidine, once-a-day (QD) for 5 days (×5), was inactive, resulting in a T/C of 96% and in 0/6 TFS on day 77. The two-drug combination of azacitidine (QD×5) and venetoclax (QD×28) was inactive, generating a 46% T/C and 1/6 TFS on day 77.

The three-drug combination of IMGN632, azacitidine, and venetoclax was highly active, generating a 0% T/C and 5/6 TFS at end of study. The three-drug combination produced a % T/C (0%) that was smaller than that generated by either IMGN632 single-agent (64%) or the two-drug combination of azacitidine plus venetoclax (46%), indicating that the three-drug combination was more effective at slowing tumor growth than was IMGN632 alone or the two-drug combination of azacitidine plus venetoclax.

The two-drug combination of IMGN632 and azacitidine was also highly active, generating a 0% T/C and 4/6 TFS at end of study. The two-drug combination of IMGN632 and azacitidine produced a % T/C (0%) that was smaller than that generated by either IMGN632 single-agent (64%) or azacitidine single-agent (96%), indicating that the two-drug combination was more effective at slowing tumor growth than was either corresponding single-agent treatment.

TABLE 8

Results from Combination of IMGN632, Azacitidine, Venetoclax in EOL-1 Model

| Group/Treatment | Treatment Days | % T/C (Day 21) | PR | CR | Tumor Free Survivors (Day 77) | Result |
|---|---|---|---|---|---|---|
| A) Vehicle | — | — | 1/6 | 1/6 | 1/6 | — |
| B) IMGN632, 1 µg/kg by DGN549, single dose | Day 13 | 64 | 2/6 | 2/6 | 2/6 | Inactive |
| C) Azacitidine, 3 mg/kg, daily x5, and Venetoclax, 100 mg/kg, daily x28 | Azacitidine: Days 13, 14, 15, 16, 17; Venetoclax: Days 13 through 40 (28 days total) | 46 | 1/6 | 1/6 | 1/6 | Inactive |
| D) IMGN632, 1 µg/kg by DGN549, single dose, and Azacitidine, 3 mg/kg, daily x5, and Venetoclax, 100 mg/kg, daily x28 | IMGN632: Day 13; Azacitidine: Days 13, 14, 15, 16, 17; Venetoclax: Days 13 through 40 (28 days total) | 0 | 5/6 | 5/6 | 5/6 | Highly Active |
| E) Azacitidine, 3 mg/kg, daily x5 | Days 13, 14, 15, 16, 17 | 96 | 1/6 | 1/6 | 0/6 | Inactive |
| F) IMGN632, 1 µg/kg by DGN549, single dose and Azacitidine, 3 mg/kg, daily x5 | IMGN632: Day 13; Azacitidine: Days 13, 14, 15, 16, 17 | 0 | 4/6 | 4/6 | 4/6 | Highly Active |

Example 8

In Vivo Efficacy of the Combination of IMGN632 (QW×3), Azacitidine (QD×5), and Venetoclax (QD×28) in Molm-13 Disseminated Model To test the efficacy of IMGN632, venetoclax, the combination of azacitidine plus venetoclax, the combination of IMGN632 plus venetoclax, or the triple combination of IMGN632, azacitidine, and venetoclax for the ability to decrease tumor burden in vivo, a disseminated tumor model was used as described in the protocol below.

Female NOD SCID mice were pre-treated with 150 mg/kg cyclophosphamide to partially ablate bone marrow in order to improve the engraftment of Molm-13 cells. The cyclophosphamide (Sigma, C0768, Lot #MKBX1822V) was dissolved in 0.9% NaCl and was administered intraperitoneally to the mice on day −2 prior to Molm-13 cell inoculation on day 0.

Following cyclophosphamide treatment as described above, the mice were each injected intravenously in the lateral tail vein with 2×10$^5$ Molm-13 cells (a human AML cell line) in 100 µl of serum-free medium on day 0 in the study. At 24 hours prior to each conjugate administration, for all groups receiving conjugate treatment (either alone, or in combination with venetoclax, or in combination with azacitidine plus venetoclax), the mice were injected intraperitoneally with 150 mg/kg of non-targeted chKTI antibody to block Fc receptors on the Molm-13 AML cells, preventing non-specific up-take of conjugate.

On days 11, 18, and 25 post-Molm-13 inoculation, the mice received a single intravenous injection, in the lateral tail vein, of either vehicle or 0.3 µg/kg (by DGN549; 0.024 mg/kg by huCD123Ab) of IMGN632. Venetoclax administration was initiated on day 7 post-cell inoculation, and the mice receiving venetoclax were given a single oral dose of 100 mg/kg venetoclax on each day of days 7 through 34, inclusive, for a total of 28 consecutive (×28) daily (QD) administrations. Azacitidine administration was also initiated on day 7, and the mice receiving azacitidine were given a single intraperitoneal dose of 3.5 mg/kg azacitidine daily (QD) on each of 5 consecutive days (×5). In the combination group of azacitidine and venetoclax or in the triple combination group of all three agents, the mice received administrations of IMGN632, venetoclax, and azacitidine as outlined above.

Figure 10A:
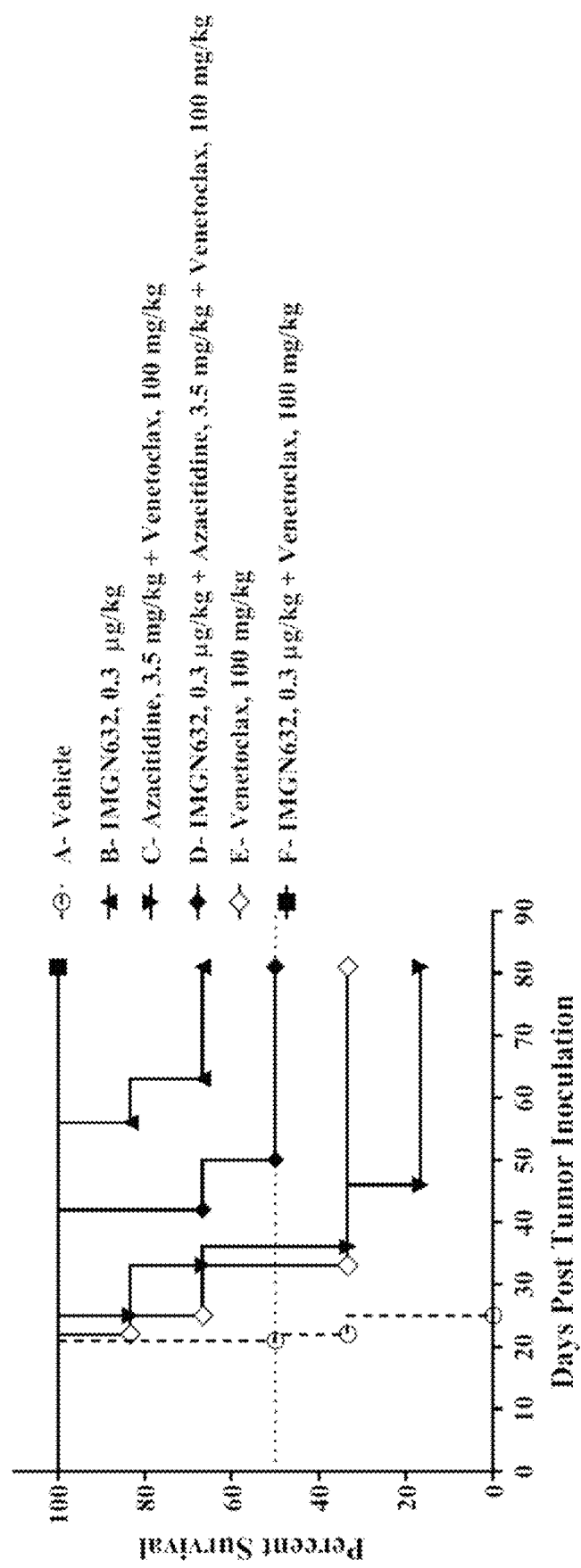
FIGS. 10A and 10B show the survival of mice as a function of time post Molm-3 tumor cell inoculation. Mice received IMGN632 alone (QW×3), venetoclax (QD×28) and azacitidne (QD×5), or the combination of IMGN632 (QW×3) with venetoclax (QD×28) and azacitidne (QD×5).

The results up to 80 days post-tumor cell inoculation are represented in Table 9A (below) and in FIG. 10A.

IMGN632 single-agent treatment (Group B) resulted in a tumor growth delay (T–C value) of >59.5 days, and in a >277% Increased Life Span (% ILS), compared to vehicle treatment. Venetoclax single-agent treatment (Group E) resulted in a T–C of 11.5 days and in a 53.5% ILS (highly active). The two-drug combination of azacitidine and venetoclax (Group C) resulted in a T–C of 14.5 days and in a 67.4% ILS (highly active). The two-drug combination of IMGN632 and venetoclax (Group F) resulted in a >59.5 T–C and in a >277% ILS (highly active), which are T–C and % ILS values greater than those generated by venetoclax alone, indicating that the addition of IMGN632 to venetoclax offers an additional benefit compared to venetoclax single-agent treatment. The three-drug combination of IMGN632 and azacitidine and venetoclax (Group D) resulted in a T–C of >59.5 days and in a >277% ILS (highly active), which are T–C and % ILS values greater than those generated by the two-drug combination of azacitidine and venetoclax, indicating that the addition of IMGN632 to the two-drug combination of azacitidine and venetoclax offers an additional benefit compared to treatment with simply azacitidine and venetoclax.

TABLE 9A:

80-Day Results from Combination of IMGN632, Azacitidine, and Venetoclax in Molm-13 Model

| Group/Treatment | Treatment Days | Median Survival Time (Days) | Tumor Growth Delay (T–C, Days) | % Increased Life Span (ILS) | Result |
|---|---|---|---|---|---|
| A) Vehicle | As below | 21.5 | — | — | — |
| B) IMGN632, 0.3 µg/kg by DGN549, weekly x 3 | Days 11, 18, 25 | >81 | >59.5 | >277 | Highly Active |
| C) Azacitidine, 3.5 mg/kg, daily x5; and Venetoclax, 100 mg/kg, daily x 28 | Azacitidine: Days 7,8,9,10,11; and Venetoclax: Days 7 through 34 (28 days total) | 36 | 14.5 | 67.4 | Highly Active |
| D) IMGN632, 0.3 µg/kg by DGN549, weekly x 3; and Azacitidine, 3.5 mg/kg, daily x5; and Venetoclax, 100 mg/kg, daily x 28 | IMGN632: Days 11,18, 25; and Azacitidine: Days 7,8,9,10,11; and Venetoclax: Days 7 through 34 (28 days total) | >81 | >59.5 | >277 | Highly Active |
| E) Venetoclax, 100 mg/kg, daily x 28 | Venetoclax: Days 7 through 34 (28 days total) | 33 | 11.5 | 53.4 | Highly Active |
| F) IMGN632, 0.3 µg/kg by DGN549, weekly x 3; and Venetoclax, 100 mg/kg, daily x 28 | IMGN632: Days 11, 18,25; and Venetoclax: Days 7 through 34 (28 days total) | >81 | >59.5 | >277 | Highly Active |

Figure 10B:
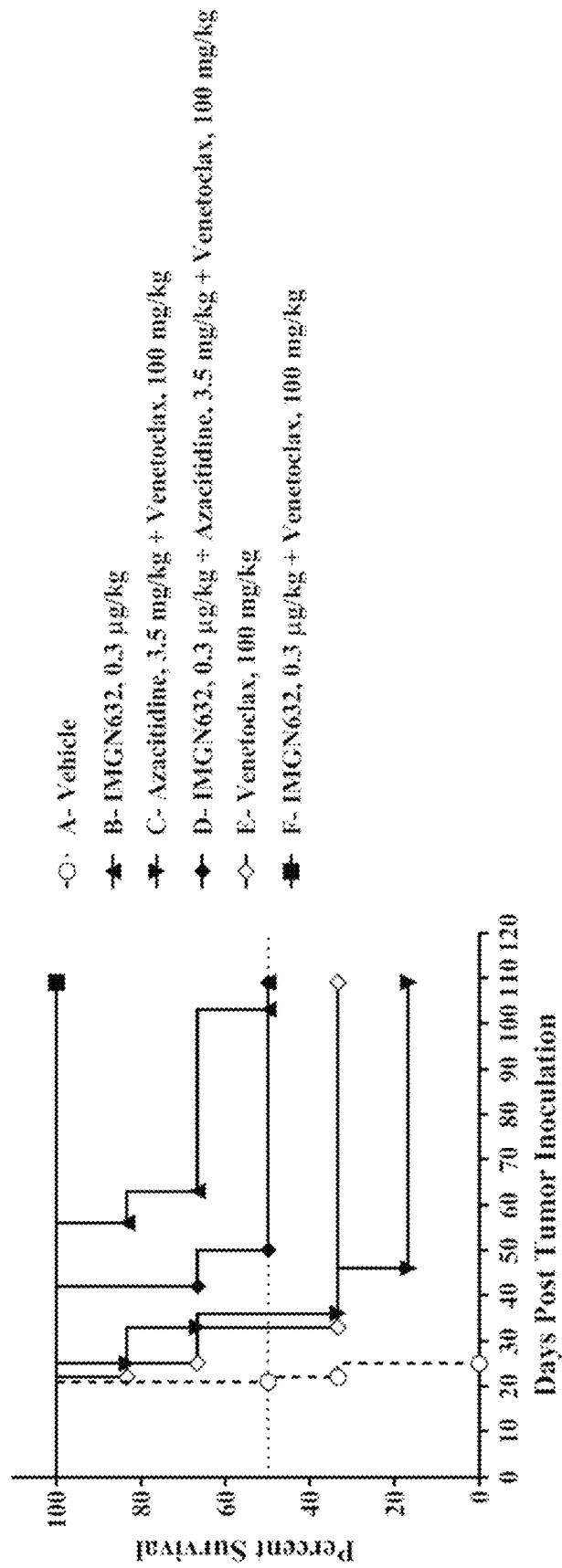

The results up to 109 days post-tumor cell inoculation are represented in Table 9B (below) and in FIG. 10B. IMGN632 single-agent treatment (Group B) resulted in a tumor growth delay (T–C value) of >87.5 days, and in a >407% Increased Life Span (% ILS), compared to vehicle treatment. Venetoclax single-agent treatment (Group E) resulted in a T–C of 11.5 days and in a 53.5% ILS (highly active). The two-drug combination of azacitidine and venetoclax (Group C) resulted in a T–C of 14.5 days and in a 67.4% ILS (highly active). The two-drug combination of IMGN632 and venetoclax (Group F) resulted in a >87.5 T–C and in a >407% ILS (highly active), which are T–C and % ILS values greater than those generated by venetoclax alone, indicating that the addition of IMGN632 to venetoclax offers an additional benefit compared to venetoclax single-agent treatment. The three-drug combination of IMGN632 and azacitidine and venetoclax (Group D) resulted in a T–C of >87.5 days and in a >407% ILS (highly active), which are T–C and % ILS values greater than those generated by the two-drug combination of azacitidine and venetoclax, indicating that the addition of IMGN632 to the two-drug combination of azacitidine and venetoclax offers an additional benefit compared to treatment with simply azacitidine and venetoclax.

TABLE 9B: 109-Day

Results from Combination of IMGN632, Azacitidine, and Venetoclax in Molm-13 Model

| Group/ Treatment | Treatment Days | Median Survival Time (Days) | Tumor Growth Delay (T-C, Days) | % Increased Life Span (ILS) | Result |
|---|---|---|---|---|---|
| A) Vehicle | As below | 21.5 | — | — | — |
| B) IMGN632, 0.3 μg/kg by DGN549, weekly x 3 | Days 11, 18, 25 | >109 | >87.5 | >407 | Highly Active |
| C) Azacitidine, 3.5 mg/kg, daily x5; and Venetoclax, 100 mg/kg, daily x 28 | Azacitidine: Days 7,8,9, 10,11; and Venetoclax: Days 7 through 34 (28 days total) | 36 | 14.5 | 67.4 | Highly Active |
| D) IMGN632, 0.3 μg/kg by DGN549, weekly x 3; and Azacitidine, 3.5 mg/kg, daily x5; and Venetoclax, 100 mg/kg, daily x 28 | IMGN632: Days 11,18, 25; and Azacitidine: Days 7,8,9, 10,11; and Venetoclax: Days 7 through 34 (28 days total) | >109 | >87.5 | >407 | Highly Active |
| E) Venetoclax, 100 mg/kg, daily x 28 | Venetoclax: Days 7 through 34 (28 days total) | 33 | 11.5 | 53.4 | Highly Active |
| F) IMGN632, 0.3 μg/kg by DGN549, weekly x 3; and Venetoclax, 100 mg/kg, daily x 28 | IMGN632: Days 11,18,25; and Venetoclax: Days 7 through 34 (28 days total) | >109 | >87.5 | >407 | Highly Active |

Example 9

In Vivo Efficacy of the Combination of IMGN632 (QW×3), Azacitidine (QD×5), and Venetoclax (QD×28) in MV4-11 Disseminated Model To test the efficacy of IMGN632, the combination of azacitidine and venetoclax, or the combination of these three agents for the ability to decrease tumor burden in vivo, a disseminated tumor model was used as described in the protocol below.

Female NOD SCID mice were pre-treated with 150 mg/kg cyclophosphamide to partially ablate bone marrow in order to improve the engraftment of MV4-11 cells. The cyclophosphamide (Sigma, C0768, Lot #MKBX1822V) was dissolved in 0.9% NaCl and was administered intraperitoneally to the mice on days −3 and −2 prior to MV4-11 cell inoculation on day 0.

Following cyclophosphamide treatment as described above, the mice were each injected intravenously in the lateral tail vein with 3×10⁶ MV4-11 cells (a human AML cell line) in 100 μl of serum-free medium on day 0 in the study. On day 3 post-MV4-11 inoculation, mice were randomized into the study groups based on body weight. At 24 hours prior to each conjugate administration, for all groups receiving conjugate treatment (either alone, or in combination with azacitidine and venetoclax), the mice were injected intraperitoneally with 150 mg/kg of non-targeted chKTI antibody to block Fc receptors on the MV4-11 AML cells, preventing non-specific up-take of conjugate.

On days 25, 32, and 39 post-MV4-11 inoculation, the mice received a single intravenous injection, in the lateral tail vein, of either vehicle or 1 μg/kg (by DGN549; 0.080 mg/kg by huCD123Ab) of IMGN632. Venetoclax administration was initiated on day 21 post-cell inoculation, and the mice receiving venetoclax were given a single oral dose of 100 mg/kg venetoclax on each day of days 21 through 48, inclusive, for a total of 28 consecutive (×28) daily (QD) administrations. Azacitidine administration was also initiated on day 21, and the mice receiving azacitidine were given a single intraperitoneal dose of either 4.5 mg/kg or 3 mg/kg azacitidine daily (QD) on each of 5 consecutive days (×5). In combination group of azacitidine plus venetoclax or in the triple combination group of the three agents, the mice received administrations of IMGN632, venetoclax and azacitidine as outlined above.

Figure 11:
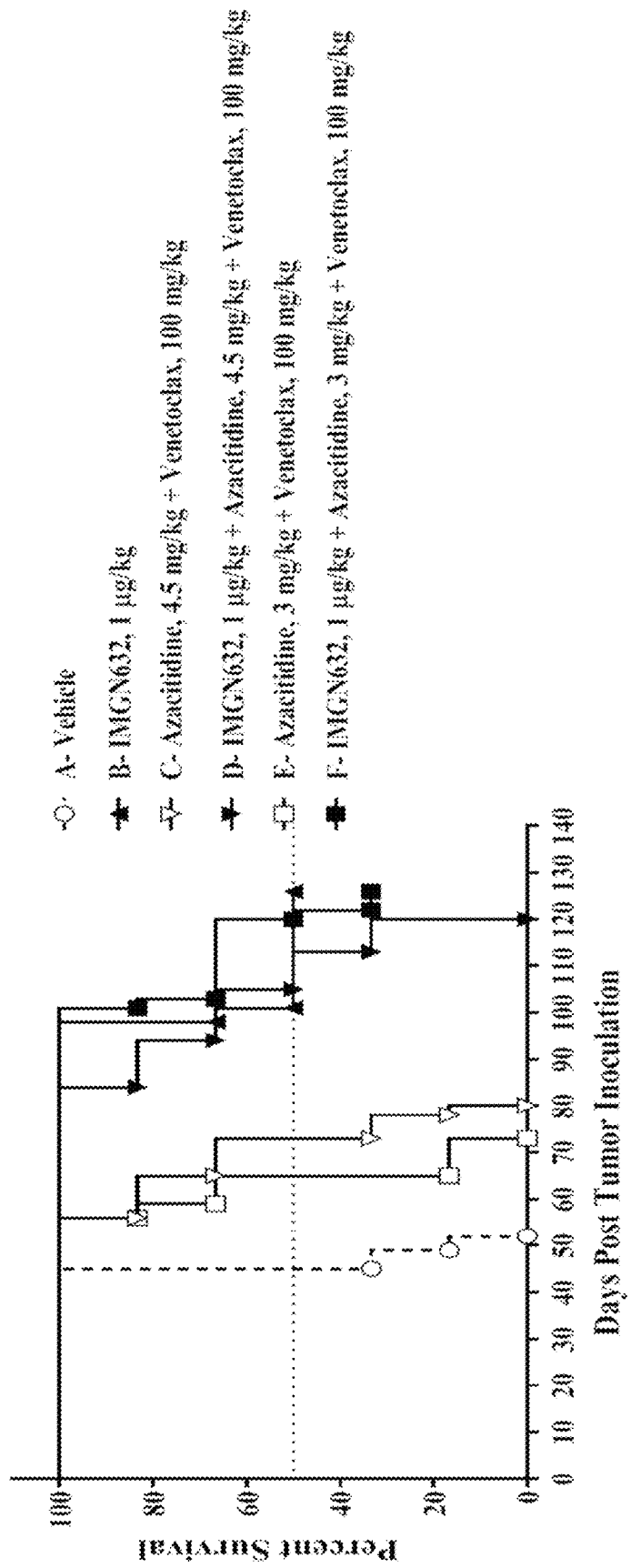
FIG. 11 shows the survival of mice as a function of time post MV4-11 tumor cell inoculation. Mice received IMGN632 alone (QW×3), venetoclax (QD×28) and azacitidne (QD×5), or the combination of IMGN632 (QW×3) with venetoclax (QD×28) and azacitidne (QD×5).

The results are represented in Table 10 and in FIG. 11.

IMGN632 single-agent treatment (Group B) resulted in a tumor growth delay (T–C value) of >81 days, and in a >180% Increased Life Span (% ILS), compared to vehicle treatment. The two-drug combination of azacitidine (4.5 mg/kg) and venetoclax (Group C) resulted in a T–C of 28 days and in a 62.2% ILS (highly active). The three-drug combination of IMGN632 and azacitidine (4.5 mg/kg) and venetoclax (Group D) resulted in a T–C of 64 days and in a >142.2% ILS (highly active), which are T–C and % ILS values greater than those generated by the two-drug combination of azacitidine (4.5 mg/kg) and venetoclax, indicating that the addition of IMGN632 to the two-drug combination of azacitidine and venetoclax offers an additional benefit compared to treatment with simply azacitidine and venetoclax.

The two-drug combination of azacitidine (3 mg/kg) and venetoclax (Group E) resulted in a T–C of 20 days and in a 44.4% ILS (active). The three-drug combination of IMGN632 and azacitidine (3 mg/kg) and venetoclax (Group D) resulted in a T–C of 76 days and in a 168.9% ILS (highly active), which are T–C and % ILS values greater than those generated by the two-drug combination of azacitidine (3 mg/kg) and venetoclax, indicating that the addition of IMGN632 to the two-drug combination of azacitidine and venetoclax offers an additional benefit compared to treatment with simply azacitidine and venetoclax.

TABLE 10

Results from the Combination of IMGN632, Azacitidine, and Venetoclax in MV4-11 Model

| Group/ Treatment | Treatment Days | Median Survival Time (Days) | Tumor Growth Delay (T-C, Days) | % Increased Life Span (ILS) | Result |
|---|---|---|---|---|---|
| A) Vehicle | As below | 45 | — | — | — |
| B) IMGN632, 1 μg/kg by DGN549, weekly x 3 | Days 25,32,39 | >126 | >81 | >180 | Highly Active |
| C) Azacitidine, 4.5 mg/kg, daily x 5; and Venetoclax, 100 mg/kg, daily x 28 | Azacitidine: Days 21,22,23, 24,25; and Venetoclax: Days 21 through 48 (28 days total) | 73 | 28 | 62.2 | Highly Active |

TABLE 10-continued

Results from the Combination of IMGN632,
Azacitidine, and Venetoclax in MV4-11 Model

| Group/ Treatment | Treatment Days | Median Survival Time (Days) | Tumor Growth Delay (T-C, Days) | % Increased Life Span (ILS) | Result |
|---|---|---|---|---|---|
| D) IMGN632, 1 μg/kg by , DGN549 weekly x 3; and Azacitidine, 4.5 mg/kg, daily x 5; and Venetoclax, 100 mg/kg, daily x 28 | IMGN632: Days 25,32, 39; and Azacitidine: Days 21,22,23, 24,25; and Venetoclax: Days 21 through 48 (28 days total) | 109 | 64 | 142.2 | Highly Active |
| E) Azacitidine, 3 mg/kg, daily x 5; and Venetoclax, 100 mg/kg, daily x 28 | Azacitidine: Days 21,22,23, 24,25; and Venetoclax: Days 21 through 48 (28 days total) | 65 | 20 | 44.4 | Active |
| F) IMGN632, 1 μg/kg by DGN549 weekly x 3; and Azacitidine, 3 mg/kg, daily x 5; and Venetoclax, 100 mg/kg, daily x 28 | IMGN632: Days 25, 32,39; and Azacitidine: Days 21,22,23, 24,25; and Venetoclax: Days 21 through 48 (28 days total) | 121 | 76 | 168.9 | Highly Active |

Example 10

Administration of IMGN632 Combinations to Humans

Unfit frontline and replasted/refactory BPDCN and relapsted/refractory ALL patients are treated at the recommend phase 2 dose (RP2D) of IMGN632 monotherapy as 0.045 mg/kg once every 21-day cycle (Q3W). Based on the experiments above, the following three dosing schedules were selected for administration to human subjects:

Schedule A: IMGN632+Azacitidine:

The cycle for IMGN632 and azacitdine is 28 days. In this 28-day cycle, azacitidine is given at 75 mg/m² subcutaneously (SC) or intravenous (IV) daily on Days 1 to 7. Alternatively, azacitidine can be given at 75 mg/m² subcutaneously (SC) or intravenous (IV) daily on Days 1 to 5. Administration of IMGN632 is initiated on Day 7 after the last azacitidine dose. IMGN632 is administered at a total dose of 0.015 mg/kg, 0.045 mg/kg, 0.09 mg/kg, or 0.18 mg/kg per 28-day cycle. For example, IMGN632 is administered at a dose of 0.015 mg/kg, 0.045 mg/kg, or 0.09 mg/kg once (i.e., on Day 7) every 28-day cycle. IMGN632 can also be administered at a dose of 0.03 mg/kg once (e.g., on Day 7) every 28-day cycle. Alternatively, IMGN632 is administered at a dose of 0.015 mg/kg, 0.03 mg/kg, or 0.06 mg/kg three times (i.e., on Days 7, 10, and 14) every 28-day cycle.

If after Cycle 1, patients experience toxicity associated with azacitidine (e.g., cytopenias), the azacitidine dosing may be reduced to 5 days by omitting treatments on Days 1 and 2 and administering azacitidine on Days 3 to 7 in subsequent cycles.

There can a total of 2-12 cycles administered. Then, IMGN632 can be given as maintenance therapy once every three weeks (e.g., on Day 1 of a 21-day cycle at dose of 0.015 mg/kg, 0.045 mg/kg, or 0.09 mg/kg) or three times every three weeks (e.g., on Days 1, 4, and 8 of a 21-day cycle at a dose of 0.015 mg/kg, 0.03 mg/kg, or 0.06 mg/kg).

IMGN632 Q4W+Azacitidine Dosing Schedule:

| Day | 1 | 2 | 3 | 4 |
|---|---|---|---|---|
| Aza | 75 mg/m² | 75 mg/m² | 75 mg/m² | 75 mg/m² |
| IMGN632 | 0 | 0 | 0 | 0 |
| Day | 5 | 6 | 7 | 8 |
| Aza | 75 mg/m² | 75 mg/m² | 75 mg/m² | 0 |
| IMGN632 | 0 | 0 | 0.015, 0.045, or 0.09 mg/kg | 0 |
| Day | 9 | 10 | 11 | 12 |
| Aza | 0 | 0 | 0 | 0 |
| IMGN632 | 0 | 0 | 0 | 0 |
| Day | 13 | 14 | 15 | 16 |
| Aza | 0 | 0 | 0 | 0 |
| IMGN632 | 0 | 0 | 0 | 0 |
| Day | 17 | 18 | 19 | 20 |
| Aza | 0 | 0 | 0 | 0 |
| IMGN632 | 0 | 0 | 0 | 0 |
| Day | 21 | 22 | 23 | 24 |
| Aza | 0 | 0 | 0 | 0 |
| IMGN632 | 0 | 0 | 0 | 0 |
| Day | 25 | 26 | 27 | 28 |
| Aza | 0 | 0 | 0 | 0 |
| IMGN632 | 0 | 0 | 0 | 0 |

IMGN632 Days 7, 10, and 14+Azacitidine Dosing Schedule:

| Day | 1 | 2 | 3 | 4 |
|---|---|---|---|---|
| Aza | 75 mg/m² | 75 mg/m² | 75 mg/m² | 75 mg/m² |
| IMGN632 | 0 | 0 | 0 | 0 |
| Day | 5 | 6 | 7 | 8 |
| Aza | 75 mg/m² | 75 mg/m² | 75 mg/m² | 0 |
| IMGN632 | 0 | 0 | 0.015, 0.03, or 0.06 mg/kg | 0 |
| Day | 9 | 10 | 11 | 12 |
| Aza | 0 | 0 | 0 | 0 |
| IMGN632 | 0 | 0.015, 0.03, or 0.06 mg/kg | 0 | 0 |
| Day | 13 | 14 | 15 | 16 |
| Aza | 0 | 0 | 0 | 0 |
| IMGN632 | 0 | 0.015, 0.03, or 0.06 mg/kg | 0 | 0 |

-continued

| Day | 17 | 18 | 19 | 20 |
|---|---|---|---|---|
| Aza | 0 | 0 | 0 | 0 |
| IMGN632 | 0 | 0 | 0 | 0 |
| Day | 21 | 22 | 23 | 24 |
| Aza | 0 | 0 | 0 | 0 |
| IMGN632 | 0 | 0 | 0 | 0 |
| Day | 25 | 26 | 27 | 28 |
| Aza | 0 | 0 | 0 | 0 |
| IMGN632 | 0 | 0 | 0 | 0 |

Schedule B: IMGN632+Venetoclax

The cycle for IMGN632 and venetoclax is 21 days. In the first Cycle, venetoclax is given by mouth (PO) at 100 mg on Day 1, 200 mg on Day 2, and 400 mg on all subsequent days (Days 3-21); in subsequent Cycles, venetoclax is administered at the maximum dose (e.g., 400 mg) on all days). Administration of IMGN632 is initiated on Day 7 after the seventh venetoclax dose. IMGN632 is administered at a total dose of 0.015 mg/kg, 0.045 mg/kg, 0.09 mg/kg, or 0.18 mg/kg per 21-day cycle. For example, IMGN632 is administered at a dose of 0.015 mg/kg, 0.045 mg/kg, or 0.09 mg/kg once (e.g., on Day 7) every 21-day cycle. IMGN632 can also be administered at a dose of 0.03 mg/kg once (e.g., on Day 7) every 28-day cycle. Alternatively, IMGN632 is administered at a dose of 0.015 mg/kg, 0.03 mg/kg, or 0.06 mg/kg three times (i.e., on Days 7, 10, and 14) every 21-day cycle.

Per the venetoclax FDA label, strong cytochrome P450 (CYP)3A inhibitors e.g., voriconazole and posaconazole, are avoided. If patients are on a moderate CYP3A inhibitor (e.g., Cresemba), venetoclax doses are capped at 200 mg.

If after Cycle 1, patients experience toxicity associated with venetoclax (e.g., cytopenias), venetoclax dosing may be reduced to Days 1 to 14 (or 1 to 7). Ventoclax dosing my also be reduced to Days 1 to 8.

There can a total of 2-12 cycles administered. Then, IMGN632 can be given as maintenance therapy once every three weeks (e.g., on Day 1 of a 21-day cycle at dose of 0.015 mg/kg, 0.045 mg/kg, or 0.09 mg/kg) or three times every three weeks (e.g., on Days 1, 4, and 8 of a 21-day cycle at a dose of 0.015 mg/kg, 0.03 mg/kg, or 0.06 mg/kg).

IMGN632 Q3W+Venetoclax Dosing Schedule:

| Day | 1 | 2 | 3 |
|---|---|---|---|
| Venetoclax | 100 mg (Cycle 1) 400 mg (Cycles ≥2) | 200 mg (Cycle 1) 400 mg (Cycles ≥2) | 400 mg |
| IMGN632 | 0 | 0 | 0 |
| Day | 4 | 5 | 6 |
| Venetoclax | 400 mg | 400 mg | 400 mg |
| IMGN632 | 0 | 0 | 0 |
| Day | 7 | 8 | 9 |
| Venetoclax | 400 mg | 400 mg | 400 mg |
| IMGN632 | 0.015, 0.045, or 0.09 mg/kg | 0 | 0 |
| Day | 10 | 11 | 12 |
| Venetoclax | 400 mg | 400 mg | 400 mg |
| IMGN632 | 0 | 0 | 0 |
| Day | 13 | 14 | 15 |
| Venetoclax | 400 mg | 400 mg | 400 mg |
| IMGN632 | 0 | 0 | 0 |
| Day | 16 | 17 | 18 |
| Venetoclax | 400 mg | 400 mg | 400 mg |
| IMGN632 | 0 | 0 | 0 |
| Day | 19 | 20 | 21 |
| Venetoclax | 400 mg | 400 mg | 400 mg |
| IMGN632 | 0 | 0 | 0 |

IMGN632 Days 7, 10, and 14+Venetoclas Dosing Schedule:

| Day | 1 | 2 | 3 |
|---|---|---|---|
| Venetoclax | 100 mg (Cycle 1) 400 mg (Cycles ≥2) | 200 mg (Cycle 1) 400 mg (Cycles ≥2) | 400 mg |
| IMGN632 | 0 | 0 | 0 |
| Day | 4 | 5 | 6 |
| Venetoclax | 400 mg | 400 mg | 400 mg |
| IMGN632 | 0 | 0 | 0 |
| Day | 7 | 8 | 9 |
| Venetoclax | 400 mg | 400 mg | 400 mg |
| IMGN632 | 0.015, 0.03, or 0.06 mg/kg | 0 | 0 |
| Day | 10 | 11 | 12 |
| Venetoclax | 400 mg | 400 mg | 400 mg |
| IMGN632 | 0.015, 0.03, or 0.06 mg/kg | 0 | 0 |
| Day | 13 | 14 | 15 |
| Venetoclax | 400 mg | 400 mg | 15 400 mg |
| IMGN632 | 0 | 0.015, 0.03, or 0.06 mg/kg | 0 |
| Day | 16 | 17 | 18 |
| Venetoclax | 400 mg | 400 mg | 400 mg |
| IMGN632 | 0 | 0 | 0 |
| Day | 19 | 20 | 21 |
| Venetoclax | 400 mg | 400 mg | 400 mg |
| IMGN632 | 0 | 0 | 0 |

Schedule C: IMGN632+Azacitidine+Venetoclax

The cycle for IMGN632, azacitidine, and venetoclx is 28 days. In this 28-day cycle, azacitidine is given at 75 mg/m² subcutaneously (SC) or intravenous (IV) daily on Days 1 to 7. Alternatively, azacitidine can be given at 75 mg/m² subcutaneously (SC) or intravenous (IV) daily on Days 1 to 5.

In the first Cycle, venetoclax is given by mouth (PO) at 100 mg on Day 1, 200 mg on Day 2, and 400 mg on all subsequent days (Days 3-28); in subsequent Cycles, venetoclax is administered by mouth (PO) in the first Cycle the maximum dose (e.g., 400 mg on all days). Alternatively, venetoclax can be given at 100 mg on Day 1, 200 mg on Day 2, and 400 mg on subsequent Days 3-8, Days 3-14, or Days 3-21 of the 28-day cycle; and in subsequent Cycles, by mouth (PO) at the maximum dose (e.g., 400 mg) on Days 1-8, Days 1-14, Days 1-18, or Days 1-21 of the 28-day cycle.

Administration of IMGN632 is initiated on Day 7, e.g., after the seventh venetoclax and azacitdine doses. IMGN632 is administered at a total dose of 0.015 mg/kg, 0.045 mg/kg, 0.09 mg/kg, or 0.18 mg/kg per 28-day cycle. For example, IMGN632 is administered at a dose of 0.015 mg/kg, 0.045 mg/kg, or 0.09 mg/kg once (e.g., on Day 7) every 28-day cycle. IMGN632 can also be administered at a dose of 0.03 mg/kg once (e.g., on Day 7) every 28-day cycle. Alternatively, IMGN632 is administered at a dose of 0.015 mg/kg, 0.03 mg/kg, or 0.06 mg/kg three times (i.e., on Days 7, 10, and 14) every 28-day cycle.

There can be a total of 2-12 cycles administered. Then, IMGN632 can be given as maintenance therapy once every three weeks (e.g., on Day 1 of a 21-day cycle at dose of 0.015 mg/kg, 0.045 mg/kg, or 0.09 mg/kg) or three times every three weeks (e.g., on Days 1, 4, and 8 pf a 21-day cycle at a dose of 0.015 mg/kg, 0.03 mg/kg, or 0.06 mg/kg). IMGN632 can also be given as maintenance therapy once every three weeks (e.g., on Day 1 of a 21-day cycle at dose of 0.03 mg/kg).

IMGN632 Q3W+Azacitidine+Venetoclax Dosing Schedule

| Day | 1 | 2 | 3 | 4 |
|---|---|---|---|---|
| Aza | 75 mg/m² | 75 mg/m² | 75 mg/m² | 75 mg/m² |
| Venetoclax | 100 mg (Cycle 1) 400 mg (Cycles ≥2) | 200 mg (Cycle 1) 400 mg (Cycles ≥2) | 400 mg | 400 mg |
| IMGN632 | 0 | 0 | 0 | 0 |
| Day | 5 | 6 | 7 | 8 |
| Aza | 75 mg/m² | 75 mg/m² | 75 mg/m² | 0 |
| Venetoclax | 400 mg | 400 mg | 400 mg | 400 mg |
| IMGN632 | 0 | 0 | 0.015, 0.045, or 0.09 mg/kg | 0 |
| Day | 9 | 10 | 11 | 12 |
| Aza | 0 | 0 | 0 | 0 |
| Venetoclax | 400 mg | 400 mg | 400 mg | 400 mg |
| IMGN632 | 0 | 0 | 0 | 0 |
| Day | 13 | 14 | 15 | 16 |
| Aza | 0 | 0 | 0 | 0 |
| Venetoclax | 400 mg | 400 mg | 400 mg | 400 mg |
| IMGN632 | 0 | 0 | 0 | 0 |
| Day | 17 | 18 | 19 | 20 |
| Aza | 0 | 0 | 0 | 0 |
| Venetoclax | 400 mg | 400 mg | 400 mg | 400 mg |
| IMGN632 | 0 | 0 | 0 | 0 |
| Day | 21 | 22 | 23 | 24 |
| Aza | 0 | 0 | 0 | 0 |
| Venetoclax | 400 mg | 400 mg | 400 mg | 400 mg |
| IMGN632 | 0 | 0 | 0 | 0 |
| Day | 25 | 26 | 27 | 28 |
| Aza | 0 | 0 | 0 | 0 |
| Venetoclax | 400 mg | 400 mg | 400 mg | 400 mg |
| IMGN632 | 0 | 0 | 0 | 0 |

IMGN632 Days 7, 10, and 14+Azacitidine+Venetoclax Dosing Schedule

| Day | 1 | 2 | 3 | 4 |
|---|---|---|---|---|
| Aza | 75 mg/m² | 75 mg/m² | 75 mg/m² | 75 mg/m² |
| Venetoclax | 100 mg (Cycle 1) 400 mg (Cycles ≥2) | 200 mg (Cycle 1) 400 mg (Cycles ≥2) | 400 mg | 400 mg |
| IMGN632 | 0 | 0 | 0 | 0 |
| Day | 5 | 6 | 7 | 8 |
| Aza | 75 mg/m² | 75 mg/m² | 75 mg/m² | 0 |
| Venetoclax | 400 mg | 400 mg | 400 mg | 400 mg |
| IMGN632 | 0 | 0 | 0.015, 0.03, or 0.06 mg/kg | 0 |
| Day | 9 | 10 | 11 | 12 |
| Aza | 0 | 0 | 0 | 0 |
| Venetoclax | 400 mg | 400 mg | 400 mg | 400 mg |
| IMGN632 | 0 | 0.015, 0.03, or 0.06 mg/kg | 0 | 0 |
| Day | 13 | 14 | 15 | 16 |
| Aza | 0 | 0 | 0 | 0 |
| Venetoclax | 400 mg | 400 mg | 400 mg | 400 mg |
| IMGN632 | 0 | 0.015, 0.03, or 0.06 mg/kg | 0 | 0 |
| Day | 17 | 18 | 19 | 20 |
| Aza | 0 | 0 | 0 | 0 |
| Venetoclax | 400 mg | 400 mg | 400 mg | 400 mg |
| IMGN632 | 0 | 0 | 0 | 0 |
| Day | 21 | 22 | 23 | 24 |
| Aza | 0 | 0 | 0 | 0 |
| Venetoclax | 400 mg | 400 mg | 400 mg | 400 mg |
| IMGN632 | 0 | 0 | 0 | 0 |
| Day | 25 | 26 | 27 | 28 |
| Aza | 0 | 0 | 0 | 0 |
| Venetoclax | 400 mg | 400 mg | 400 mg | 400 mg |
| IMGN632 | 0 | 0 | 0 | 0 |

Example 11

Administration of IMGN632 Human Patients with Minimal Residual Disease

A study of IMGN632 was designed to evaluate the effects of intravenous administration of IMGN632 in adult leukemia patients with minimal residual disease (MRD). The patients include both fit and unfit patients. Patients with MRD have less leukemic burden than other patients and therefore may have less CD123. Thus, there can be a higher IMGN632 to CD123 ratio in these patients than other patients, so that low doses (e.g., 15-45 mcg/kg) can be effective.

Patients enrolled in the study must be in complete remission (CR/CRi) and be MRD+ following intensive induction/consolidation therapy, with no appropriate standard of care therapy available. Central flow cytometry-based testing is used to assess MRD status.

Patients can receive a premedication regimen prior to each IMGN632 infusion. The premedication includes (i)

25-50 mg diphenhydramine (IV or per os [PO]); (ii) 325-650 mg acetaminophen or paracetamol (IV or PO) and/or (iii) 8 mg dexamethasone (PO or IV). If individual patients required more intensive or alternative treatment to prevent infusion reactions (e.g., a different corticosteroid, different dose of any agent), the regimen may be modified according to standard institutional practice.

IMGN632 is administered once every three weeks (21-days) at a dose of 0.015 mg/kg, 0.045 mg/kg, 0.09 mg/kg, 0.135 mg/kg, or 0.18 mg/kg.

The treatment consists of two cycles (i.e., a total of six weeks), wherein patients' second doses are administered at least 21 days after their first doses. Additional cycles, for example up to 10 or more total, can be administered for patients deriving benefit from this regimen.

Anti-leukemic activity is demonstrated by measuring the MRD+ to MRD− conversion rate. Relpase free survival (RFS) and event free survival (EFS) are also assessed to show anti-tumor activity.

Exemplary Instances Provided Herein

In one instance (I1) provided herein, a method for treating a hematologic malignancy in a subject comprises administering to said subject in need thereof an immunoconjugate that binds to CD123, wherein said immunoconjugate comprises an antibody or antigen-binding fragment thereof comprising a heavy chain variable region CDR1 comprising the amino acid sequence of SEQ ID NO: 5; a heavy chain variable region CDR2 comprising the amino acid sequence of SEQ ID NO: 6; and a heavy chain variable region CDR3 comprising the amino acid sequence of SEQ ID NO: 7; and a light chain variable region CDR1 comprising the amino acid sequence of SEQ ID NO: 8; a light chain variable region CDR2 comprising the amino acid sequence of SEQ ID NO: 9; and a light chain variable region CDR3 comprising the amino acid sequence of: SEQ ID NO: 10, and a BCL-2 inhibitor, a hypomethylating agent, or a combination thereof.

In one instance (I2) of I1 the immunoconjugate is administered in combination with the BCL-2 inhibitor. In one instance (I3) of I1, the immunoconjugate is administered in combination with the hypomethylating agent. In one instance (I4) of I1, the immunoconjugate is administered in combination with the BCL-2 inhibitor and the hypomethylating agent.

In one instance (I5) of any one of I1-I4, the antibody or antigen-binding fragment thereof comprises a VH comprising the amino acid sequence set forth in SEQ ID NO:1 and/or a VL comprising the amino acid sequence set forth in SEQ ID NO: 2. In one instance (I6) of I5, the antibody or antigen-binding fragment comprises a heavy chain constant region and/or a light chain constant region.

In one instance (I7) of any one of I1-I4, the antibody or antigen-binding fragment comprises a heavy chain comprising the amino acid sequence set forth in SEQ ID NO:3 and/or a light chain comprising the amino acid sequence set forth in SEQ ID NO:4.

In one instance (I8) of any one of I1-I7, the immunoconjugate comprises a cytotoxin, optionally wherein the cytotoxin is a DNA-alkylating agent. In one instance (I9) of any one of I8, the DNA-alkylating agent is indolino-benzodiazepine (IGN) DNA-alkylator.

In one instance (I10) of any one of I1-I9, the immunoconjugate comprises a peptide linker.

In one instance (I11) of any one of I1-I10, the immunoconjugate is IMGN632.

In one instance (I12) of any one of I1-I0, the immunoconjugate is administered in a pharmaceutical composition comprising immunoconjugates with the following structure:

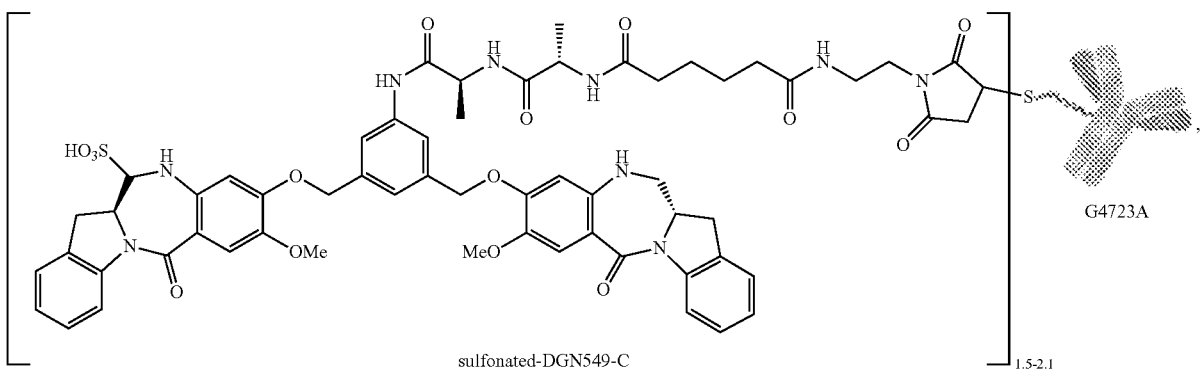

wherein
G4723A comprises a heavy chain comprising the amino acid sequence set forth in SEQ ID NO:3 and a light chain comprising the amino acid sequence set forth in SEQ ID NO:4.

In one instance (I13) of any one of I1-I12, the administration is a front-line therapy.

In one instance (I14) of any one of I1-I13, the immunoconjugate is administered intravenously.

In one instance (I5) of any one of I1-I14, administration of the immunoconjugate with the BCL-2 inhibitor, the hypomethylating agent, or a combination thereof produces a synergistic effect.

In one instance (I16) of any one of I1, I2, and I4-I15, administration of the immunoconjugate and the BCL-2 inhibitor does not produce more toxicity than administration of the immunoconjugate alone or the BCL-2 inhibitor alone. In one instance (I17) of any one of I1 and I3-I15, administration of the immunoconjugate and the hypomethylating agent does not produce more toxicity than administration of the immunoconjugate alone or the hypomethylating agent alone. In one instance (I18) of any one of I1 and I4-I15, administration of the immunoconjugate, the BCL-2 inhibitor, and the hypomethylating agent does not produce more toxicity than the administration of the immunoconjugate, the BCL-2 inhibitor, and/or the hypomethylating agent.

In one instance (I19) of any one of I1, I2, and I5-I18, the immunoconjugate is administered once in a 21-day cycle. In one instance (I20) of I19, the immunoconjugate is administered at a dose of about 0.015 mg/kg to about 0.09 mg/kg once in the 21-day cycle, optionally wherein the dose is about 0.015 mg/kg, about 0.045 mg/kg, or about 0.09 mg/kg.

In one instance (I21) of any one of I1-I18, the immunoconjugate is administered three times in a 21-day cycle. In one instance (I22) of I21, the total amount of immunoconjugate administered in the 21-day cycle is about 0.045 mg/kg, about 0.09 mg/kg, or about 0.18 mg/kg. In one instance (I23) of I22, about 0.015 mg/kg to about 0.06 mg/kg of the immunoconjugate is administered at each of the three times in the 21-day cycle, optionally wherein about 0.015 mg/kg, about 0.03 mg/kg, or about 0.06 mg/kg of the immunoconjugate is administered at each of the three times in the 21-day cycle. In one instance (I24) of any one of I21-I23, the first administration of the immunoconjugate is on day 7 of the 21-day cycle. In one instance (I25) of any one of I21-I24, the second administration of the immunoconjugate is on day 10 of the 21-day cycle. In one instance, (I26) of any one of I21-I25, the third administration of the immunoconjugate is on day 14 of the 21-day cycle. In one instance (I27) of any one of I21-I26, the first, second, and third administrations are on day 7, day 10, and day 14, respectively of the 21-day cycle.

In one instance (I28) of any one of I1, I2, and I4-I27, the BCL-2 inhibitor is venetoclax.

In one instance (I29) of any one of I1, I2, and I4-I28, the BCL-2 inhibitor is administered at a dose of 400 mg. In one instance (I30) of any one of I1, I2, and I4-I28, the BCL-2 inhibitor is administered at dose of 200 mg.

In one instance (I31) of any one of I1, I2, and I4-I30, the BCL-2 inhibitor is administered daily in a 21-day cycle. In one instance (I32) of any one of I1, I2, and I4-I28, the BCL-2 inhibitor is administered at a dose of 100 mg on day 1 of a 21-day cycle, at a dose of 200 mg on day 2 of the 21-day cycle, and at a dose of 400 mg on days 3-21 of the 21-day cycle. In one instance (I33) of any one of I1, I2, and I4-I28, the BCL-2 inhibitor is administered at a dose of 100 mg on day 1 of a 21-day cycle, at a dose of 200 mg on day 2 of the 21-day cycle, and a dose of 400 mg on days 3-7 or days 3-14 of the 21-day cycle. In one instance (I34) of any one of I1, I2, and I4-I28, the BCL-2 inhibitor is administered at a dose of 100 mg on day 1 of the 21-day cycle, and at a dose of 200 mg on days 2-21, 2-14, or 2-7 of the 21-day cycle.

In one instance (I35) of any one of I1, I2, and I4-I34, the BCL-2 inhibitor is administered orally.

In one instance (I36) of any one of I1, I2, and I4-I35, administration of the immunoconjugate is initiated six days after initiation of the administration of the BCL-2 inhibitor.

In one instance (I37) of any one of I1 and I3-I18, the immunoconjugate is administered once in a 28-day cycle. In one instance (I38) of I37, the immunoconjugate is administered at a dose of about 0.015 mg/kg to about 0.09 mg/kg once in the 28-day cycle, optionally wherein the dose is about 0.015 mg/kg, about 0.045 mg/kg, or about 0.09 mg/kg.

In one instance (I39) of any one of I1-I18, the immunoconjugate is administered three times in a 28-day cycle. In one instance (I40) of I39, the total amount of immunoconjugate administered in the 28-day cycle is about 0.045 mg/kg, about 0.09 mg/kg, or about 0.18 mg/kg. In one instance (I41) of I40, the about 0.015 mg/kg to about 0.06 mg/kg of the immunoconjugate is administered at each of the three times in the 28-day cycle, optionally wherein about 0.015 mg/kg, about 0.03 mg/kg, or about 0.06 mg/kg of the immunoconjugate is administered at each of the three times in the 28-day cycle. In one instance (I42) of any one of I39-I41, the first administration of the immunoconjugate is on day 7 of the 28-day cycle. In one instance (I43) of any one of I39-I42, the second administration of the immunoconjugate is on day 10 of the 28-day cycle. In one instance (I44) of any one of I39-I43, the third administration of the immunoconjugate is on day 14 of the 28-day cycle. In one instance (I45) of any one of I39-I44, the first, second, and third administrations are on day 7, day 10, and day 14, respectively of the 28-day cycle.

In one instance (I46) of any one of I37-I45, the BCL-2 inhibitor is venetoclax. In one instance (I47) of any one of I37-I46, the BCL-2 inhibitor is administered at a dose of 400 mg. In one instance (I48) of any one of I37-I46, the BCL-2 inhibitor is administered at dose of 200 mg. In one instance (I49) of any one of I37-I48, the the BCL-2 inhibitor is administered daily in a 28-day cycle. In one instance (I50) of any one of I37-I46, the BCL-2 inhibitor is administered at a dose of 100 mg on day 1 of a 28-day cycle, at a dose of 200 mg on day 2 of the 28-day cycle, and at a dose of 400 mg on days 3-28 of the 28-day cycle. In one instance (I51) of any one of I37-I46, the BCL-2 inhibitor is administered at a dose of 100 mg on day 1 of a 28-day cycle, at a dose of 200 mg on day 2 of the 28-day cycle, and a dose of 400 mg on days 3-7 or days 3-14 of the 28-day cycle. In one instance (I52) of any one of I37-I46, the BCL-2 inhibitor is administered at a dose of 100 mg on day 1 of the 28-day cycle, and at a dose of 200 mg on days 2-28, 2-14, or 2-7 of the 28-day cycle. In one instance (I53) of any one of I37-I52, the BCL-2 inhibitor is administered orally. In one instance (I54) of any one of I37-I53, administration of the immunoconjugate is initiated six days after initiation of the administration of the BCL-2 inhibitor.

In one instance (I55) of any one of I1, I3-I18, and I37-I54, the hypomethylating agent is azacitidine. In one instance (I56) of I55, the azacitidine is administered in a 28-day cycle. In one instance (I57) of I55 or I56, the azacitidine is administered once daily on days 1-7 of a 28-day cycle. In one instance (I58) of I55 or I56, the azacitidine is administered once daily on days 3-7 of a 28-day cycle. In one instance (I59) of any one of I56-I58, the azacitidine is administered at a dose of about 75 mg/m$^2$. In one instance (I60) of any one of I56-I59, the azacitidine is administered subcutaneously or intravenously.

In one instance (I61) of any one of I1 and I3-I54, the hypomethylating agent is decitabine.

In one instance (I62) of I61, the decitabine is administered intravenously.

In one instance (I63) of any one of I1-I62, the hematological malignancy is present in the subject as minimal residual disease (MRD).

In one instance (I64), a method for treating a hematologic malignancy present as a minimal residual disease in a human subject comprises administering to the subject an anti-CD123 immunoconjugate comprising an anti-CD123 antibody or antigen-binding fragment thereof linked to a cytotoxic agent. In one instance (I65) of I64, the immunoconjugate is administered at a dose of about 0.045 mg/kg to about 0.18 mg/kg. In one instance (I66) of I64 or I65, about 0.045 mg/kg, about 0.09 mg/kg, about 0.135 mg/kg, or about 0.18 mg/kg is administered to the subject. In one instance (I67) of any one of I64-I66, the immunoconjugate is administered intravenously. In one instance (I68) of any one of I64-I67, the hematologic malignancy is a leukemia. In one instance (I69) of any one of I64-I68, the immunoconjugate is administered to the subject once in a 21-day cycle.

In one instance (I70) of any one of I20-I63 or I69, the administration is for one cycle. In one instance (I71) of any one of I20-I63 or I69, the administration is for more than one cycle. In one instance (I72) of any one of I20-I63 or I69, the administration is for at least 2 cycles, at least 3 cycles, at least 4 cycles, at least 5 cycles, at least 6 cycles, at least 7 cycles, at least 8 cycles, at least 9 cycles, or at least 10 cycles. In one instance (I73) of any one of I20-I63 or I69, the administration is for about 2-4 cycles, about 2-6 cycles, about 2-8 cycles, about 2-10 cycles, or about 2-12 cycles.

In one instance (I74) of any one of I1-I73, method further comprises administering a reduced dose of the immunoconjugate after a dose-limiting toxicity has occurred in the subject and has been reduced to baseline or ≤Grade 2.

In one instance (I75) of any one of I1-I73, the immunoconjugate is further administered as a maintenance therapy. In one instance (I76) of I75, the maintenance therapy comprises administering the immunoconjugate once in a 21-day cycle. In one instance (I77) of I76, the maintenance therapy comprises administering the immunoconjugate at a dose of about 0.015 mg/kg to about 0.09 mg/kg once in the 21-day cycle, optionally wherein the dose is about 0.015 mg/kg, about 0.045 mg/kg, or about 0.09 mg/kg. In one instance (I78) of I75, the maintenance therapy comprises administering the immunoconjugate three times in a 21-day cycle. In one instance (I79) of I78, during the maintenance therapy, the total amount of immunoconjugate administered in the 21-day cycle is about 0.045 mg/kg, about 0.09 mg/kg, or about 0.18 mg/kg. In one instance (I80) of I79, during the maintenance therapy about 0.015 mg/kg to about 0.06 mg/kg of the immunoconjugate is administered at each of the three times in the 21-day cycle, optionally wherein about 0.015 mg/kg, about 0.03 mg/kg, or about 0.06 mg/kg of the immunoconjugate is administered at each of the three times in the 21-day cycle. In one instance (I81) of any one of I78-I80, during the maintenance therapy, the first, second, and third administrations are on day 1, day 4, and day 8, respectively of the 21-day cycle.

In one instance (I82) of any one of I1-I12, I14-I62, and I69-I81, the hematological malignancy is a relapsed hematological malignancy.

In one instance (I83) of any one of I1-I82, the hematological malignancy is acute myeloid leukemia (AML), myelodysplastic syndrome (MDS), B-cell acute lymphoblastic leukemia (B-ALL), chronic myeloid leukemia in blast crisis/phase (BP-CML), and blastic plasmacytoid dendritic cell neoplasm (BPDCN).

In one instance (I84) of any one of I1-I82, the hematological malignancy is AML. In one instance (I85) of I84, the AML is relapsed AML. In one instance (I86) of I84 or I85, the AML is refractory AML.

In one instance (I87) of any one of I1-I82, the hematological malignancy is BPDCN. In one instance (I88) of I88, the BPDCN is relapsed BPDCN. In one instance (I89) of I87 or I88, the BPDCN is refractory BPDCN.

In one instance (I90) of any one of I1-I82, the hematological malignancy is ALL. In one instance (I91) of I90, the ALL is relapsed ALL. In one instance (I92) of I90 or I91, the ALL is refractory ALL.

In one instance (I93) of any one of I1-I82 the hematological malignancy is chronic myelomonocytic leukemia (CMML). In one instance (I94) of I93, the CMML is relapsed CMML. In one instance (I95) of I93 or I94, the CMML is refractory CMML.

In one instance (I96) of any one of I1-I82, the hematological malignancy is myelofibrosis (MF). In one instance (I97) of I96, the MF is relapsed MF. In one instance (I98) of I96 or I97, the MF is refractory MF.

In one instance (I99) of any one of I1-I82, the hematological malignancy is myelodysplastic syndrome (MDS). In one instance (I100) of I99, the MDS is relapsed MDS. In one instance (I101) of I99 or I100, the MDS is refractory MDS.

In one instance (I102) of any one of I1-I101, the hematological malignancy is a CD123-expressing hematological malignancy.

In one instance (I103) of any one of I1-I102, CD123 has been detected in a sample obtained from the hematological malignancy prior to the administration. In one instance (I104) of I103, the CD123 was detected using flow cytometry.

In one instance (I105) of any one of I1-I105, the method further comprises detecting CD123 in a sample obtained from the hematological malignancy prior to the administration.

In one instance (I106) of any one of I1-I105, at least 80% of cells in the hematological malignancy express CD123. In one instance (I107) of any one of I1-I106, CD123 has been detected in at least 80% of cells in a sample obtained from the hematological malignancy prior to the administration.

In one instance (I108) of any one of I1-I107, the method further comprises detecting CD123 in at least 80% of cells in a sample obtained from the hematological malignancy prior to the administration.

In one instance (I109) of any one of I1-I63 and I69-I108, the hematological malignancy is resistant to IMGN632.

In one instance (I1110) of any one of I1-I109, the hematological malignancy expresses multidrug resistance 1 (MDR1). In one instance (I111) of any one of I1-I110, the hematological malignancy expresses P-glycoprotein (P-gp). In one instance (I112) of any one of I14111, the subject has an absolute neutrophil count of greater than 500 neutrophils/µL.

In one instance (I113) of any one of I1-I12 and I14-I112, the subject received at least one prior line of therapy. In one instance (I114) of any one of I1-I12 and I14-I112 the subject received at least two prior lines of therapy. In one instance (I115) of any one of I1-I12 and I14-I112, the subject received at least three prior lines of therapy.

In one instance (I116) of any one of I1-I12 and I14-I115, the cancer has previously been treated with venetoclax. In one instance (I117) of any one of I1-I115, the cancer has not previously been treated with venetoclax.

In one instance (I118) of any one of I1-I12 and I14-I117, the cancer has previously been treated with a hyomethylating agent. In one instance (I119) of any one of I1-I117, the cancer has not previously been treated with a hypomethylating agent.

In one instance (I120) of any one of I1-I119, the subject has been pretreated with a corticosteroid prior to administration of the immunoconjugate. In one instance (I121) of any one of I1-I119, the method further comprises pretreating the subject with a corticosteroid prior to administration of the immunoconjugate. In one instance (I122) of I120 or I121, the corticosteroid is diphenhydramine, acetaminophen, paracetamol, dexamethasone, or a combination thereof.

In one instance (I123) of any one of I1-I63 and I69-I122, the immunoconjugate and the BCL-2 inhibitor, the hypomethylating agent, or combination thereof are administered in separate pharmaceutical compositions.

In one instance (I124) of any one of I1-I123, the subject is human.

In one instance (I125), a method for treating a hematologic malignancy in a human subject comprises administering to said subject in need thereof IMGN632 and venetoclax in a 21-day cycle, wherein the IMGN632 is administered intravenously on day 7 of the cycle at a dose of about 0.015 mg/kg to about 0.09 mg/kg, optionally wherein the dose is about 0.015 mg/kg, about 0.045 mg/kg, or about 0.09 mg/kg, and wherein the venetoclax is administered orally at a dose of 100 mg on day 1 of the cycle, at a dose of 200 mg on day 2 of the cycle, and at a dose of 400 mg on days 3-21 of the cycle.

In one instance (I126), a method for treating a hematologic malignancy in a human subject comprises administering to said subject in need thereof IMGN632 and venetoclax in a 21-day cycle, wherein the IMGN632 is administered intravenously on day 7 of the cycle at a dose of about 0.015 mg/kg to about 0.09 mg/kg, optionally wherein the dose is about 0.015 mg/kg, about 0.045 mg/kg, or about 0.09 mg/kg, and wherein the venetoclax is administered at an oral daily dose of 400 mg.

In one instance (I127), a method for treating a hematologic malignancy in a human subject comprises administering to said subject in need thereof IMGN632 and venetoclax in a 21-day cycle, wherein a dose of about 0.015 mg/kg to about 0.06 mg/kg of the IMGN632 is administered intravenously on each of days 7, 10, and 14 of the cycle at, optionally wherein about 0.015 mg/kg, about 0.03 mg/kg, or about 0.06 mg/kg is administered on each of the days, and wherein the venetoclax is administered orally at a dose of 100 mg on day 1 of the cycle, at a dose of 200 mg on day 2 of the cycle, and at a dose of 400 mg on days 3-21 of the cycle.

In one instance (I128), a method for treating a hematologic malignancy in a human subject comprises administering to said subject in need thereof IMGN632 and venetoclax in a 21-day cycle, wherein a dose of about 0.015 mg/kg to about 0.06 mg/kg of the IMGN632 is administered intravenously on each of days 7, 10, and 14 of the cycle at, optionally wherein about 0.015 mg/kg, about 0.03 mg/kg, or about 0.06 mg/kg is administered on each of the days, and wherein the venetoclax is administered at an oral daily dose of 400 mg.

In one instance (I129), a method for treating a hematologic malignancy in a human subject comprises administering to said subject in need thereof IMGN632 and azacitidine in a 28-day cycle wherein the IMGN632 is administered intravenously on day 7 of the cycle at a dose of about 0.015 mg/kg to about 0.09 mg/kg, optionally wherein the dose is about 0.015 mg/kg, about 0.045 mg/kg, or about 0.09 mg/kg, and wherein the azacitdine is administered subcutaneously or intravenously at a dose of 75 mg/m$^2$ on days 1-7 of the cycle.

In one instance (I130), a method for treating a hematologic malignancy in a human subject comprises administering to said subject in need thereof IMGN632 and azacitidine in a 28-day cycle wherein about 0.015 mg/kg to about 0.06 mg/kg of the IMGN632 is administered intravenously on each of days 7, 10, and 14 of the cycle at a dose of, optionally wherein about 0.015 mg/kg, about 0.03 mg/kg, or about 0.06 mg/kg is administered on each of the days, and wherein the azacitdine is administered subcutaneously or intravenously at a dose of 75 mg/m$^2$ on days 1-7 of the cycle.

In one instance (I131) of I129 or I130, the method further comprises administering venetoclax orally at a dose of 100 mg on day 1 of the cycle, at a dose of 200 mg on day 2 of the cycle, and at a dose of 400 mg on days 3-28 of the cycle In one instance (I132) of I129 or I130, the method further comprises administering venetoclax at an oral daily dose of 400 mg.

In one instance (I133) of any one of I125-I132, the hematologic malignancy is AML. In one instance (I134) of any one of I125-I132, the hematologic malignancy is BPDCN. In one instance (I135) of any one of I125-I132, the hematologic malignancy is chronic myelomonocytic leukemia (CMML). In one instance (I136) of any one of I125-I132, the hematologic malignancy is myelofibrosis (MF). In one instance (I137) of any one of I125-I132, the hematologic malignancy is myelodysplastic syndrome (MDS).

It is to be appreciated that the Detailed Description section, and not the Summary and Abstract sections, is intended to be used to interpret the claims. The Summary and Abstract sections sets forth one or more, but not all, exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method for treating a hematologic malignancy in a subject comprising administering to said subject in need thereof an immunoconjugate that binds to CD123 and venetoclax, wherein the immunoconjugate comprises an antibody or antigen-binding fragment linked to a cytotoxin and wherein the antibody or antigen-binding fragment thereof comprises a heavy chain variable region CDR1 comprising the amino acid sequence of SEQ ID NO: 5; a heavy chain variable region CDR2 comprising the amino acid sequence of SEQ ID NO: 6; and a heavy chain variable region CDR3 comprising the amino acid sequence of SEQ ID NO: 7; and a light chain variable region CDR1 comprising the amino acid sequence of SEQ ID NO: 8; a light chain variable region CDR2 comprising the amino acid sequence of SEQ ID NO: 9; and a light chain variable region CDR3 comprising the amino acid sequence of: SEQ ID NO: 10, wherein the cytotoxin is a DNA-alkylating agent, and wherein the hematological malignancy is relapsed and/or refractory acute myeloid leukemia (AML).

2. A method for treating a hematologic malignancy in a subject comprising administering to said subject in need thereof an immunoconjugate that binds to CD123 and azacitidine, wherein the immunoconjugate comprises an antibody or antigen-binding fragment linked to a cytotoxin and wherein the antibody or antigen-binding fragment thereof comprises a heavy chain variable region CDR1 comprising the amino acid sequence of SEQ ID NO: 5; a heavy chain variable region CDR2 comprising the amino acid sequence of SEQ ID NO: 6; and a heavy chain variable region CDR3 comprising the amino acid sequence of SEQ ID NO: 7; and a light chain variable region CDR1 comprising the amino acid sequence of SEQ ID NO: 8; a light chain variable region CDR2 comprising the amino acid sequence of SEQ ID NO: 9; and a light chain variable region CDR3 comprising the amino acid sequence of: SEQ ID NO: 10, wherein the cytotoxin is a DNA-alkylating agent, and wherein the hematological malignancy is relapsed and/or refractory acute myeloid leukemia (AML).

3. A method for treating a hematologic malignancy in a subject comprising administering to said subject in need thereof an immunoconjugate that binds to CD123, venetoclax, and azacitidine, wherein the immunoconjugate comprises an antibody or antigen-binding fragment linked to a cytotoxin and wherein the antibody or antigen-binding fragment thereof comprises a heavy chain variable region CDR1 comprising the amino acid sequence of SEQ ID NO: 5; a heavy chain variable region CDR2 comprising the amino acid sequence of SEQ ID NO: 6; and a heavy chain variable region CDR3 comprising the amino acid sequence of SEQ ID NO: 7; and a light chain variable region CDR1 comprising the amino acid sequence of SEQ ID NO: 8; a light chain variable region CDR2 comprising the amino acid sequence of SEQ ID NO: 9; and a light chain variable region CDR3 comprising the amino acid sequence of: SEQ ID NO: 10, wherein the cytotoxin is a DNA-alkylating agent, and wherein the hematological malignancy is relapsed and/or refractory acute myeloid leukemia (AML).

4. The method of claim 3, wherein the antibody or antigen-binding fragment thereof comprises a VH comprising the amino acid sequence set forth in SEQ ID NO:1 and/or a VL comprising the amino acid sequence set forth in SEQ ID NO: 2.

5. The method of claim 3, wherein the DNA-alkylating agent is indolino-benzodiazepine (IGN) DNA-alkylator.

6. The method of claim 3, wherein the immunoconjugate is administered in a pharmaceutical composition comprising immunoconjugates with the following structure:

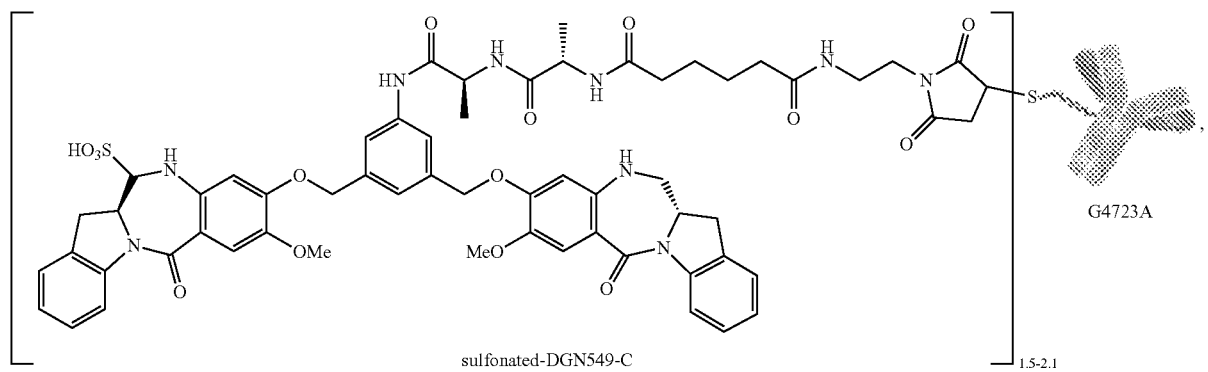

wherein G4723A comprises a heavy chain comprising the amino acid sequence set forth in SEQ ID NO:3 and a light chain comprising the amino acid sequence set forth in SEQ ID NO:4.

7. The method of claim 3, wherein the immunoconjugate is administered once in a 21-day cycle.

8. The method of claim 3, wherein the immunoconjugate is administered once in a 28-day cycle.

9. The method of claim 8, wherein the immunoconjugate is administered at a dose of about 0.015 mg/kg.

10. The method of claim 8, wherein the immunoconjugate is administered at a dose of about 0.045 mg/kg once in the 28-day cycle.

11. The method of claim 3, wherein the venetoclax the is administered at a dose of 400 mg on days 1-8 of a 28-day cycle.

12. The method of claim 3, wherein the azacitidine is administered in a 28-day cycle.

13. The method of claim 3, wherein the hematological malignancy is present in the subject as minimal residual disease (MRD).

14. The method of claim 3, wherein the immunoconjugate is further administered as a maintenance therapy.

15. The method of claim 3, wherein the hematological malignancy expresses CD123.

16. The method of claim 3, wherein the hematological malignancy is resistant to IMGN632.

17. The method of claim 3, wherein the hematological malignancy expresses multidrug resistance 1 (MDR1) and/or expresses P-glycoprotein (P-gp).

18. The method of claim 3, wherein the subject has an absolute neutrophil count of greater than 500 neutrophils/μL.

19. The method of claim 3, wherein the cancer has previously been treated with venetoclax.

20. The method of claim 3, wherein the cancer has previously been treated with a hyomethylating agent.

21. The method of claim 3, wherein the immunoconjugate, venetoclax, and azacitidine are administered in separate pharmaceutical compositions.

22. The method of claim 3, wherein the subject is human.

23. A method for treating a hematologic malignancy in a human subject comprising administering to said subject in need thereof IMGN632 and venetoclax in a 21-day cycle, wherein the IMGN632 is administered intravenously on day 7 of the cycle at a dose of about 0.015 mg/kg to about 0.09 mg/kg, and wherein the venetoclax is administered at an oral daily dose of 400 mg, and wherein the hematological malignancy is relapsed and/or refractory acute myeloid leukemia (AML).

24. A method for treating a hematologic malignancy in a human subject comprising administering to said subject in need thereof IMGN632 and azacitidine in a 28-day cycle wherein the IMGN632 is administered intravenously on day 7 of the cycle at a dose of about 0.015 mg/kg to about 0.09 mg/kg, and wherein the azacitidine is administered subcutaneously or intravenously at a dose of 75 mg/m², and wherein the hematological malignancy is relapsed and/or refractory acute myeloid leukemia (AML).

25. The method of claim 3, wherein the immunoconjugate is administered in a pharmaceutical composition comprising immunoconjugates with the following structure:

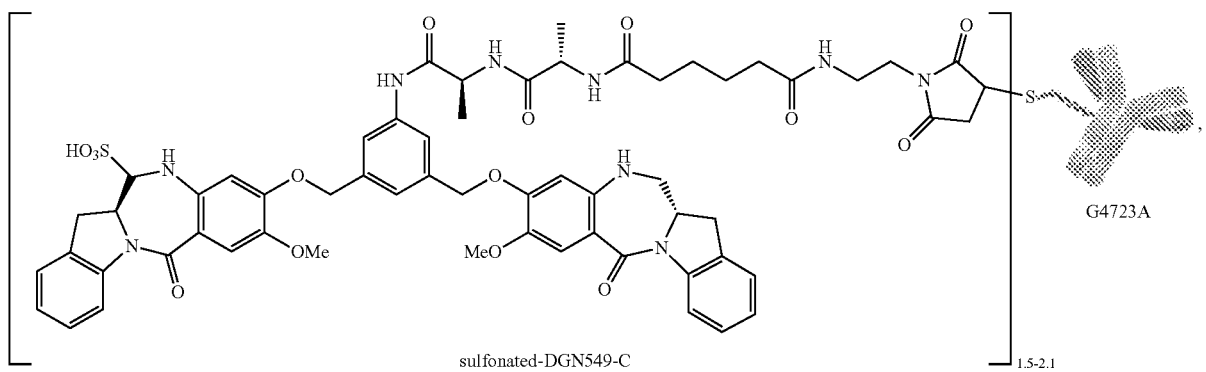

sulfonated-DGN549-C     G4723A     1.5-2.1 wherein G4723A comprises a heavy chain comprising the amino acid sequence set forth in SEQ ID NO:3 and a light chain comprising the amino acid sequence set forth in SEQ ID NO:4, wherein the immunoconjugate, venetoclax, and azacitidine are administered in a 28-day cycle, wherein the immunoconjugate is administered intravenously on day 7 of the cycle at a dose of 0.045 mg/kg, wherein the venetoclax is orally administered on days 1-14 of the cycle, and wherein the azacitidine is administered subcutaneously or intravenously on days 1-7 of the cycle.

26. The method of claim 3, wherein the immunoconjugate is administered in a pharmaceutical composition comprising immunoconjugates with the following structure:

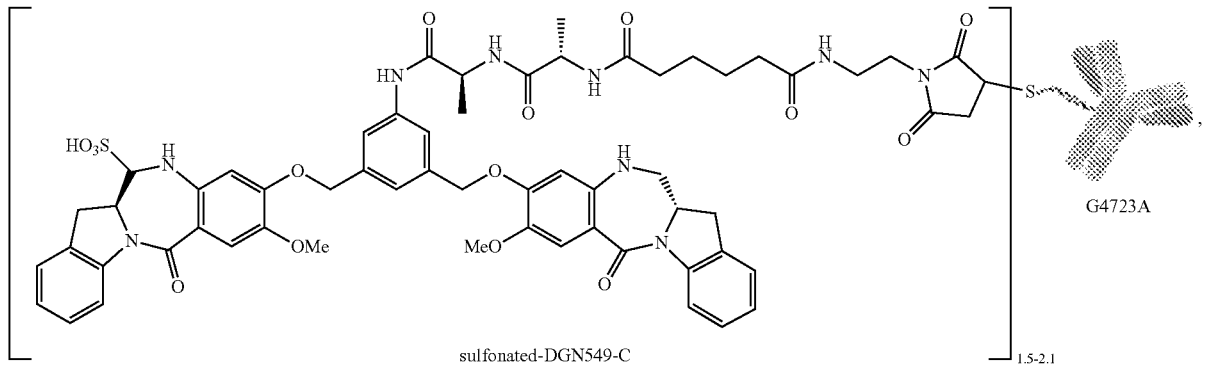

sulfonated-DGN549-C     G4723A     1.5-2.1 wherein G4723A comprises a heavy chain comprising the amino acid sequence set forth in SEQ ID NO:3 and a light chain comprising the amino acid sequence set forth in SEQ ID NO:4, wherein the immunoconjugate, venetoclax, and azacitidine are administered in a 28-day cycle, wherein the immunoconjugate is administered intravenously on day 7 of the cycle at a dose of 0.045 mg/kg, wherein the venetoclax is orally administered on days 1-14 of the cycle, and wherein the azacitidine is administered subcutaneously or intravenously at a dose of 75 mg/m² on days 1-7 of the cycle.

27. The method of claim 25, wherein the venetoclax is administered at a dose of 100 mg on days 1-14 of the cycle.

28. The method of claim 25, wherein the venetoclax is administered at a dose of 200 mg on days 1-14 of the cycle.

29. The method of claim 25, wherein the venetoclax is administered at a dose of 400 mg on days 1-14 of the cycle.

30. The method of claim 26, wherein the venetoclax is administered at a dose of 100 mg on days 1-14 of the cycle.

31. The method of claim 26, wherein the venetoclax is administered at a dose of 200 mg on days 1-14 of the cycle.

32. The method of claim 26, wherein the venetoclax is administered at a dose of 400 mg on days 1-14 of the cycle.

33. The method of claim 3, wherein the subject received at least two prior lines of therapy.

34. The method of claim 3, wherein the subject received at least three prior lines of therapy.

35. The method of claim 3, wherein the relapsed and/or refractory AML, has an FLT3-ITD mutation.

36. The method of claim 25, wherein the subject is pretreated with a corticosteroid.

37. The method of claim 36, wherein the corticosteroid is selected from the group consisting of prednisone, prednisolone, methylprednisolone, beclamethasone, betamethasone, dexamethasone, fludrocortisone, hydrocortisone, and triamcinolone.

38. The method of claim 26, wherein the subject is pretreated with a corticosteroid.

39. The method of claim 38, wherein the corticosteroid is selected from the group consisting of prednisone, prednisolone, methylprednisolone, beclamethasone, betamethasone, dexamethasone, fludrocortisone, hydrocortisone, and triamcinolone.

40. The method of claim 3, wherein the cancer has not previously been treated with venetoclax.

* * * * *

UNITED STATES PATENT AND TRADEMARK OFFICE
CERTIFICATE OF CORRECTION

PATENT NO. : 11,701,428 B2
APPLICATION NO. : 16/862358
DATED : July 18, 2023
INVENTOR(S) : Sharlene Adams, Callum M. Sloss and Patrick Zweidler-McKay Page 1 of 2

It is certified that error appears in the above-identified patent and that said Letters Patent is hereby corrected as shown below:

In the Specification

In Column 1, Line 10, change "entirety" to "entirety."
In Column 1, Line 49, change "CD" to "CD123"
In Column 3, Line 66, change "the the" to "the"
In Column 7, Line 7, change "cycle" to "cycle."
In Column 7, Line 31, change "refactory" to "refractory"
In Column 8, Line 21, change "hyomethylating" to "hypomethylating"
In Column 9, Line 8, change "veneoclax" to "venetoclax"
In Column 9, Line 9, change "veneoclax" to "venetoclax"
In Column 9, Line 11, change "veneoclax" to "venetoclax"
In Column 9, Line 12, change "veneoclax" to "venetoclax"
In Column 9, Line 14, change "veneoclax" to "venetoclax"
In Column 9, Line 54, change "azacitdine" to "azacitidine"
In Column 9, Line 64, change "azacitdine" to "azacitidine"
In Column 9, Line 66, change "azacitdine" to "azacitidine"
In Column 9, Line 67, change "azacitdine" to "azacitidine"
In Column 10, Line 11, change "azacitdine" to "azacitidine"
In Column 10, Line 21, change "azacitdine" to "azacitidine"
In Column 10, Lines 29-30, change "azacitdine" to "azacitidine"
In Column 10, Line 31, change "azacitdine" to "azacitidine"
In Column 10, Lines 32-33, change "azacitdine" to "azacitidine"
In Column 10, Line 38, change "veneoclax" to "venetoclax"
In Column 10, Line 40, change "veneoclax" to "venetoclax"
In Column 10, Line 41, change "veneoclax" to "venetoclax"
In Column 10, Line 43, change "veneoclax" to "venetoclax"
In Column 10, Line 44, change "veneoclax" to "venetoclax"
In Column 10, Line 46, change "veneoclax" to "venetoclax"
In Column 10, Line 67, change "bisulfate." to "bisulfite."
In Column 12, Line 31, change "azacitidne" to "azacitidine"

Signed and Sealed this
Twenty-sixth Day of December, 2023

Katherine Kelly Vidal
*Director of the United States Patent and Trademark Office*

CERTIFICATE OF CORRECTION (continued)
U.S. Pat. No. 11,701,428 B2

In Column 12, Line 33, change "azacitidne" to "azacitidine"
In Column 12, Line 39, change "azacitidne" to "azacitidine"
In Column 12, Line 40, change "azacitidne" to "azacitidine"
In Column 12, Lines 43-44, change "azacitidne" to "azacitidine"
In Column 12, Line 45, change "azacitidne" to "azacitidine"
In Column 30, Line 24, change "indolino-benzodiazepene" to "indolino-benzodiazepine"
In Column 31, Line 3, change "Azacitine" to "Azacitidine"
In Column 31, Line 5, change "subcutenous" to "subcutaneous"
In Column 31, Line 15, change "lypophilized" to "lyophilized"
In Column 32, Line 54, change "Lippencott" to "Lippincott"
In Column 34, Line 12, change "(e.g," to "(e.g.,"
In Column 34, Line 16, change "(e.g," to "(e.g.,"
In Column 34, Line 64, change "(e.g," to "(e.g.,"
In Column 35, Line 13, change "(e.g," to "(e.g.,"
In Column 38, Line 66, change "ventoclax)" to "venetoclax)"
In Column 42, Line 34, change "and and" to "and"
In Column 47, Line 35, change "beclamethasone," to "beclomethasone,"
In Column 50, Line 2, change "(FIG." to "(FIGS."
In Column 53, Line 20, change "he" to "the"
In Column 65, Line 40, change "/refactory" to "/refractory"
In Column 65, Line 40, change "relapsted/" to "relapsed/"
In Column 65, Line 48, change "azacitdine" to "azacitidine"
In Column 67, Line 37, change "Ventoclax" to "Venetoclax"
In Column 68, Line 16, change "Venetoclas" to "Venetoclax"
In Column 68, Line 54, change "ventoclax" to "venetoclax"
In Column 69, Line 5, change "azacitdine" to "azacitidine"
In Column 71, Line 17, change "Relpase" to "Relapse"
In Column 72, Line 21, change "-I0," to "I10,"
In Column 74, Line 18, change "the the" to "the"
In Column 74, Line 19, change "(ISO)" to "(I50)"
In Column 76, Line 33, change "(I1110)" to "(I110)"
In Column 76, Lines 51-52, change "hyomethylating" to "hypomethylating"
In Column 77, Line 53, change "azacitdine" to "azacitidine"
In Column 78, Line 6, change "azacitdine" to "azacitidine"

In the Claims

In Claim 11, Column 91, Line 40, change "the is" to "is"
In Claim 20, Column 92, Line 26, change "hyomethylating" to "hypomethylating"
In Claim 35, Column 94, Line 30, change "AML," to "AML"
In Claim 37, Column 94, Line 53, change "beclamethasone," to "beclomethasone,"
In Claim 39, Column 94, Line 61, change "beclamethasone," to "beclomethasone,"

SEQUENCE LISTING

<160> NUMBER OF SEQ ID NOS: 12

<210> SEQ ID NO 1
<211> LENGTH: 121
<212> TYPE: PRT

-continued

<213> ORGANISM: Artificial Sequence
<220> FEATURE:
<223> OTHER INFORMATION: huCD123-6Gv7 Heavy Chain Variable Region

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120

<210> SEQ ID NO 2
<211> LENGTH: 108
<212> TYPE: PRT
<213> ORGANISM: Artificial Sequence
<220> FEATURE:
<223> OTHER INFORMATION: huCD123-6Gv4 Light Chain Variable Region

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys Arg
            100                 105

<210> SEQ ID NO 3
<211> LENGTH: 450
<212> TYPE: PRT
<213> ORGANISM: Artificial Sequence
<220> FEATURE:
<223> OTHER INFORMATION: huCD123-6Gv7-C442 Full Length Heavy Chain

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

```
Gly Tyr Ile Lys Pro Tyr Asn Asp Gly Thr Lys Tyr Asn Glu Lys Phe
     50                  55                  60

Lys Gly Arg Ala Thr Leu Thr Ser Asp Arg Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Gly Gly Asn Asp Tyr Tyr Asp Thr Met Asp Tyr Trp Gly
                100                 105                 110

Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Cys Leu Ser
                435                 440                 445

Pro Gly
    450
```

<210> SEQ ID NO 4
<211> LENGTH: 214
<212> TYPE: PRT
<213> ORGANISM: Artificial Sequence
<220> FEATURE:
<223> OTHER INFORMATION: huCD123-6Gv4 Full Length Light Chain

<400> SEQUENCE: 4

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 5
<211> LENGTH: 5
<212> TYPE: PRT
<213> ORGANISM: Artificial Sequence
<220> FEATURE:
<223> OTHER INFORMATION: huCD123-6Gv7 Variable Heavy Chain CDR1

<400> SEQUENCE: 5

```
Ser Ser Ile Met His
1               5
```

<210> SEQ ID NO 6
<211> LENGTH: 17
<212> TYPE: PRT
<213> ORGANISM: Artificial Sequence
<220> FEATURE:
<223> OTHER INFORMATION: huCD123-6Gv7 Variable Heavy Chain CDR2

<400> SEQUENCE: 6

```
Tyr Ile Lys Pro Tyr Asn Asp Gly Thr Lys Tyr Asn Glu Lys Phe Lys
1               5                   10                  15

Gly
```

<210> SEQ ID NO 7
<211> LENGTH: 12
<212> TYPE: PRT
<213> ORGANISM: Artificial Sequence
<220> FEATURE:
<223> OTHER INFORMATION: huCD123-6Gv7 Variable Heavy Chain CDR3

<400> SEQUENCE: 7

Glu Gly Gly Asn Asp Tyr Tyr Asp Thr Met Asp Tyr
 1               5                  10

<210> SEQ ID NO 8
<211> LENGTH: 11
<212> TYPE: PRT
<213> ORGANISM: Artificial Sequence
<220> FEATURE:
<223> OTHER INFORMATION: huCD123-6Gv4 Variable Light Chain CDR1

<400> SEQUENCE: 8

Arg Ala Ser Gln Asp Ile Asn Ser Tyr Leu Ser
 1               5                  10

<210> SEQ ID NO 9
<211> LENGTH: 7
<212> TYPE: PRT
<213> ORGANISM: Artificial Sequence
<220> FEATURE:
<223> OTHER INFORMATION: huCD123-6Gv4 Variable Light Chain CDR2

<400> SEQUENCE: 9

Arg Val Asn Arg Leu Val Asp
 1               5

<210> SEQ ID NO 10
<211> LENGTH: 9
<212> TYPE: PRT
<213> ORGANISM: Artificial Sequence
<220> FEATURE:
<223> OTHER INFORMATION: huCD123-6Gv4 Variable Light Chain CDR3

<400> SEQUENCE: 10

Leu Gln Tyr Asp Ala Phe Pro Tyr Thr
 1               5

<210> SEQ ID NO 11
<211> LENGTH: 378
<212> TYPE: PRT
<213> ORGANISM: Homo sapiens

<400> SEQUENCE: 11

Met Val Leu Leu Trp Leu Thr Leu Leu Ile Ala Leu Pro Cys Leu
 1               5                  10                  15

Leu Gln Thr Lys Glu Asp Pro Asn Pro Ile Thr Asn Leu Arg Met
                20                  25                  30

Lys Ala Lys Ala Gln Gln Leu Thr Trp Asp Leu Asn Arg Asn Val Thr
                35                  40                  45

Asp Ile Glu Cys Val Lys Asp Ala Asp Tyr Ser Met Pro Ala Val Asn
    50                  55                  60

Asn Ser Tyr Cys Gln Phe Gly Ala Ile Ser Leu Cys Glu Val Thr Asn
 65                  70                  75                  80

Tyr Thr Val Arg Val Ala Asn Pro Pro Phe Ser Thr Trp Ile Leu Phe
                85                  90                  95

```
Pro Glu Asn Ser Gly Lys Pro Trp Ala Gly Ala Glu Asn Leu Thr Cys
            100                 105                 110

Trp Ile His Asp Val Asp Phe Leu Ser Cys Ser Trp Ala Val Gly Pro
        115                 120                 125

Gly Ala Pro Ala Asp Val Gln Tyr Asp Leu Tyr Leu Asn Val Ala Asn
    130                 135                 140

Arg Arg Gln Gln Tyr Glu Cys Leu His Tyr Lys Thr Asp Ala Gln Gly
145                 150                 155                 160

Thr Arg Ile Gly Cys Arg Phe Asp Asp Ile Ser Arg Leu Ser Ser Gly
                165                 170                 175

Ser Gln Ser Ser His Ile Leu Val Arg Gly Arg Ser Ala Ala Phe Gly
            180                 185                 190

Ile Pro Cys Thr Asp Lys Phe Val Val Phe Ser Gln Ile Glu Ile Leu
        195                 200                 205

Thr Pro Pro Asn Met Thr Ala Lys Cys Asn Lys Thr His Ser Phe Met
    210                 215                 220

His Trp Lys Met Arg Ser His Phe Asn Arg Lys Phe Arg Tyr Glu Leu
225                 230                 235                 240

Gln Ile Gln Lys Arg Met Gln Pro Val Ile Thr Glu Gln Val Arg Asp
                245                 250                 255

Arg Thr Ser Phe Gln Leu Leu Asn Pro Gly Thr Tyr Thr Val Gln Ile
            260                 265                 270

Arg Ala Arg Glu Arg Val Tyr Glu Phe Leu Ser Ala Trp Ser Thr Pro
        275                 280                 285

Gln Arg Phe Glu Cys Asp Gln Glu Gly Ala Asn Thr Arg Ala Trp
    290                 295                 300

Arg Thr Ser Leu Leu Ile Ala Leu Gly Thr Leu Leu Ala Leu Val Cys
305                 310                 315                 320

Val Phe Val Ile Cys Arg Arg Tyr Leu Val Met Gln Arg Leu Phe Pro
                325                 330                 335

Arg Ile Pro His Met Lys Asp Pro Ile Gly Asp Ser Phe Gln Asn Asp
            340                 345                 350

Lys Leu Val Val Trp Glu Ala Gly Lys Ala Gly Leu Glu Glu Cys Leu
        355                 360                 365

Val Thr Glu Val Gln Val Val Gln Lys Thr
    370                 375

<210> SEQ ID NO 12
<211> LENGTH: 300
<212> TYPE: PRT
<213> ORGANISM: Homo sapiens

<400> SEQUENCE: 12

Met Val Leu Leu Trp Leu Thr Leu Leu Leu Ile Ala Leu Pro Cys Leu
1               5                   10                  15

Leu Gln Thr Lys Glu Gly Gly Lys Pro Trp Ala Gly Ala Glu Asn Leu
            20                  25                  30

Thr Cys Trp Ile His Asp Val Asp Phe Leu Ser Cys Ser Trp Ala Val
        35                  40                  45

Gly Pro Gly Ala Pro Ala Asp Val Gln Tyr Asp Leu Tyr Leu Asn Val
    50                  55                  60

Ala Asn Arg Arg Gln Gln Tyr Glu Cys Leu His Tyr Lys Thr Asp Ala
65                  70                  75                  80

Gln Gly Thr Arg Ile Gly Cys Arg Phe Asp Asp Ile Ser Arg Leu Ser
                85                  90                  95
```

```
Ser Gly Ser Gln Ser Ser His Ile Leu Val Arg Gly Arg Ser Ala Ala
            100                 105                 110

Phe Gly Ile Pro Cys Thr Asp Lys Phe Val Val Phe Ser Gln Ile Glu
            115                 120                 125

Ile Leu Thr Pro Pro Asn Met Thr Ala Lys Cys Asn Lys Thr His Ser
            130                 135                 140

Phe Met His Trp Lys Met Arg Ser His Phe Asn Arg Lys Phe Arg Tyr
145                 150                 155                 160

Glu Leu Gln Ile Gln Lys Arg Met Gln Pro Val Ile Thr Glu Gln Val
                165                 170                 175

Arg Asp Arg Thr Ser Phe Gln Leu Leu Asn Pro Gly Thr Tyr Thr Val
            180                 185                 190

Gln Ile Arg Ala Arg Glu Arg Val Tyr Glu Phe Leu Ser Ala Trp Ser
            195                 200                 205

Thr Pro Gln Arg Phe Glu Cys Asp Gln Glu Glu Gly Ala Asn Thr Arg
            210                 215                 220

Ala Trp Arg Thr Ser Leu Leu Ile Ala Leu Gly Thr Leu Leu Ala Leu
225                 230                 235                 240

Val Cys Val Phe Val Ile Cys Arg Arg Tyr Leu Val Met Gln Arg Leu
                245                 250                 255

Phe Pro Arg Ile Pro His Met Lys Asp Pro Ile Gly Asp Ser Phe Gln
            260                 265                 270

Asn Asp Lys Leu Val Val Trp Glu Ala Gly Lys Ala Gly Leu Glu Glu
            275                 280                 285

Cys Leu Val Thr Glu Val Gln Val Val Gln Lys Thr
290                 295                 300
```